US006426413B1

(12) United States Patent
Wannamaker et al.

(10) Patent No.: US 6,426,413 B1
(45) Date of Patent: Jul. 30, 2002

(54) INHIBITORS OF CASPASES

(75) Inventors: Marion W. Wannamaker, Stow; Paul Charifson, Framingham; David J. Lauffer, Stow; Michael D. Mullican, Needham, all of MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 09/654,855

(22) Filed: Sep. 5, 2000

Related U.S. Application Data

(63) Continuation of application No. PCT/US99/05124, filed on Mar. 9, 1999.
(60) Provisional application No. 60/077,327, filed on Mar. 9, 1998.

(51) Int. Cl.$^7$ .................... C07D 243/02; C07D 401/14; C07D 405/12; C07D 401/12; A61K 31/55

(52) U.S. Cl. .................... 540/524; 514/219; 540/492; 540/500; 540/501; 540/502; 540/503

(58) Field of Search .................... 540/492, 500, 540/501, 502, 503; 514/218, 219

(56) References Cited

U.S. PATENT DOCUMENTS

| | | | |
|---|---|---|---|
| 4,465,679 A | 8/1984 | Huang | 514/183 |
| 5,008,245 A | 4/1991 | Digenis et al. | 514/18 |
| 5,055,451 A | 10/1991 | Krantz et al. | 514/19 |
| 5,158,936 A | 10/1992 | Krantz et al. | 514/19 |
| 5,411,985 A | 5/1995 | Bills et al. | 514/460 |
| 5,416,013 A | 5/1995 | Black et al. | 435/226 |
| 5,430,128 A | 7/1995 | Chapman et al. | 530/330 |
| 5,434,248 A | 7/1995 | Chapman et al. | 530/330 |
| 5,446,128 A * | 8/1995 | Kahn | 530/317 |
| 5,462,939 A | 10/1995 | Dolle et al. | 514/231.5 |
| 5,486,623 A | 1/1996 | Zimmerman et al. | 549/417 |
| 5,498,616 A | 3/1996 | Mallamo et al. | 514/300 |
| 5,498,695 A | 3/1996 | Daumy et al. | 530/331 |
| 5,552,400 A | 9/1996 | Dolle | 514/221 |
| 5,565,430 A | 10/1996 | Dolle et al. | 514/19 |
| 5,585,357 A | 12/1996 | Dolle et al. | 514/18 |
| 5,585,486 A | 12/1996 | Dolle et al. | 544/182 |
| 5,639,745 A | 6/1997 | Dolle et al. | 514/183 |
| 5,670,494 A | 9/1997 | Dolle et al. | 514/86 |
| 5,716,929 A | 2/1998 | Bemis | 514/18 |
| 5,874,424 A | 2/1999 | Batchelor | 514/221 |

FOREIGN PATENT DOCUMENTS

| | | |
|---|---|---|
| EP | A-0 135 349 | 3/1985 |
| EP | A-0 410 411 | 1/1991 |
| EP | A-0 417 721 | 3/1991 |
| EP | A-0 519 748 | 12/1992 |
| EP | A-0 525 420 | 2/1993 |
| EP | A-0 528 487 | 2/1993 |
| EP | A-0 529 713 | 3/1993 |
| EP | A-0 533 226 | 3/1993 |
| EP | A-0 533 350 | 3/1993 |
| EP | A-0 547 699 | 6/1993 |
| EP | A-0 618 223 | 10/1994 |

(List continued on next page.)

OTHER PUBLICATIONS

M. Ator, "Peptide and Non–peptide Inhibitors of Interleukin–1β Converting Enzyme", Cambridge Healthtech Institute (Inflammatory Cytokine Antagonists Targets, Straegies, and Indicator), (1994).

M.A. Ator and R.E. Dolle, "Interleukin–1β Converting Enzyme: Biology and the Chemistry of Inhibitors", *Curr. Pharm. Design*, 1, pp. 191–210 (1995).

K. Chapman, "Synthesis of Potent Reversible Inhibitor of Interleukin–1β Converting Enzyme", *Bioor. Med. Chem. Lett.*, 2, pp. 613–618 (1992).

R. Dolle et al., "Aspartyl α–((Diphenylphosphinyl)oxy)methyl Ketones as Novel Inhibitors of Interleukin–1β Converting Enzyme. Utility of the Diphenylphosphinic Acid Leaving Group for the Inhibition of Cysteine Proteases", *J. Med. Chem.*, 38, pp. 220–222 (1995).

R. Dolle et al., "Aspartyl α–((1–Phenyl–3–(trifluoromethyl)–pyrazol–5–yl)oxy)methyl Ketones as Interleukin–1β Converting Enzyme Inhibitors. Significance of the $P_1$ and $P_3$ Amido Nitrogens for Enzyme–Peptide Inhibitor Binding", *J. Med. Chem.*, 37, pp. 3863–3865 (1994).

R. Dolle et al., "$P_1$ Aspartate–Based Peptide α–((2, 6–Dichlorobenzoyl)oxy)methyl Ketones as Potent Time–Dependent Inhibitors of Interleukin–1β–Converting Enzyme" *J. Med. Chem.*, 37, pp. 563–564 (1994).

P. Edwards et al, "Design, Synthesis, and Kinetic Evaluation of a Unique Class of Elastase Inhibitors, the Peptidyl α–Ketobenzoxazoles, and the X–ray Crystal Structure of the Covalent Complex between Porcine Pancreatic Elastase and Ac–Ala–Pro–Val–2–Benzoxazole", *J. Am. Chem. Soc.*, 114, pp. 1854–1863 (1992).

(List continued on next page.)

*Primary Examiner*—Bruck Kifle
(74) *Attorney, Agent, or Firm*—Fish & Neave; James F. Haley, Jr.; Kristin M. Joslyn

(57) ABSTRACT

The present invention relates to novel classes of compounds which are caspase inhibitors, in particular interleukin-1β converting enzyme ("ICE") inhibitors. This invention also relates to pharmaceutical compositions comprising these compounds. The compounds and pharmaceutical compositions of this invention are particularly well suited for inhibiting caspase activity and consequently, may be advantageously used as agents against interleukin-1-("IL-1"), apoptosis-, interferon-γ inducing factor-(IGIF), or interferon-γ-("IFN-γ") mediated diseases, including inflammatory diseases, autoimmune diseases, destructive bone disorders, proliferative disorders, infectious diseases, and degenerative diseases. This invention also relates to methods for inhibiting caspase activity and decreasing IGIF production and IFN-γ production and methods for treating interleukin-1, apoptosis-, and interferon-γ-mediated diseases using the compounds and compositions of this invention. This invention also relates to methods of preparing the compounds of this invention.

22 Claims, No Drawings

FOREIGN PATENT DOCUMENTS

| | | |
|---|---|---|
| EP | A-0 623 592 | 11/1994 |
| EP | A-0 623 606 | 11/1994 |
| EP | A-0 644 197 | 3/1995 |
| EP | A-0 644 198 | 3/1995 |
| WO | WO 91/15577 | 10/1991 |
| WO | WO 93/05071 | 3/1993 |
| WO | WO 93/09135 | 5/1993 |
| WO | WO 93/14777 | 8/1993 |
| WO | WO 93/16710 | 9/1993 |
| WO | WO 94/00154 | 1/1994 |
| WO | WO 94/03480 | 2/1994 |
| WO | WO 95/00160 | 1/1995 |
| WO | WO 95/05192 | 2/1995 |
| WO | WO 95/26958 | 10/1995 |
| WO | WO 95/29672 | 11/1995 |
| WO | WO 95/31535 | 11/1995 |
| WO | WO 95/35308 | 12/1995 |
| WO | WO 95/35367 | 12/1995 |
| WO | WO 96/03982 | 2/1996 |
| WO | WO 96/25408 | 8/1996 |
| WO | WO 96/30395 | 10/1996 |
| WO | WO 96/40647 | 12/1996 |
| WO | WO 97/07805 | 3/1997 |
| WO | WO 97/08174 | 3/1997 |
| WO | WO 97/22619 | 6/1997 |
| WO | WO 97/24339 | 7/1997 |
| WO | WO 98/04539 | 2/1998 |
| WO | WO 98/10778 | 3/1998 |
| WO | WO 98/11109 | 3/1998 |
| WO | WO 98/11129 | 11/1998 |
| WO | WO 98/49189 | 11/1998 |

OTHER PUBLICATIONS

P.R. Elford et al. "Reduction of Inflammation and Pyrexia in the Rat by Oral Administration of SDZ 224–015, and Inhibitor of the Interleukin–1β Converting Enzyme", Br. J. Pharmacology, 115, pp. 601–606 (1995).

T. –P.D. Fan et al., "Stimulation of Angiogenesis by Substance P and Interleukin–1 in the Rat and Its Inhibition by $NK_1$ or Interleukin–1 Receptor Antagonists", Br. J. Pharmacol., 110, 43–49 (1993).

I. Fauszt et al., "Inhibition of Interleukin–1β Converting Enzyme by Peptide Derivatives", Proc. of the 13th Am. Peptide Symp., Jun. 20–25, 1993; Hodges, R.S. and Smith, J.A., Eds., Peptides, pp. 589–891 (1994).

D. Fletcher et al., "A Synthetic Inhibitor of Interleukin–1β Converting Enzyme Prevents Endotoxin–Induced Interleukin–1β Production In Vitro and In Vivo", J. Interfer. Cytokine Res., 15, pp. 243–248 (1995).

T. Graybill et al., "The Preparation and Evaluation of Peptidic Aspartyl Hemiacetals as Reversible Inhibitors of ICE", Am. Chem. Soc. Abs. (206th Natl. Mtg.), MEDI 235 (1993).

T. Graybill, et al., "Preparation and Evaluation of Peptidic Aspartyl Hemiacetals as Reversible Inhibitors of Interleukin–1β Converting Enzyme (ICE)", Int. J. Peptide Protein Res., 44, pp. 173–182 (1994).

S. Hanessian et al., "Design and Synthesis of a Prototype Model Antagonist of Tachykinin NK–2 Receptor", Bioor. Med. Chem. Lett., 11, 1397–1400 (1994).

D. Karanewsky et al., "Conformationally Constrained Inhibitors of caspase-1 (Interleukin–1β Converting Enzyme) and of the Human CED–3 Homologne Caspase-3) (CPP32, Apopain)", Bioorg. Med. Chem. Lett., 8, pp. 2757–2762 (1998).

A. MacKenzie et al., "An Inhibitor of the Interleukin–1β–Processing Enzyme Blocks IL–1 Release and Reduces Pyrexia and Acute Inflammation", Inflammation Research Association (7th Internat. Conf.), W42 (1994).

B. Miller et al., "Inhibitor on Mature IL–1β Production in Murine Macrophages and a Murine Model of Inflammation by WIN 67694, an Inhibitor of IL–β Converting Enzyme[1]", J. Immunol., 154, pp. 1331–1338 (1995).

A.M.M. Mjalli et al., "Activated Ketones as Potent Reversible Inhibitors of Interleukin–1β Converting Enzyme", Bioorg. Med. Chem. Lett., 4, pp. 1965–1968 (1994).

A.M.M. Mjalli et al., "Phenylalkyl Ketones as Potent Reversible Inhibitors of Interleukin–1β Converting Enzyme", Bioorg. Med. Chem. Lett., 3, pp. 2689–2692 (1993).

M.D. Mullican et al., "The Synthesis and Evaluation of Peptidyl Aspartyl Aldehydes as Inhibitors of ICE", Bioorg. Med. Chem. Lett., 4, 2359–2364 (1994).

M. Pennington & N. Thornberry, "Synthesis of a Fluorogenic Interleukin–1β Converting Enzyme Substrate Based on Resonance Energy Transfer", Pept. Res., 7, pp. 72–76 (1994).

C. Prasad et al., "$P_1$ Aspartate–Based Peptide α–Arylacyloxy– and α–Aryloxymethyl Ketones as Potent Time–Dependent Inhibitors of Interleukin 1β Converting Enzyme", Am. Chem. Soc. Abs. (24th Med. Shem. Symp.), 66 (1994).

C. Ray et al., "Viral Inhibition of Inflammation: Cowpox Virus Encodes an Inhibitor of the Interleukin–1β Converting Enzyme", Cell, 69, pp. 597–604 (1992).

L. Reiter, "Peptidic p–Nitroanilide Substrates of Interleukin–1β–Converting Enzyme", Int. J. Pept. Protein Res., 43, pp. 87–96 (1994).

L. Revesz et al., "Synthesis of P1 Aspartate–Based Peptide Acyloxymethyl and Fluoromethyl Ketones as Inhibitors of Interleukin–β–Converting Enzyme", Tetrahedron Lett., 35, pp. 9693–9696 (1994).

R.P. Robinson and K.M. Donahue, "Synthesis of a Peptidyl Dufluoro Ketone Bearing the Aspartic Acid Side Chain: An Inhibitor of Interleukin–β Converting Enzyme", J. Org. Chem., 57, 7309–7314 (1992).

S. Schmidt et al., "Synthesis and Evaluation of Aspartyl α–Chloro–, α–Aryloxy–, and α–Arylacyloxymethyl Ketones as Inhibitors of Interleukin–1β Converting Enzyme", Am. Chem. Soc. Abs. (208th Natl. Mtg.), MEDI 4, (1994).

P. Sleath et al., "Substrate Specificity of the Proteasse that Processes Human Interleukin–1β", J. Biol. Chem., 265, pp. 14526–14528 (1990).

A.F. Spatola, in "Chemistry and Biochemistry of Amino Acids, Peptides, and Proteins", 7, ch. 5, pp. 267–281, Weinstein, B. ed., Marcel Dekker, Inc., New York (1983).

N. Thornberry et al., "Inactivation of Interleukin–1β Converting Enzyme by Peptide (Acyloxy)methyl Ketones", Biochemistry, 33, pp. 3934–3940 (1994).

J. Uhl et al., Secretion of Human Monocyte Mature IL–1β: Optimization of Culture Conditions and Inhibition by ICE Inhibitors, Inflammation Res., 44, pp. S211–S212 (1995).

* cited by examiner

INHIBITORS OF CASPASES

CROSS-REFERENCE TO RELATED APPLICATIONS

This application is a continuing application of copending International patent application PCT/US99/05124, filed Mar. 9, 1999, which claims priority from U.S. provisional patent application No. 60/077,327 filed Mar. 9, 1998.

TECHNICAL FIELD OF THE INVENTION

The present invention relates to novel classes of compounds which are caspase inhibitors, in particular interleukin-1β converting enzyme ("ICE") inhibitors. This invention also relates to pharmaceutical compositions comprising these compounds. The compounds and pharmaceutical compositions of this invention are particularly well suited for inhibiting caspase activity and consequently, may be advantageously used as agents against interleukin-1-("IL-1"), apoptosis-, interferon-γ inducing factor-(IGIF), or interferon-γ-("IFN-γ") mediated diseases, including inflammatory diseases, autoimmune diseases, destructive bone disorders, proliferative disorders, infectious diseases, and degenerative diseases. This invention also relates to methods for inhibiting caspase activity and decreasing IGIF production and IFN-γ production and methods for treating interleukin-1, apoptosis-, and interferon-γ-mediated diseases using the compounds and compositions of this invention. This invention also relates to methods of preparing the compounds of this invention.

BACKGROUND OF THE INVENTION

Interleukin 1 ("IL-1") is a major pro-inflammatory and immunoregulatory protein that stimulates fibroblast differentiation and proliferation, the production of prostaglandins, collagenase and phospholipase by synovial cells and chondrocytes, basophil and eosinophil degranulation and neutrophil activation. Oppenheim, J. H. et al, *Immunology Today*, 7, pp. 45–56 (1986). As such, it is involved in the pathogenesis of chronic and acute inflammatory and autoimmune diseases. For example, in rheumatoid arthritis, IL-1 is both a mediator of inflammatory symptoms and of the destruction of the cartilage proteoglycan in afflicted joints. Wood, D. D. et al., *Arthritis Rheum.* 26, 975, (1983); Pettipher, E. J. et al., *Proc. Natl. Acad. Sci. USA* 71, 295 (1986); Arend, W. P. and Dayer, J. M., *Arthritis Rheum.* 38, 151 (1995). IL-1 is also a highly potent bone resorption agent. Jandiski, J. J., *J. Oral Path* 17, 145 (1988); Dewhirst, F. E. et al., *J. Immunol.* 8, 2562 1985). It is alternately referred to as "osteoclast activating factor" in destructive bone diseases such as osteoarthritis and multiple myeloma. Bataille, R. et al., *Int. J. Clin. Lab. Res.* 21(4), 283 (1992). In certain proliferative disorders, such as acute myelogenous leukemia and multiple myeloma, IL-1 can promote tumor cell growth and adhesion. Bani, M. R., *J. Natl. Cancer Inst.* 83, 123 (1991); Vidal-Vanaclocha, F., *Cancer Res.* 54, 2667 (1994). In these disorders, IL-1 also stimulates production of other cytokines such as IL-6, which can modulate tumor development (Tartour et al., *Cancer Res.* 54, p. 6243 (1994). IL-1 is predominantly produced by peripheral blood monocytes as part of the inflammatory response and exists in two distinct agonist forms, IL-1α and IL-1β. Mosely, B. S. et al., *Proc. Nat. Acad. Sci.*, 84, pp. 4572–4576 (1987); Lonnemann, G. et al., *Eur. J. Immunol.*, 19, pp. 1531–1536 (1989).

IL-1β is synthesized as a biologically inactive precursor, pIL-1β. pIL-1β lacks a conventional leader sequence and is not processed by a signal peptidase. March, C. J., *Nature*, 315, pp. 641–647 (1985). Instead, pIL-1β is cleaved by interleukin-1β converting enzyme ("ICE") between Asp-116 and Ala-117 to produce the biologically active C-terminal fragment found in human serum and synovial fluid. Sleath, P. R., et al., *J. Biol. Chem.*, 265, pp. 14526–14528 (1992); A. D. Howard et al., *J. Immunol.*, 147, pp. 2964–2969 (1991). ICE is a cysteine protease localized primarily in monocytes. It converts precursor IL-1β to the mature form. Black, R. A. et al., *FEBS Lett.*, 247, pp. 386–390 (1989); Kostura, M. J. et al., *Proc. Natl. Acad. Sci. U.S.A.*, 86, pp. 5227–5231 (1989). Processing by ICE is also necessary for the transport of mature IL-1β through the cell membrane.

ICE is a member of a family of homologous enzymes called caspases. These homologs have sequence similarities in the active site regions of the enzymes. Such homologs (caspases) include TX (or $ICE_{rel-II}$ or ICH-2) (Faucheu, et al., *EMBO J.*, 14, p. 1914 (1995); Kamens J., et al., *J. Biol. Chem.*, 270, p. 15250 (1995); Nicholson et al., *J. Biol. Chem.*, 270 15870 (1995)), TY (or $ICE_{rel-III}$) (Nicholson et al., *J. Biol. Chem.*, 270, p. 15870 (1995); ICH-1 (or Nedd-2) (Wang, L. et al., *Cell*, 78, p. 739 (1994)), MCH-2, (Fernandes-Alnemri, T. et al., *Cancer Res.*, 55, p. 2737 (1995), CPP32 (or YAMA or apopain) (Fernandes-Alnemri, T. et al., *J. Biol. Chem.*, 269, p. 30761 (1994); Nicholson, D. W. et al., *Nature*, 376, p. 37 (1995)), and CMH-1 (or MCH-3) (Lippke, et al., *J. Biol. Chem.*, (1996); Fernandes-Alnemri, T. et al., *Cancer Res.*, (1995)).

Each of these ICE homologs, as well as ICE itself, is capable of inducing apoptosis when overexpressed in transfected cell lines. Inhibition of one or more of these homologs with the peptidyl ICE inhibitor Tyr-Val-Ala-Asp-chloromethylketone results in inhibition of apoptosis in primary cells or cell lines. Lazebnik et al., *Nature*, 371, p. 346 (1994).

Caspases also appear to be involved in the regulation of programmed cell death or apoptosis. Yuan, J. et al., *Cell*, 75, pp. 641–652 (1993); Miura, M. et al., *Cell*, 75, pp. 653–660 (1993); Nett-Fiordalisi, M. A. et al., *J. Cell Biochem.*, 17B, p. 117 (1993). In particular, ICE or ICE homologs are thought to be associated with the regulation of apoptosis in neurodegenerative diseases, such as Alzheimer's and Parkinson's disease. Marx, J. and M. Baringa, *Science*, 259, pp. 760–762 (1993); Gagliardini, V. et al., *Science*, 263, pp. 826–828 (1994). Therapeutic applications for inhibition of apoptosis may include treatment of Alzheimer's disease, Parkinson's disease, stroke, myocardial infarction, spinal atrophy, and aging.

ICE has been demonstrated to mediate apoptosis (programmed cell death) in certain tissue types. Steller, H., *Science*, 267, p. 1445 (1995); Whyte, M. and Evan, G., *Nature*, 376, p. 17 (1995); Martin, S. J. and Green, D. R., *Cell*, 82, p. 349 (1995); Alnemri, E. S., et al., *J. Biol. Chem.*, 270, p. 4312 (1995); Yuan, J. *Curr. Opin. Cell Biol.*, 7, p. 211 (1995). A transgenic mouse with a disruption of the ICE gene is deficient in Fas-mediated apoptosis (Kuida, K. et al., *Science* 267, 2000 (1995)). This activity of ICE is distinct from its role as the processing enzyme for pro-IL-1β. It is conceivable that in certain tissue types, inhibition of ICE may not affect secretion of mature IL-1β, but may inhibit apoptosis.

Enzymatically active ICE has been previously described as a heterodimer composed of two subunits, p20 and p10 (20 kDa and 10 kDa molecular weight, respectively). These subunits are derived from a 45 kDa proenzyme (p45) by way of a p30 form, through an activation mechanism that is autocatalytic. Thornberry, N. A. et al., Nature, 356, pp. 768–774 (1992). The ICE proenzyme has been divided into several functional domains: a prodomain (p14), a p22/20 subunit, a polypeptide linker and a p10 subunit. Thornberry et al., supra; Casano et al., Genomics, 20, pp. 474–481 (1994).

Full length p45 has been characterized by its cDNA and amino acid sequences. PCT patent applications WO 91/15577 and WO 94/00154. The p20 and p10 cDNA and amino acid sequences are also known. Thornberry et al., supra. Murine and rat ICE have also been sequenced and cloned. They have high amino acid and nucleic acid sequence homology to human ICE. Miller, D. K. et al., Ann. N.Y. Acad. Sci., 696, pp. 133–148 (1993); Molineaux, S. M. et al., Proc. Nat. Acad. Sci., 90, pp. 1809–1813 (1993). The three-dimensional structure of ICE has been determined at atomic resolution by X-ray crystallography. Wilson, K. P., et al., Nature, 370, pp. 270–275 (1994). The active enzyme exists as a tetramer of two p20 and two p10 subunits.

Recently, ICE and other members of the ICE/CED-3 family have been linked to the conversion of pro-IGIF to IGIF or to the production of IFN-γ in vivo (PCT application PCT/US96/20843, filed Dec. 20, 1996, published Jun. 26, 1997 under publication no. WO 97/22619, which is incorporated herein by reference). IGIF is synthesized in vivo as the precursor protein "pro-IGIF".

Interferon-gamma inducing factor (IGIF) is an approximately 18-kDa polypeptide that stimulates T-cell production of interferon-gamma (IFN-γ). IGIF is produced by activated Kupffer cells and macrophages in vivo and is exported out of such cells upon endotoxin stimulation. Thus, a compound that decreases IGIF production would be useful as an inhibitor of such T-cell stimulation which in turn would reduce the levels of IFN-γ production by those cells.

IFN-γ is a cytokine with immunomodulatory effects on a variety of immune cells. In particular, IFN-γ is involved in macrophage activation and Th1 cell selection (F. Belardelli, APMIS, 103, p. 161 (1995)). IFN-γ exerts its effects in part by modulating the expression of genes through the STAT and IRF pathways (C. Schindler and J. E. Darnell, Ann. Rev. Biochem., 64, p. 621 (1995); T. Taniguchi, J. Cancer Res. Clin. Oncol., 121, p. 516 (1995)).

Mice lacking IFN-γ or its receptor have multiple defects in immune cell function and are resistant to endotoxic shock (S. Huang et al., Science, 259, p. 1742 (1993); D. Dalton et al., Science, 259, p. 1739 (1993); B. D. Car et al., J. Exp. Med., 179, p. 1437 (1994)). Along with IL-12, IGIF appears to be a potent inducer of IFN-γ production by T cells (H. Okamura et al., Infection and Immunity, 63, p. 3966 (1995); H. Okamura et al., Nature, 378, p. 88 (1995); S. Ushio et al., J. Immunol., 156, p. 4274 (1996)).

IFN-γ has been shown to contribute to the pathology associated with a variety of inflammatory, infectious and autoimmune disorders and diseases. Thus, compounds capable of decreasing IFN-γ production would be useful to ameliorate the effects of IFN-γ related pathologies.

Accordingly, compositions and methods capable of regulating the conversion of pro-IGIF to IGIF would be useful for decreasing IGIF and IFN-γ production in vivo, and thus for ameliorating the detrimental effects of these proteins which contribute to human disorders and diseases.

Caspase inhibitors represent a class of compounds useful for the control of inflammation or apoptosis or both. Peptide and peptidyl inhibitors of ICE have been described. PCT patent applications WO 91/15577; WO 93/05071; WO 93/09135; WO 93/14777 and WO 93/16710; and European patent application 0 547 699. Such peptidyl inhibitors of ICE have been observed to block the production of mature IL-1β in a mouse model of inflammation (vide infra) and to suppress growth of leukemia cells in vitro (Estrov et al., Blood 84, 380a (1994)). However, due to their peptidic nature, such inhibitors are typically characterized by undesirable pharmacologic properties, such as poor cellular penetration and cellular activity, poor oral absorption, poor stability and rapid metabolism. Plattner, J. J. and D. W. Norbeck, in Drug Discovery Technologies, C. R. Clark and W. H. Moos, Eds. (Ellis Horwood, Chichester, England, 1990), pp. 92–126. This has hampered their development into effective drugs.

Non-peptidyl compounds have also been reported to inhibit ICE in vitro. PCT patent application WO 95/26958; U.S. Pat. No. 5,552,400; Dolle et al., J. Med. Chem., 39, pp. 2438–2440 (1996). It is not clear however whether these compounds have the appropriate pharmacological profiles to be therapeutically useful.

Accordingly, the need exists for compounds that can effectively inhibit caspases for use as agents for preventing and treating chronic and acute forms of IL-1-mediated diseases, apoptosis-, IGIF-, or IPN-γ-mediated diseases, as well as inflammatory, autoimmune, destructive bone, proliferative, infectious, or degenerative diseases.

SUMMARY OF THE INVENTION

The present invention provides novel classes of compounds, and pharmaceutically acceptable derivatives thereof, that are useful as caspases inhibitors, in particular as ICE inhibitors. These compounds can be used alone or in combination with other therapeutic or prophylactic agents, such as antibiotics, immunomodulators or other anti-inflammatory agents, for the treatment or prophylaxis of diseases mediated by IL-1, apoptosis, IGIF or IFN-γ. According to a preferred embodiment, the compounds of this invention are capable of binding to the active site of ICE and inhibiting the activity of that enzyme.

It is a principal object of this invention to provide novel classes of compounds represented by formulas:

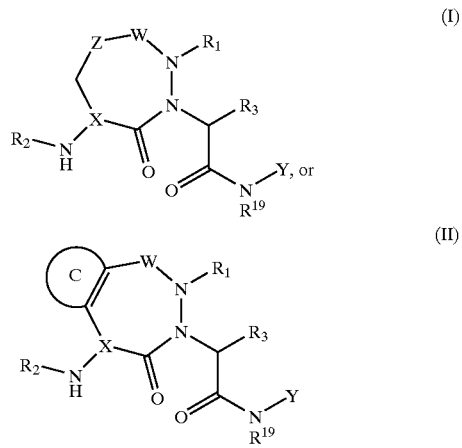

wherein the various substituents are described herein.

This invention also provides compositions comprising compounds represented by formulae (I) and (II), methods for using these compositions in the treatment or prevention of various disorders, and methods for preparing these compounds.

DETAILED DESCRIPTION OF THE INVENTION

In order that the invention described herein may be more fully understood, the following detailed description is set forth.

The following abbreviations and definitions are used throughout the application.

| Abbreviations | |
|---|---|
| Ac$_2$O | acetic anhydride |
| n-Bu | normal-butyl |
| DMF | dimethylformamide |
| DIEA | N,N-diisopropylethylamine |
| EDC | 1-(3-Dimethylaminopropyl)-3-ethylcarbodiimide hydrochloride |
| Et$_2$O | diethyl ether |
| EtOAc | ethyl acetate |
| Fmoc | 9-fluorenylmethyoxycarbonyl |
| HBTU | O-benzotriazol-1-yl-N,N,N',N'-tetramethyluronium hexafluorophosphate |
| HOBT | 1-hydroxybenzotriazole hydrate |
| MeOH | methanol |
| TFA | trifluoroacetic acid |

The term "caspase" refers to an enzyme that is a member of the family of enzymes that includes ICE (see H. Hara, *Natl. Acad. Sci.*, 94, pp. 2007–2012 (1997).

The terms "HBV", "HCV" and "HGV" refer to hepatitis-B virus, hepatitis-C virus and hepatitis-G virus, respectively.

The term "$K_i$" refers to a numerical measure of the effectiveness of a compound in inhibiting the activity of a target enzyme such as ICE. Lower values of $K_i$ reflect higher effectiveness. The $K_i$ value is a derived by fitting experimentally determined rate data to standard enzyme kinetic equations (see I. H. Segel, *Enzyme Kinetics*, Wiley-Interscience, 1975).

The term "interferon gamma inducing factor" or "IGIF" refers to a factor which is capable of stimulating the endogenous production of IFN-γ.

The term "caspase inhibitor" refers to a compound which is capable of demonstrating detectable inhibition of one or more caspases. The term "ICE inhibitor" refers to a compound which is capable of demonstrating detectable inhibition of ICE and optionally of one or more additional caspases. Inhibition of these enzymes may be determined using the methods described and incorporated by reference herein. The skilled practitioner realizes that an in vivo enzyme inhibitor is not necessarily an in vitro enzyme inhibitor. For example, a prodrug form of a compound typically demonstrates little or no activity in in vitro assays. Such prodrug forms may be altered by metabolic or other biochemical processes in the patient to provide an in vivo enzyme inhibitor.

The term "cytokine" refers to a molecule which mediates interactions between cells.

The term "condition" refers to any disease, disorder or effect that produces deleterious biological consequences in a subject.

The term "subject" refers to an animal, or to one or more cells derived from an animal. Preferably, the animal is a mammal, most preferably a human. Cells may be in any form, including but not limited to cells retained in tissue, cell clusters, immortalized cells, transfected or transformed cells, and cells derived from an animal that have been physically or phenotypically altered.

The term "patient" as used in this application refers to any mammal, preferably humans.

The term "alkyl" refers to a straight-chained or branched, saturated aliphatic hydrocarbon containing 1 to 6 carbon atoms.

The term "alkenyl" refers to a straight-chained or branched unsaturated hydrocarbon containing 2 to 6 carbon atoms and at least one double bond.

The term "alkynyl" refers to a straight-chained or branched unsaturated hydrocarbon containing 2 to 6 carbon atoms and at least one triple bond.

The term "cycloalkyl" refers to a mono- or polycyclic, non-aromatic, hydrocarbon ring system which may optionally contain unsaturated bonds in the ring system. Examples include cyclohexyl, adamantyl and norbornyl.

The term "aryl" refers to a mono- or polycyclic ring system which contains 6, 10, 12 or 14 carbons in which at least one ring of the ring system is aromatic. The aryl groups of this invention are optionally singly or multiply substituted with $R^{17}$. Examples of aryl ring systems include, phenyl, naphthyl, and tetrahydronaphthyl.

The term "heteroaryl" refers to a mono- or polycyclic ring system which contains 1 to 15 carbon atoms and 1 to 4 heteroatoms, and in which at least one ring of the ring system is aromatic. Heteroatoms are sulfur, nitrogen or oxygen. The heteroaryl groups of this invention are optionally singly or multiply substituted with $R^{17}$.

The term "heterocyclic" refers to a mono- or polycyclic ring system which contains 1 to 15 carbon atoms and 1 to 4 heteroatoms, in which the mono- or polycyclic ring system may optionally contain unsaturated bonds but is not aromatic. Heteroatoms are independently sulfur, nitrogen, or oxygen.

The term "alkylaryl" refers to an alkyl group, wherein one or more hydrogen atoms of the alkyl group is replaced by one or more aryl radical.

The term "alkylheteroaryl" refers to an alkyl group, wherein a hydrogen atom of the alkyl group is replaced by a heteroaryl radical.

The term "substitute" refers to the replacement of a hydrogen atom in a compound with a substituent group.

The term "straight chain" refers to a contiguous unbranching string of covalently bound atoms. The straight chain may be substituted, but these substituents are not a part of the straight chain.

The term "amino acid side chain" refers to the substituent bound to the α-carbon of a either a natural or a non-natural α-amino acid.

In chemical formulas, parenthesis are used herein to denote connectivity in molecules or groups. In particular, parentheses are used to indicate: 1) that more than one atom or group is bonded to a particular atom; or 2) a branching point (i.e., the atom immediately before the open parenthesis is bonded both to the atom or group in the parentheses and the atom or group immediately after the closed parenthesis). An example of the first use is "—N(alkyl)$_2$", indicating two alkyl groups bond to an N atom. An example of the second use is "—C(O)NH$_2$", indicating a carbonyl group and an amino ("NH$_2$") group both bonded to the indicated carbon atom. A "—C(O)NH$_2$" group may be represented in other ways, including the following structure:

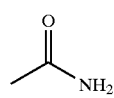

Substituents may be represented in various forms. These various forms are known to the skilled practitioner and may be used interchangeably. For example, a methyl substituent on a phenyl ring may be represented in any of the following forms:

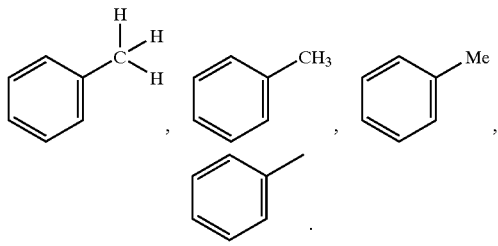

Various forms of substituents such as methyl are used herein interchangeably.

Other definitions are set forth in the specification where necessary.

COMPOUNDS OF THIS INVENTION

The compounds of one embodiment (A) of this invention are those of formula (I):

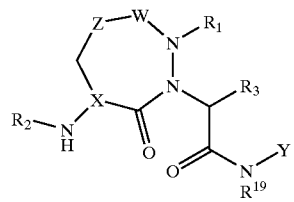

wherein:
Y is:

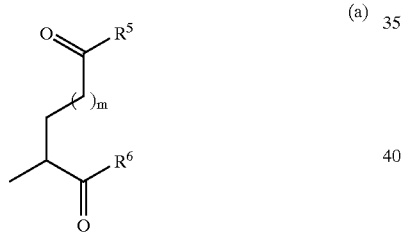

(a)

provided that when $R^5$ is —OH then Y can also be:

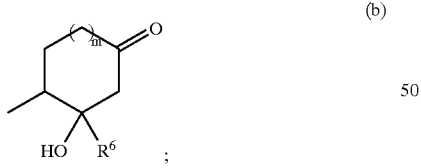

(b)

m is 0 or 1;
W is —$CH_2$—, —C(O)—, $S(O)_2$, or —S(O)—;
X is —C(H)—, —C($R^8$)—, or

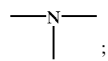

Z is —$CH_2$—, —O—, —S—, or —N($R^1$)—, provided that if Z is —N($R^1$)—, then W is —C(O)—, —$S(O)_2$—, or —S(O)—;
each $R^1$ is independently —H, —C(O)$R^8$, —$S(O)_2R^8$, —S(O)$R^8$, —$R^{21}$, -alkyl-$R^{21}$, -alkenyl-$R^{21}$, or -alkynyl-$R^{21}$;

$R^2$ is —C(O)$R^8$, —C(O)C(O)$R^8$, —$S(O)_2R^8$, —S(O)$R^8$, —C(O)O$R^8$, —C(O)N(H)$R^8$, —$S(O)_2$N(H)—$R^8$, —S(O)N(H)—$R^8$, —C(O)C(O)N(H)$R^8$, —C(O)CH=CH$R^8$, —C(O)$CH_2$O$R^8$, —C(O)$CH_2$N(H)$R^8$, —C(O)N($R^8$)$_2$, —$S(O)_2$N($R^8$)$_2$, —S(O)N($R^8$)$_2$, —C(O)C(O)N($R^8$)$_2$, —C(O)$CH_2$N($R^8$)$_2$, —$CH_2$—$R^8$, —$CH_2$-alkenyl-$R^8$, or —$CH_2$-alkynyl-$R^8$;

$R^3$ is —H, —$R^{21}$, -alkyl-$R^{21}$, -alkenyl-$R^{21}$, or -alkynyl-$R^{21}$;

each $R^4$ is independently —OH, —F, —Cl, —Br, —I, —$NO_2$, —CN, —$NH_2$, —$CO_2$H, —C(O)$NH_2$, —N(H)C(O)H, —N(H)C(O)$NH_2$, -alkyl, -cycloalkyl, -perfluoroalkyl, —O-alkyl, —N(H)alkyl, —N(alkyl)$_2$, —C(O)N(H)alkyl, —C(O)N(alkyl)$_2$, —N(H)C(O)alkyl, —N(H)C(O)N(H)alkyl, —N(H)C(O)N(alkyl)$_2$, —S-alkyl, —$S(O)_2$alkyl, —S(O)alkyl, —C(O)alkyl, —$CH_2NH_2$, —$CH_2$N(H)alkyl, —$CH_2$N(alkyl)$_2$, or —N(H)C(O)Oalkyl;

$R^5$ is —OH, —O$R^8$, or —N(H)OH;

$R^6$ is —H, —$CH_2$O$R^9$, —$CH_2$S$R^{10}$, —$CH_2$N(H)$R^9$, —$CH_2$N($R^9$)$R^{11}$, —C(H)$N_2$, —$CH_2$F, —$CH_2$Cl, —C(O)N($R^{11}$)$_2$, —$R^{13}$, or —$R^{14}$;

each $R^8$ is independently -alkyl, -cycloalkyl, -aryl, -heteroaryl, -heterocyclyl, -alkylcycloalkyl, -alkylaryl, -alkylheteroaryl, or -alkylheterocyclyl;

$R^9$ is —H, —C(O)aryl, —C(O)heteroaryl, —C(O)alkylaryl, —C(O)alkylheteroaryl, -alkylaryl, -alkylheteroaryl, -aryl, -heteroaryl, or —P(O)($R^{15}$)$_2$;

$R^{10}$ is -alkylaryl or -alkylheteroaryl;

each $R^{11}$ is independently —H, -alkyl, -aryl, -heteroaryl, -cycloalkyl, -alkylaryl, or -alkylheteroaryl;

$R^{13}$ is -alkylaryl or -alkylheteroaryl;

$R^{14}$ is

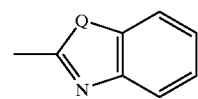

(i)

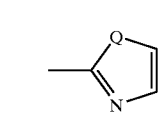

(ii)

(iii)

, or

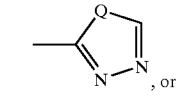

(iv)

wherein Q is —O— or —S—, any hydrogen atom in (i) is optionally replaced with —$R^{17}$, and any hydrogen atom in (ii), (iii), and (iv) is optionally replaced with —$R^{17}$, —$R^{18}$ or -alkyl-$R^{18}$;

each $R^{15}$ is independently —H, —OH, -alkyl, -aryl, -heteroaryl, -cycloalkyl, -alkylaryl, -alkylheteroaryl, —Oalkyl, —Oaryl, —Oheteroaryl, —Oalkylaryl, or —Oalkylheteroaryl;

each $R^{17}$ is independently —OH, —F, —Cl, —Br, —I, —$NO_2$, —CN, —$NH_2$, —$CO_2$H, —C(O)$NH_2$, —N(H)C(O)H, —N(H)C(O)$NH_2$, —$SO_2NH_2$, —C(O)H, -alkyl, -cycloalkyl, -perfluoroalkyl, —O-alkyl, —N(H)alkyl, —N(alkyl)$_2$, —CO$_2$alkyl, —C(O)N(H)alkyl, —C(O)N(alkyl)$_2$, —N(H)C(O)alkyl, —N(H)C(O)N(H)alkyl, —N(H)C(O)N(alkyl)$_2$, —S(O)$_2$N(H)alkyl, —S(O)N(H)alkyl, —S(O)$_2$N(alkyl)$_2$, —S(O)N(alkyl)$_2$, —S-alkyl, —S(O)$_2$alkyl, —S(O)alkyl, or —C(O)alkyl;

each $R^{18}$ is independently -aryl, -heteroaryl, -alkylaryl, -alkylheteroaryl, —O-aryl, —O-heteroaryl, —O-alkylaryl, —O-alkylheteroaryl, —N(H)aryl, —N(aryl)$_2$, —N(H)heteroaryl, —N(heteroaryl)$_2$, —N(H)alkylaryl, —N(alkylaryl)$_2$, —N(H)alkylheteroaryl, —N(alkylheteroaryl)$_2$, —S-aryl, —S-heteroaryl, —S-alkylaryl, —S-alkylheteroaryl, —C(O)aryl, —C(O)heteroaryl, —C(O)alkylaryl, —C(O)alkylheteroaryl, —CO$_2$aryl, —CO$_2$heteroaryl, —CO$_2$alkylaryl, —CO$_2$alkylheteroaryl, —C(O)N(H)aryl, —C(O)N(aryl)$_2$, —C(O)N(H)heteroaryl, —C(O)N(heteroaryl)$_2$, —C(O)N(H)alkylaryl, —C(O)N(alkylaryl)$_2$, —C(O)N(H)alkylheteroaryl, —C(O)N(alkylheteroaryl)$_2$, —SO$_2$-aryl, —S(O)-aryl, —S(O)$_2$-heteroaryl, —S(O)-heteroaryl, —S(O)$_2$-alkylaryl, —S(O)-alkylaryl, —S(O)$_2$-alkylheteroaryl, —S(O)-alkylheteroaryl, —S(O)$_2$N(H)-aryl, —S(O)N(H)-aryl, —S(O)$_2$NH-heteroaryl, —S(O)NH-heteroaryl, —S(O)$_2$N(H)-alkylaryl, —S(O)N(H)-alkylaryl, —S(O)$_2$N(H)-alkylheteroaryl, —S(O)N(H)-alkylheteroaryl, —S(O)$_2$N(aryl)$_2$, —S(O)N(aryl)$_2$, —S(O)$_2$N(heteroaryl)$_2$, —S(O)N(heteroaryl)$_2$, —S(O)$_2$N(alkylaryl)$_2$, —S(O)N(alkylaryl)$_2$, —S(O)$_2$N(alkylheteroaryl)$_2$, —S(O)N(alkylheteroaryl)$_2$, —N(H)C(O)N(H)aryl, —N(H)C(O)N(H)heteroaryl, —N(H)C(O)N(H)alkylaryl, —N(H)C(O)N(H)alkylheteroaryl, —N(H)C(O)N(aryl)$_2$, —N(H)C(O)N(heteroaryl)$_2$, —N(H)C(O)N(alkylaryl)$_2$, or —N(H)C(O)N(alkylheteroaryl)$_2$;

$R^{19}$ is hydrogen; and each $R^{21}$ is independently -aryl, -heteroaryl, cycloalkyl, or -heterocyclyl, wherein a hydrogen atom bound to any carbon atom is optionally replaced by $R^4$ and a hydrogen atom bound to any nitrogen atom is optionally replaced by $R^2$.

The compounds of another embodiment (B) of this invention are those of formula (II):

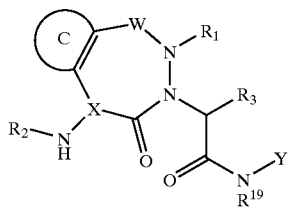

wherein:

C is an aryl or heteroaryl ring, wherein any hydrogen atom bound to the C ring is optionally substituted with —$R^4$; and the other substituents are as described above in embodiment (A).

The compounds of two other embodiments (C) and (D) of this invention are those of formulae (I) or (II), respectively, wherein:

Y is (c), (d), (e), or (f), when $R^{19}$ is hydrogen:

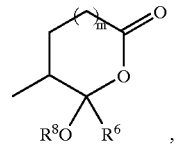

(c)

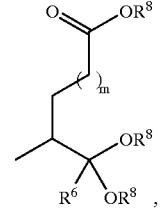

(d)

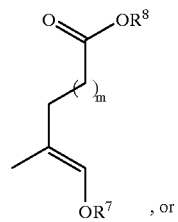

(e)

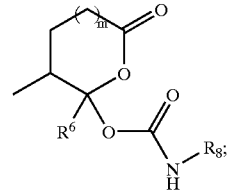

, or (f)

and when $R^{19}$ is not hydrogen, $R^{19}$ and Y, together with the nitrogen atom to which they are bound, form a ring (g):

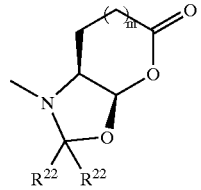

(g)

$R^7$ is —C(O)alkyl, —C(O)cycloalkyl, —C(O)alkyenyl, —C(O)alkylaryl, —C(O)alkylheteroaryl, —C(O)heterocycle, or —C(O)alkylheterocycle;

each $R^{22}$ is independently —H, -alkyl, -aryl, -heteroaryl, -cycloalkyl, -alkylaryl, or -alkylheteroaryl; and the other substituents are as described above.

Preferably:

m is 0;

W is —CH$_2$— or —C(O)—;

X is —C(H)— or

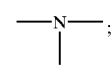

Z is —CH$_2$—;

$R^5$ is —OH;

$R^6$ is —H or —$R^{14}$;

$R^7$ is —C(O)alkyl;

$R^8$ is methyl, ethyl, n-propyl, isopropyl, cyclopentyl, phenethyl, or benzyl; or $R^9$ is —C(O)aryl, —C(O)heteroaryl, —C(O)alkylaryl, —C(O)alkylheteroaryl, -alkylaryl, -alkylheteroaryl, -aryl, or -heteroaryl;

Q is O;

$R^{14}$ is (i) substituted with —Oalkyl, —F or —Cl, or (ii) substituted with phenyl; or C is a benzo ring, wherein any hydrogen bound to the ring is optionally replaced with —$R^4$;

More preferably, $R^6$ is —H.

In any of the above embodiments, preferred forms of formula (I) are those wherein:

Z is —$CH_2$—, W is —C(O)— and X is —C(H)— (Ia);

Z is —$CH_2$—, W is —$CH_2$— and X is —C(H)— (Ib),

Z is —$CH_2$—, W is —C(O)— and X is

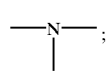 (Ic);

or

Z is —$CH_2$—, W is —$CH_2$— and X is

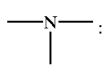 (Id)

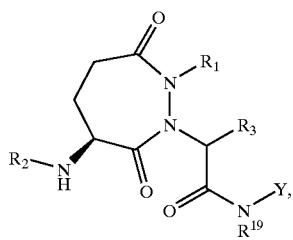 Ia

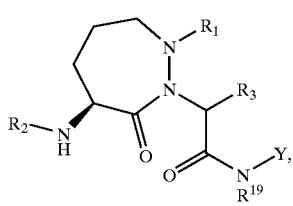 Ib

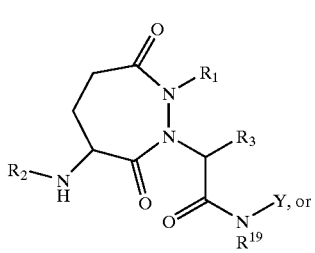 Ic

-continued

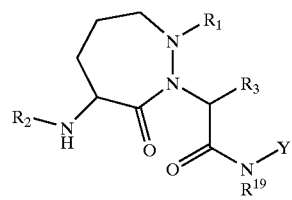 Id and the other substituents are as described above.

In any of the above embodiments, preferred forms of formula (II) are those wherein:

W is —C(O)— and X is —C(H)— (IIa),

W is —$CH_2$— and X is —C(H)— (IIb),

W is —C(O)— and X is

 (IIc)

or

W is —$CH_2$— and X is

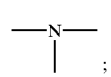 (IId)

and

C is a benzo ring, wherein any hydrogen bound to the ring is optionally substituted with —$R^4$:

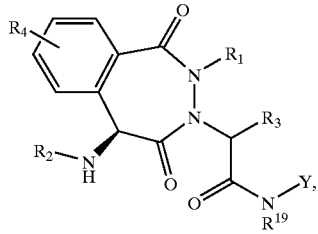 IIa

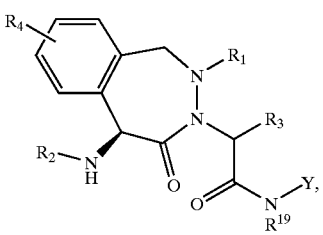 IIb

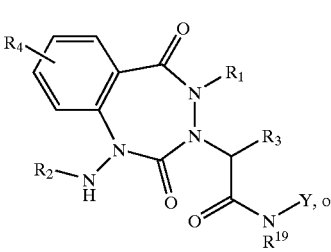 IIc

-continued

IId

[Structure IId: benzene ring with R4 substituent fused to a 7-membered ring containing CH2-N(R1)-C(=O)-N(CHR3-C(=O)-N(H)-Y)(-) with R2-N(H)- attached]

and the other substituents are as described above.

The compounds of a preferred embodiment (E) of this invention are those of formula (I):

(I)

[Structure I: 7-membered ring Z-W-N(R1)-N(CHR3-C(=O)-N(H)-Y)-C(=O)-X with R2-N(H)- attached to X]

where in:
Y is:

(a)

[Structure (a): -(CH2)m-CH(C(=O)R5)-CH(CH3)-C(=O)R6 type group with R5 and R6 substituents]

(b)

[Structure (b): lactone ring with HO and R6 substituents]

m is 0 or 1;
W is —CH$_2$—, —C(O)—, S(O)$_2$, or —S(O)—;
X is —C(H)—, —C(R$^8$)—, or

—N—
|

Z is —CH$_2$—, —O—, —S—, or —N(R$^1$)—, provided that if Z is —N(R$^1$)—, then W is —C(O)—, —S(O)$_2$—, or —S(O)—;
each R$^1$ is independently —H, —C(O)R$^8$, —S(O)$_2$R$^8$, —S(O)R$^8$, —R$^{21}$, -alkyl-R$^{21}$, -alkenyl-R$^{21}$, -alkynyl-R$^{21}$, -alkyl;
R$^2$ is —C(O)R$^8$, —C(O)C(O)R$^8$, —S(O)$_2$R$^8$, —S(O)R$^8$, —C(O)OR$^8$, —C(O)N(H)R$^8$, —S(O)$_2$N(H)—R$^8$, —S(O)N(H)—R$^8$, —C(O)C(O)N(H)R$^8$, —C(O)CH=CHR$^8$, —C(O)CH$_2$OR$^8$, —C(O)CH$_2$N(H)R$^8$, —C(O)N(R$^8$)$_2$, —S(O)$_2$N(R$^8$)$_2$, —S(O)N(R$^8$)$_2$, —C(O)C(O)N(R$^8$)$_2$, —C(O)CH$_2$N(R$^8$)$_2$, —CH$_2$—R$^8$, —CH$_2$-alkenyl-R$^8$, or —CH$_2$-alkynyl-R$^8$;
R$^3$ is —H, —R$^{21}$, -alkyl-R$^{21}$, -alkenyl-R$^{21}$, -alkynyl-R$^{21}$, alkyl, or an amino acid side chain;
each R$^4$ is independently —OH, —F, —Cl, —Br, —I, —NO$_2$, —CN, —NH$_2$, —CO$_2$H, —C(O)NH$_2$, —N(H)C(O)H, —N(H)C(O)NH$_2$, -alkyl, -cycloalkyl, -perfluoroalkyl, —O-alkyl, —N(H)alkyl, —N(alkyl)$_2$, —C(O)N(H)alkyl, —C(O)N(alkyl)$_2$, —N(H)C(O)alkyl, —N(H)C(O)N(H)alkyl, —N(H)C(O)N(alkyl)$_2$, —S-alkyl, —S(O)$_2$alkyl, —S(O)alkyl, —C(O)alkyl, —CH$_2$NH$_2$, —CH$_2$N(H)alkyl, —CH$_2$N(alkyl)$_2$, or —N(H)C(O)Oalkyl;
R$^5$ is —OH, —OR$^8$, —N(H)OH, or —N(H)SO$_2$R$^8$;
R$^6$ is —H, —CH$_2$OR$^9$, —CH$_2$SR$^{10}$, —CH$_2$N(H)R$^9$, —CH$_2$N(R$^9$)R$^{11}$, —C(H)N$_2$, —CH$_2$F, —CH$_2$Cl, —CH$_2$Br, —CH$_2$I, —C(O)N(R$^{11}$)$_2$, —R$^{13}$, or —R$^{14}$;
each R$^8$ is independently -alkyl, -cycloalkyl, -aryl, -heteroaryl, -heterocyclyl, -alkylcycloalkyl -alkylaryl, -alkylheteroaryl, or -alkylheterocyclyl;
R$^9$ is —H, —C(O)aryl, —C(O)heteroaryl, —C(O)alkylaryl, —C(O)alkylheteroaryl, -alkylaryl, -alkylheteroaryl, -aryl, -heteroaryl, or -P(O)(R$^{15}$)$_2$;
R$^{10}$ is -alkylaryl or -alkylheteroaryl;
each R$^{11}$ is independently —H, -alkyl, -aryl, -heteroaryl, -cycloalkyl, -alkylaryl, or -alkylheteroaryl;
R$^{13}$ is -alkylaryl or -alkylheteroaryl;
R$^{14}$ is (i)

[benzoxazole-2-yl structure with Q heteroatom]

(ii)

[oxazole-2-yl structure with Q]

(iii)

[1,3,4-oxadiazol-2-yl structure with Q], or (iv)

[1,3,4-oxadiazol-5-yl structure with Q]

wherein Q is —O— or —S—, any hydrogen atom in (i) is optionally replaced with —R$^{17}$, and any hydrogen atom in (ii), (iii), and (iv) is optionally replaced with —R$^{17}$, —R$^{18}$ or -alkyl-R$^{18}$;
each R$^{15}$ is independently —H, —OH, -alkyl, -aryl, -heteroaryl, -cycloalkyl, -alkylaryl, -alkylheteroaryl, —Oalkyl, —Oaryl, —Oheteroaryl, —Oalkylaryl, or —Oalkylheteroaryl;
each R$^{17}$ is independently —OH, —F, —Cl, —Br, —I, —NO$_2$, —CN, —NH$_2$, —CO$_2$H, —C(O)NH$_2$, —N(H)C(O)H, —N(H)C(O)NH$_2$, —SO$_2$NH$_2$, —C(O)H, -alkyl, -cycloalkyl, -perfluoroalkyl, —O-alkyl, —N(H)alkyl, —N(alkyl)$_2$, —$_{CO2}$alkyl, —C(O)N(H)alkyl, —C(O)N(alkyl)$_2$, —N(H)C(O)alkyl, —N(H)C(O)N(H)alkyl, —N(H)C(O)N(alkyl)$_2$, —S(O)$_2$N(H)alkyl, —S(O)N(H)alkyl, —S(O)$_2$N(alkyl)$_2$, —S(O)N(alkyl)$_2$, —S-alkyl, —S(O)$_2$alkyl, —S(O)alkyl, or —C(O)alkyl;
each R$^{18}$ is independently -aryl, -heteroaryl, -alkylaryl, -alkylheteroaryl, —O-aryl, —O-heteroaryl, —O-alkylaryl, —O-alkylheteroaryl, —N(H)aryl, —N(aryl)$_2$, —N(H)heteroaryl, —N(heteroaryl)$_2$, —N(H)alkylaryl, —N(alkylaryl)$_2$, —N(H)alkylheteroaryl, —N(alkylheteroaryl)$_2$, —S-aryl, —S-heteroaryl, —S-alkylaryl, —S-alkylheteroaryl, —C(O)aryl, —C(O)heteroaryl, —C(O)alkylaryl, —C(O)alkylheteroaryl, —CO$_2$aryl, —CO$_2$heteroaryl, —CO$_2$alkylaryl, —CO$_2$alkylheteroaryl, —C(O)N(H)aryl, —C(O)N(aryl)$_2$, —C(O)N(H)heteroaryl, —C(O)N(heteroaryl)$_2$, —C(O)N(H)alkylaryl), —C(O)N(alkylaryl)$_2$, —C(O)N(H)alkylheteroaryl, —C(O)N(alkylheteroaryl)$_2$, —S(O)$_2$-aryl, —S(O)-aryl, —S(O)$_2$-heteroaryl, —S(O)-heteroaryl, —S(O)$_2$-alkylaryl, —S(O)-alkylaryl, —S(O)$_2$-alkylheteroaryl, —S(O)-alkylheteroaryl, —S(O)$_2$N(H)-aryl, —S(O)N(H)-aryl, —S(O)$_2$NH-heteroaryl, —S(O)NH-heteroaryl, —S(O)$_2$N(H)-alkylaryl, —S(O)N(H)-alkylaryl, —S(O)$_2$N(H)-alkylheteroaryl, —S(O)N(H)-alkylheteroaryl, —S(O)$_2$N(aryl)$_2$, —S(O)N(aryl)$_2$, —S(O)$_2$N(heteroaryl)$_2$, —S(O)N(heteroaryl)$_2$, —S(O)$_2$N(alkylaryl)$_2$, —S(O)N(alkylaryl)$_2$, —S(O)$_2$N(alkylheteroaryl)$_2$, —S(O)N(alkylheteroaryl)$_2$, —N(H)C(O)N(H)aryl, —N(H)C(O)N(H)heteroaryl, —N(H)C(O)N(H)alkylaryl, —N(H)C(O)N(H)alkylheteroaryl, —N(H)C(O)N(aryl)$_2$, —N(H)C(O)N(heteroaryl)$_2$, —N(H)C(O)N(alkylaryl)$_2$, or —N(H)C(O)N(alkylheteroaryl)$_2$; and each $R^{21}$ is independently -aryl, -heteroaryl, cycloalkyl, or -heterocyclyl, wherein a hydrogen atom bound to any carbon atom is optionally replaced by $R^4$ and a hydrogen atom bound to any nitrogen atom is optionally replaced by $R^2$.

The compounds of a another preferred embodiment (F) of this invention are those of formula (II):

wherein:

C is an aryl or heteroaryl ring, wherein any hydrogen atom bound to the C ring is optionally substituted with —$R^4$; and the other substituents are as described above in embodiment (E).

The compounds of two other embodiments (G) and (H) of this invention are those of formulae (I) or (II), respectively, wherein: Y is (c), (d), (e), or (f):

$R^7$ is —C(O)alkyl, —C(O)cycloalkyl, —C(O)alkyenyl, —C(O)alkylaryl, —C(O)alkylheteroaryl, —C(O)heterocycle, or —C(O)alkylheterocycle; and the other substituents are as described above.

Preferably:

m is 0;

W is —CH$_2$— or —C(O)—;

X is —C(H)— or $$-N-\ ;$$

Z is —CH$_2$—;

$R^5$ is —OH;

$R^6$ is —H, —$R^{14}$, —CH$_2$OR$^9$ or —CH$_2$F;

$R^7$ is —C(O)alkyl;

$R^8$ is methyl, ethyl, n-propyl, isopropyl, cyclopentyl, phenethyl, or benzyl;

$R^9$ is —C(O)aryl, —C(O)heteroaryl, —C(O)alkylaryl, —C(O)alkylheteroaryl, -alkylaryl, -alkylheteroaryl, -aryl, or -heteroaryl;

Q is O;

$R^{14}$ is (i) substituted with —Oalkyl, —F or —Cl, or (ii) substituted with phenyl;

C is a benzo ring, wherein any hydrogen bound to the ring is optionally replaced with —$R^4$;

$R^1$ is aryl, heteroaryl, alkyl, alkylaryl, or alkylheteroaryl; or $R^3$ is an amino acid side chain, aryl, heteroaryl, alkyl, alkylaryl, or alkylheteroaryl.

$R^1$ is;

More preferably,
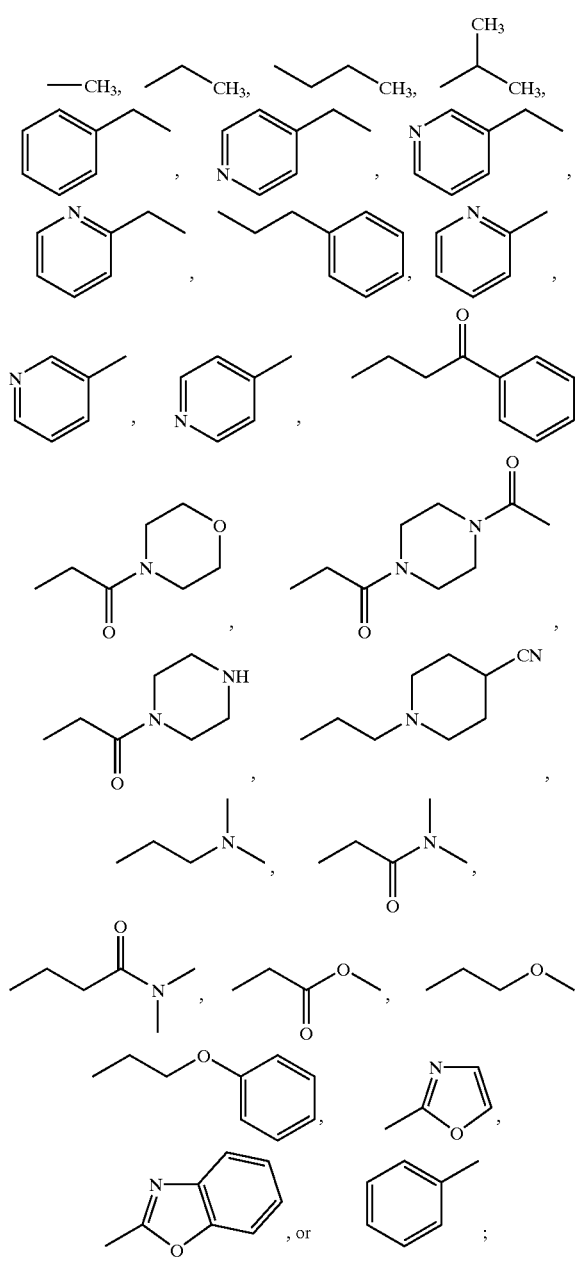
$R^2$ is:
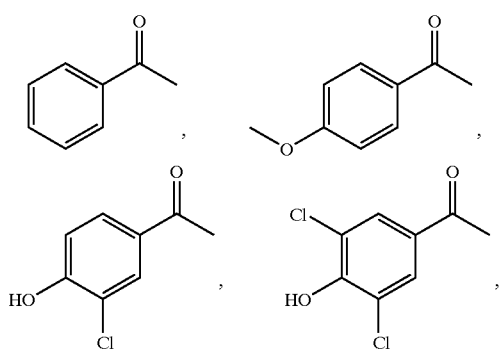
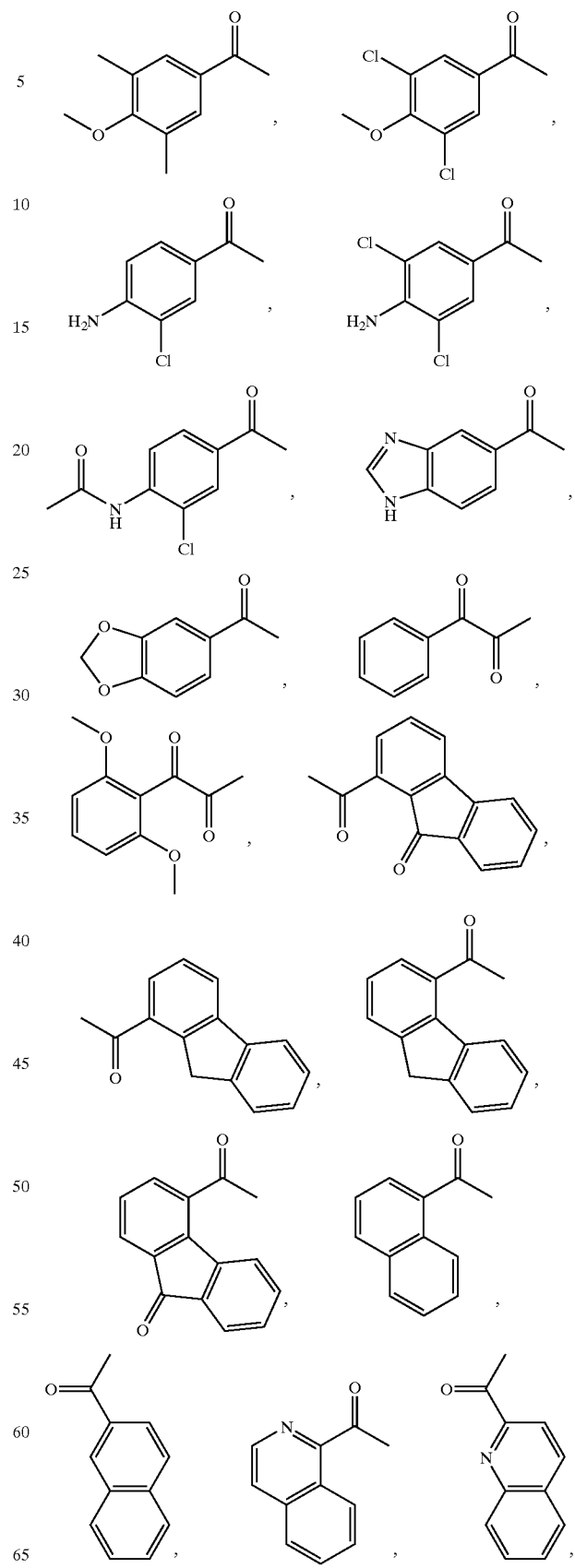

-continued
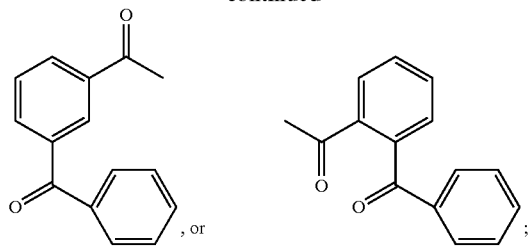, or ;
$R^3$ is:
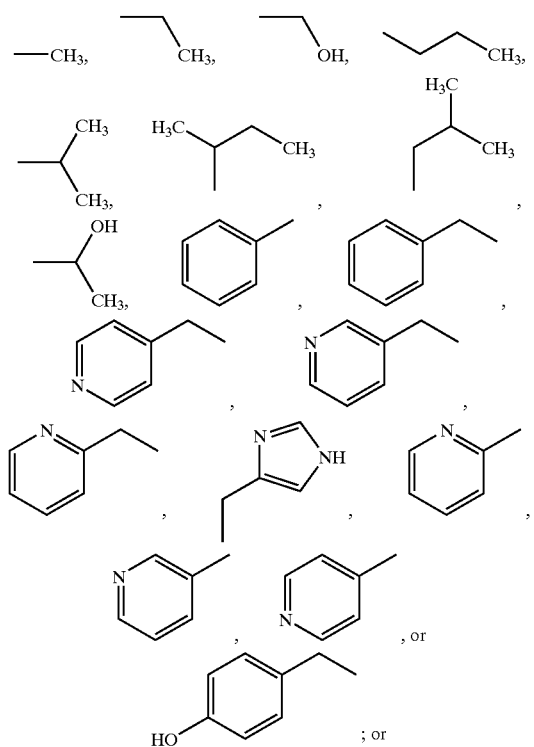
; or
$R^6$ is —H.
In embodiments (C), (D), (G), or (H) Y is:
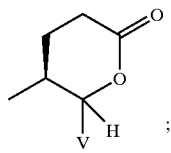
and V is preferably:
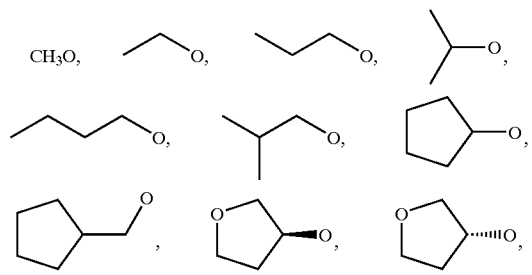
-continued
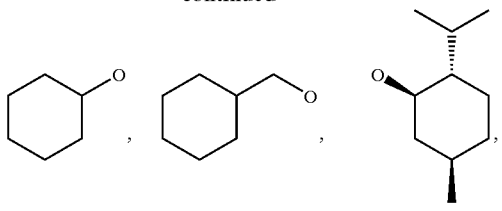
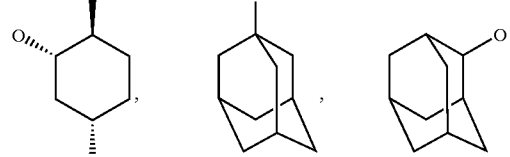
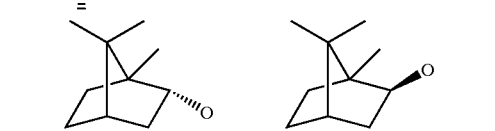
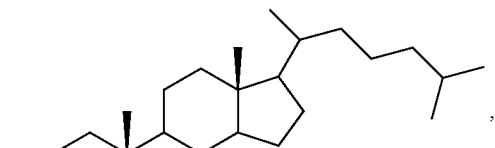
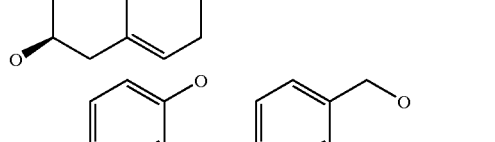
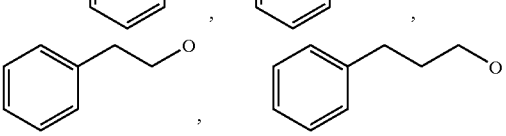
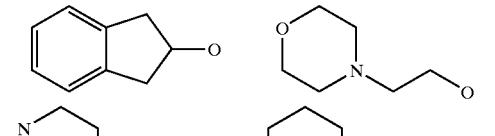
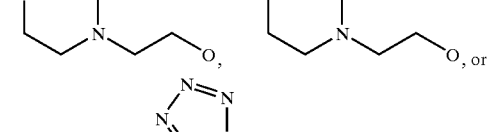
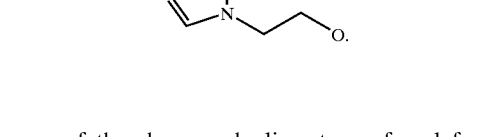
In any of the above embodiments, preferred forms of formula (I) are those wherein:
Z is —CH$_2$—, W is —C(O)— and X is —C(H)— (Ia);
Z is —CH$_2$—, W is —CH$_2$— and X is —C(H)— (Ib),
Z is —CH$_2$—, W is —C(O)— and X is
$$\overset{\displaystyle |}{\underset{\displaystyle |}{-\mathrm{N}-}} \quad \text{(Ic)}$$
;
or Z is —CH$_2$—, W is —CH$_2$— and X is

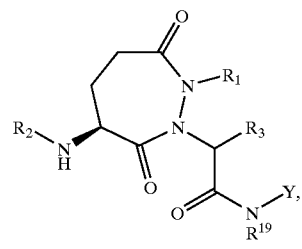
Ia

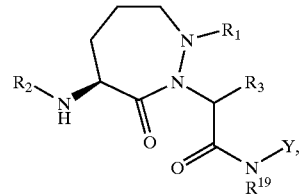
Ib

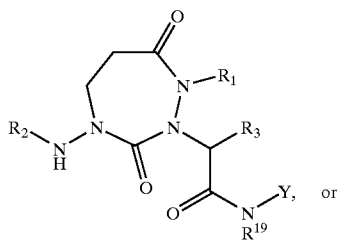
Ic

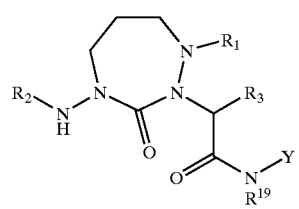
Id and the other substituents are as described above.

More preferred forms of formula (I) are as follows:

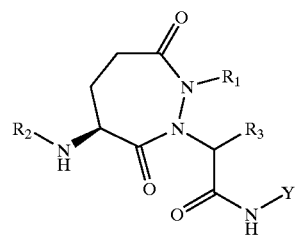
Ie

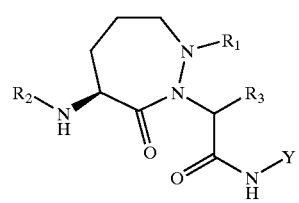
If

In any of the above embodiments, preferred forms of formula (II) are those wherein:

W is —C(O)— and X is —C(H)— (IIa),
W is —CH$_2$— and X is —C(H)— (IIb),

W is —C(O)— and X is

(IIc)

or
W is —CH$_2$— and X is

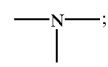
(IId)

and

C is a benzo ring, wherein any hydrogen bound to the ring is optionally substituted with —R$^4$:

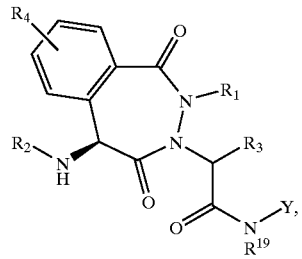
IIa

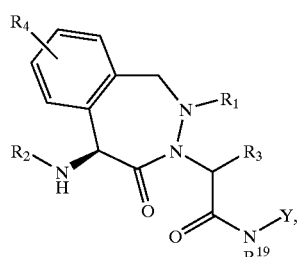
IIb

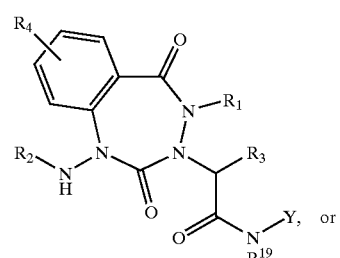
IIc

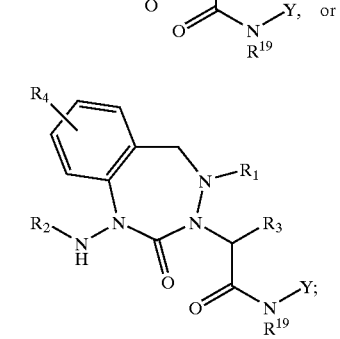
IId and the other substituents are as described above.

Specific compounds of this invention include, but are not limited to:

11a 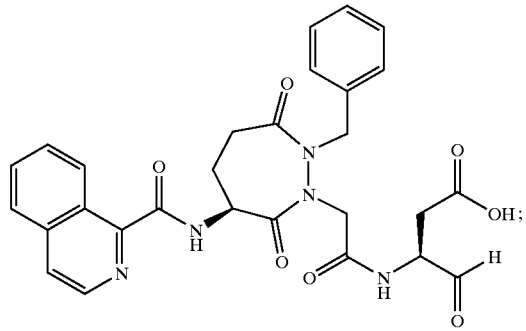

10a 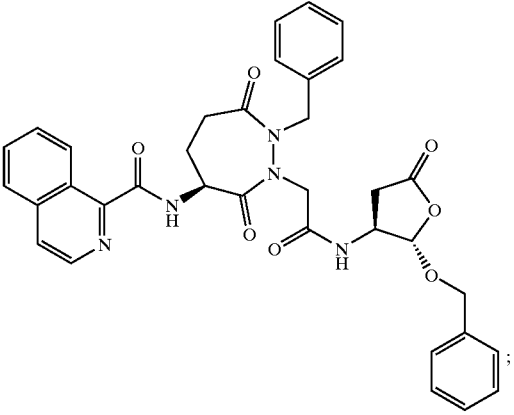

11b 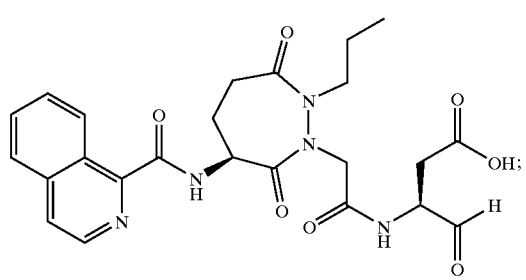

10b 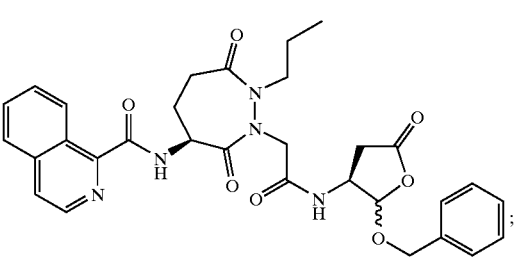

11c 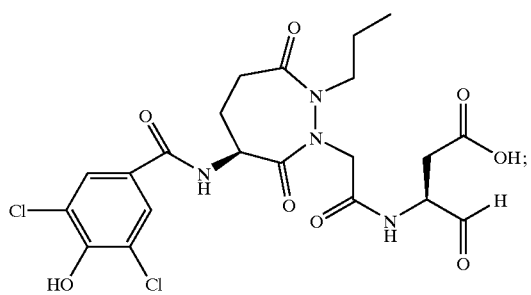

19 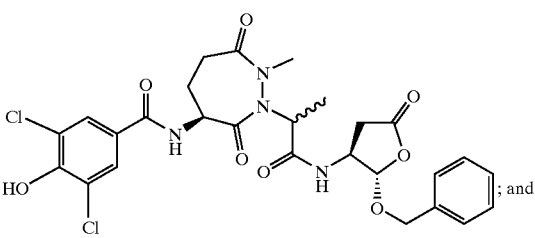

; and

20 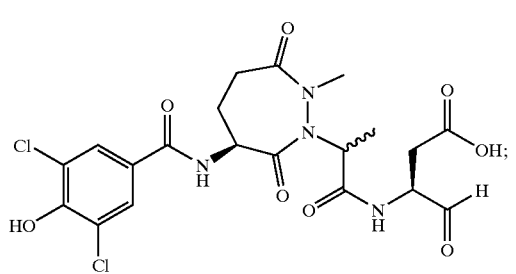

26b 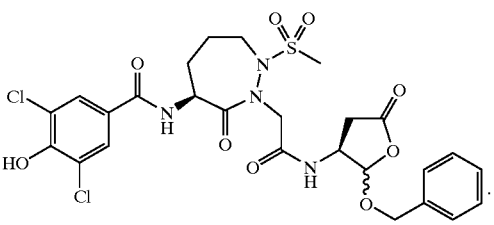

27 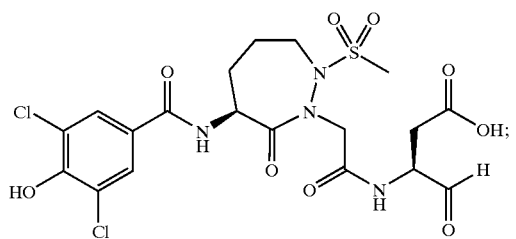

The compounds of this invention may contain one or more "asymmetric" carbon atoms and thus may occur as racemates and racemic mixtures, single enantiomers, diastereomeric mixtures and individual diastereomers. Each stereogenic carbon may be of the R or S configuration. Although specific compounds and scaffolds exemplified in this application may be depicted in a particular stereochemical configuration, compounds and scaffolds having either the opposite stereochemistry at any given chiral center or mixtures thereof are also envisioned.

All such isomeric forms of these compounds are expressly included in the present invention, as well as pharmaceutically acceptable derivative thereof.

The term "pharmaceutically acceptable derivative" means any pharmaceutically acceptable salt, ester, or salt of such ester, of a compound of this invention or any other compound which, upon administration to a recipient, is capable of providing (directly or indirectly) a compound of this invention or an anti-ICE active metabolite or residue thereof.

Pharmaceutically acceptable salts of the compounds of this invention include, for example, those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N—$(C_{1-4}$ alkyl$)_4^+$ salts.

This invention also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

When multiply substituted, each substituent may be picked independently of any other substituent as long as the combination of substituents results in the formation of a stable compound.

Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40° C. or less, in the presence or absence of moisture or other chemically reactive conditions, for at least a week.

Preferred compounds of this invention may be readily absorbed by the bloodstream of patients upon oral administration. This oral availability makes such compounds excellent agents for orally-administered treatment and prevention regimens against IL-1-, apoptosis-, IGIF-, or IFN-γ-mediated diseases.

It should be understood that the compounds of this invention may exist in various equilibrium forms, depending on conditions including choice of solvent, pH, and others known to the practitioner skilled in the art. All such forms of these compounds are expressly included in the present invention. In particular, many of the compounds of this invention, especially those which contain aldehyde or ketone groups and carboxylic acid groups in Y, may take hemi-acetal or hemi-ketal or hydrated forms. For example, compounds of embodiment (A) are in a hemi-acetal or hemi-ketal form when Y is:

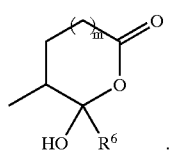

Depending on the choice of solvent and other conditions known to the practitioner skilled in the art, compounds of this invention may also take hydrated, acyloxy ketal, acyloxy acetal, ketal, acetal or enol forms. For example, compounds of this invention are in hydrated forms when Y is:

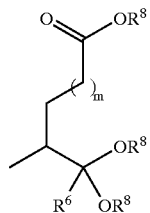

acyloxy ketal or acyloxy acetal forms when Y is:

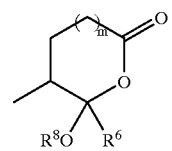

ketal or acetal forms when Y is:

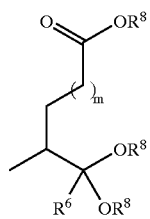

and enol forms when Y is:

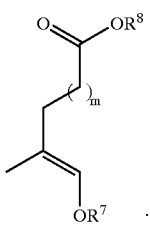

In addition, it should be understood that the equilibrium forms of the compounds of this invention may include tautomeric forms. All such forms of these compounds are expressly included in the present invention.

The compounds of formulae (I) and (II) may be synthesized using conventional techniques. Advantageously, these compounds are conveniently synthesized from readily available starting materials.

The compounds of this invention are among the most readily synthesized caspase inhibitors known. Many of the previously described caspase or ICE inhibitors contain four or more chiral centers and numerous peptide linkages. The relative ease with which the compounds of this invention can be synthesized represents an advantage in the large scale production of these compounds.

For example, compounds of this invention may be prepared using the processes described herein. As can be appreciated by the skilled practitioner, these processes are not the only means by which the compounds described and claimed in this application may be synthesized. Further methods will be evident to those of ordinary skill in the art.

Additionally, the various synthetic steps described herein may be performed in an alternate sequence or order to give the desired compounds.

It should be understood that the compounds of this invention may be modified by appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion. In addition, the compounds may be altered to pro-drug form such that the desired compound is created in the body of the patient as the result of the action of metabolic or other biochemical processes on the pro-drug. Such pro-drug forms typically demonstrate little or no activity in in vitro assays. Some examples of pro-drug forms include ketal, acetal, oxime, imine and hydrazone forms of compounds which contain ketone or aldehyde groups, especially where they occur in the Y group of the compounds of this invention. Other examples of pro-drug forms include the hemi-ketal, hemi-acetal, acyloxy ketal, acyloxy acetal, ketal, acetal and enol forms that are described herein.

Compositions and Methods

The compounds of this invention are caspase inhibitors, particularly ICE inhibitors. Accordingly, these compounds are capable of targeting and inhibiting events in IL-1-, apoptosis-, IGIF-, and IFN-γ-mediated diseases, and, thus, the ultimate activity of that protein in inflammatory diseases, autoimmune diseases, destructive bone, proliferative disorders, infectious diseases, and degenerative diseases. For example, the compounds of this invention inhibit the conversion of precursor IL-1β to mature IL-1β by inhibiting ICE. Because ICE is essential for the production of mature IL-1, inhibition of that enzyme effectively blocks initiation of IL-1-mediated physiological effects and symptoms, such as inflammation, by inhibiting the production of mature IL-1. Thus, by inhibiting IL-1β precursor activity, the compounds of this invention effectively function as IL-1 inhibitors.

Compounds of this invention also inhibit conversion of pro-IGIF into active, mature IGIF by inhibiting ICE. Because ICE is essential for the production of mature IGIF, inhibition of ICE effectively blocks initiation of IGIF-mediated physiological effects and symptoms, by inhibiting production of mature IGIF. IGIF is in turn essential for the production of IFN-γ. ICE therefore effectively blocks initiation of IFN-γ-mediated physiological effects and symptoms, by inhibiting production of mature IGIF and thus production of IFN-γ.

The pharmaceutical compositions and methods of this invention, therefore, will be useful for controlling caspase activity in vivo. The compositions and methods of this invention will thus be useful for controlling IL-1, IGIF or IFN-γ levels in vivo and for treating or reducing the advancement, severity or effects of IL-1-, apoptosis-, IGIF-, or IFN-γ-mediated conditions, including diseases, disorders or effects.

Pharmaceutical compositions of this invention comprise a compound of formulae (I) or (II) or a pharmaceutically acceptable salt thereof and a is pharmaceutically acceptable carrier. Such compositions may optionally comprise an additional therapeutic agent. Such agents include, but are not limited to, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The term "pharmaceutically acceptable carrier" refers to a non-toxic carrier that may be administered to a patient, together with a compound of this invention, and which does not destroy the pharmacological activity thereof.

Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, wool fat and self-emulsifying drug delivery systems (SEDDS) such as α-tocopherol, polyethyleneglycol 1000 succinate, or other similar polymeric delivery matrices.

In pharmaceutical composition comprising only a compound of formulae (I) or (II) as the active component, methods for administering these compositions may additionally comprise the step of administering to the subject an additional agent. Such agents include, but are not limited to, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The term "pharmaceutically effective amount" refers to an amount effective in treating or ameliorating an IL-1-, apoptosis-, IGIF- or IFN-γ-mediated disease in a patient. The term "prophylactically effective amount" refers to an amount effective in preventing or substantially lessening IL-1-, apoptosis-, IGIF- or IFN-γ-mediated diseases in a patient.

The compounds of this invention may be employed in a conventional manner for controlling IGIF and IFN-γ levels in vivo and for treating diseases or reducing the advancement or severity of effects which are mediated by IL-1, apoptosis, IGIF or IFN-γ. Such methods of treatment, their dosage levels and requirements may be selected by those of ordinary skill in the art from available methods and techniques.

For example, a compound of this invention may be combined with a pharmaceutically acceptable adjuvant for administration to a patient suffering from an IL-1-, apoptosis-, IGIF- or IFN-γ-mediated disease in a pharmaceutically acceptable manner and in an amount effective to lessen the severity of that disease.

Alternatively, the compounds of this invention may be used in compositions and methods for treating or protecting individuals against IL-1, apoptosis-, IGIF, or IFN-γ mediated diseases over extended periods of time. The compounds may be employed in such compositions either alone or together with other compounds of this invention in a manner consistent with the conventional utilization of enzyme inhibitors in pharmaceutical compositions. For example, a compound of this invention may be combined with pharmaceutically acceptable adjuvants conventionally employed in vaccines and administered in prophylactically effective amounts to protect individuals over an extended period of time against IL-1-, apoptosis-, IGIF, or IFN-γ mediated diseases.

The compounds of formulae (I) or (II) may also be co-administered with other caspase or ICE inhibitors to increase the effect of therapy or prophylaxis against various IL-1-, apoptosis-, IGIF- or IFN-γ mediated diseases.

In addition, the compounds of this invention may be used in combination either conventional anti-inflammatory agents or with matrix metalloprotease inhibitors, lipoxygenase inhibitors and antagonists of cytokines other than IL-1β.

The compounds of this invention can also be administered in combination with immunomodulators (e.g., bropirimine, anti-human alpha-interferon antibody, IL-2, GM-CSF, methionine enkephalin, interferon-alpha, diethyldithiocarbamate, tumor necrosis factor, naltrexone and EPO), with prostaglandins, or with antiviral agents (e.g., 3TC, polysulfated polysaccharides, ganiclovir, ribavirin, acyclovir, alpha interferon, trimethotrexate and fancyclovir) or prodrugs of these or related compounds to prevent or combat IL-1-mediated disease symptoms such as inflammation.

When the compounds of this invention are administered in combination therapies with other agents, they may be administered sequentially or concurrently to the patient. Alternatively, pharmaceutical or prophylactic compositions according to this invention comprise a combination of a compound of formula (I) or is (II) and another therapeutic or prophylactic agent.

The pharmaceutical compositions of this invention may be administered orally, parenterally, by inhalation spray, topically, rectally, nasally, buccally, vaginally or via an implanted reservoir. We prefer oral administration. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension.

This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as those described in Pharmacopeia Helvetica, or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-administered transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of IL-1-, apoptosis-, IGIF-, and IFN-γ mediated diseases, including inflammatory diseases, autoimmune diseases, destructive bone disorders, proliferative disorders, infectious diseases, degenerative diseases, necrotic diseases, inflammatory peritonitis, osteoarthritis, acute pancreatitis, chronic pancreatitis, asthma, adult respiratory distress syndrome, glomerulonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, inflammatory bowel disease, Crohn's disease, psoriasis, graft vs. host disease, osteoporosis, multiple myeloma-related bone disorder, acute myelogenous leukemia, chronic myelogenous leukemia, metastatic melanoma, Kaposi's sarcoma, multiple myeloma, sepsis, septic shock, Shigellosis, Alzheimer's disease, Parkinson's disease, cerebral ischemia, myocardial ischemia, spinal muscular atrophy, multiple sclerosis, AIDS-related encephalitis, HIV-related encephalitis, aging, alopecia, neurological damage due to stroke, ulcerative colitis, traumatic brain injury, organ transplant rejection, infectious hepatitis, juvenile diabetes, lichenplanus, acute dermatomyositis, eczema, primary cirrhosis, uveitis, Behcet's disease, atopic skin disease, pure red cell aplasia, aplastic anemia, amyotrophic lateral sclerosis, nephrotic syndrome and systemic diseases or diseases with effects localized in the liver or other organs having an inflammatory or apoptotic component caused by excess dietary alcohol intake or viruses, such as HBV, HCV, HGV, yellow fever virus, dengue fever virus, and Japanese encephalitis virus.

Typically, the pharmaceutical compositions of this invention will be administered from about 1 to 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formulae (I) or (II) and one or more additional therapeutic or prophylactic agents, both the compound and the additional agent should be present at dosage levels of between about 10% to 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

IL-1 or apoptosis mediated diseases may be treated or prevented by the compounds of this invention. Such diseases include, but are not limited to, inflammatory diseases, autoimmune diseases, destructive bone disorders, proliferative disorders, infectious diseases, and degenerative diseases.

The IL-1 or apoptosis mediated inflammatory diseases which may be treated or prevented include, but are not limited to osteoarthritis, acute pancreatitis, chronic pancreatitis, asthma, inflammatory peritonitis, and adult respiratory distress syndrome. Preferably the inflammatory disease is osteoarthritis or acute pancreatitis.

The IL-1 or apoptosis mediated autoimmune diseases which may be treated or prevented include, but are not limited to, glomerulonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, multiple sclerosis, inflammatory bowel disease, Crohn's disease, psoriasis, and graft vs. host disease. Preferably the autoimmune disease is rheumatoid arthritis, inflammatory bowel disease, Crohn's disease, or psoriasis.

IL-1 or apoptosis mediated destructive bone disorders which may be treated or prevented include, but are not limited to, osteoporosis and multiple myeloma-related bone disorder.

The IL-1 or apoptosis mediated proliferative diseases which may be treated or prevented include, but are not limited to, acute myelogenous leukemia, chronic myelogenous leukemia, metastatic melanoma, Kaposi's sarcoma, and multiple myeloma.

The IL-1 or apoptosis mediated infectious diseases which may be treated or prevented include, but are not limited to, sepsis, septic shock, and Shigellosis.

The IL-1 or apoptosis mediated degenerative or necrotic diseases which may be treated or prevented by the compounds of this invention include, but are not limited to, Alzheimer's disease, Parkinson's disease, cerebral ischemia, and myocardial ischemia. Preferably, the degenerative disease is Alzheimer's disease.

The IL-1 or apoptosis mediated degenerative diseases which may be treated or prevented by the compounds of this invention include, but are not limited to, Alzheimer's disease, Parkinson's disease, cerebral ischemia, myocardial ischemia, spinal muscular atrophy, multiple sclerosis, AIDS-related encephalitis, HIV-related encephalitis, aging, alopecia, and neurological damage due to stroke.

Other diseases having an inflammatory or apoptotic component may be treated or prevented by the compounds of this invention. Such diseases may be systemic diseases or diseases with effects localized in the liver or other organs and may be caused by, for example, excess dietary alcohol intake or viruses, such as HBV, HCV, HGV, yellow fever virus, dengue fever virus, and Japanese encephalitis virus.

IGIF- or IFN-γ-mediated diseases may also be treated or prevented by the compounds of this invention. Such diseases include, but are not limited to, inflammatory, infectious, autoimmune, proliferative, neurodegenerative and necrotic conditions. The IGIF- or IFN-γ-mediated inflammatory diseases which may be treated or prevented include, but are not limited to osteoarthritis, acute pancreatitis, chronic pancreatitis, asthma, rheumatoid arthritis, inflammatory bowel disease, Crohn's disease, ulcerative colitis, cerebral ischemia, myocardial ischemia and adult respiratory distress syndrome. Preferably, the inflammatory disease is rheumatoid arthritis, ulcerative colitis, Crohn's disease, hepatitis or adult respiratory distress syndrome.

The IGIF- or IFN-γ-mediated infectious diseases which may be treated or prevented include, but are not limited to infectious hepatitis, sepsis, septic shock and Shigellosis.

The IGIF- or IFN-γ-mediated autoimmune diseases which may be treated or prevented include, but are not limited to glomerulonephritis, systemic lupus erythematosus, scleroderma, chronic thyroiditis, Graves' disease, autoimmune gastritis, insulin-dependent diabetes mellitus (Type I), juvenile diabetes, autoimmune hemolytic anemia, autoimmune neutropenia, thrombocytopenia, myasthenia gravis, multiple sclerosis, psoriasis, lichenplanus, graft vs. host disease, acute dermatomyositis, eczema, primary cirrhosis, hepatitis, uveitis, Behcet's disease, atopic skin disease, pure red cell aplasia, aplastic anemia, amyotrophic lateral sclerosis and nephrotic syndrome. Preferably, the autoimmune disease is glomerulonephritis, insulin-dependent diabetes mellitus (Type I), juvenile diabetes, psoriasis, graft vs. host disease, or hepatitis.

More preferred diseases which may be treated or prevented by the compounds of this invention include rheumatoid arthritis, inflammatory bowel disease, including Crohn's disease and ulcerative colitis, inflammatory peritonitis, septic shock, pancreatitis, traumatic brain injury, organ transplant rejection, osteoarthritis, and asthma.

Accordingly, one embodiment of this invention provides a method for treating or preventing an IL-1 or apoptosis mediated disease in a subject comprising the step of administering to the subject any compound, pharmaceutical composition, or combination described herein and a pharmaceutically acceptable carrier.

Another embodiment of this invention provides a method for decreasing IGIF production in a subject comprising the step of administering to the subject any compound, pharmaceutical composition, or combination described herein and a pharmaceutically acceptable carrier.

Another embodiment of this invention provides a method for decreasing IFN-γ production in a subject comprising the step of administering to the subject any compound, pharmaceutical composition, or combination described herein and a pharmaceutically acceptable carrier.

Although this invention focuses on the use of the compounds disclosed herein for preventing and treating IL-1, apoptosis-, IGIF, and IFN-γ-mediated diseases, the compounds of this invention can also be used as inhibitory agents for other cysteine proteases.

The compounds of this invention are also useful as commercial reagents which effectively bind to caspases or other cysteine proteases including, but not limited to ICE. As commercial reagents, the compounds of this invention, and their derivatives, may be used to block proteolysis of a target peptide in biochemical or cellular assays for ICE and ICE homologs or may be derivatized to bind to a stable resin as a tethered substrate for affinity chromatography applications. These and other uses which characterize commercial cysteine protease inhibitors will be evident to those of ordinary skill in the art.

In order that this invention be more fully understood, the following examples are set forth. These examples are for the purpose of illustration only and are not to be construed as limiting the scope of the invention in any way.

GENERAL METHODS

The compounds of this invention may be evaluated in various biological assays, including those described in Examples 2–4.

Other assays that may be used to evaluate the compounds of this invention are disclosed in PCT application PCT/US96/20843, published Jun. 26, 1997, under publication no. WO 97/22619, which is incorporated herein by reference. Such assays include in vivo bioavailability determinations, pharmacokinetic studies in the mouse, inhibition of ICE homologs, inhibition of apoptosis, in vivo acute assay for anti-inflammatory efficacy, measurement of blood levels, IGIF assays, mouse carrageenan peritoneal inflammation assay, and type II collagen-induced arthritis.

EXAMPLE 1

Compounds of this invention may be prepared according to published procedures, such as the procedures described in Robl, J. A. et al., *Bioorg. Med. Chem. Lett.* 4, pp. 2055–2060 (1994) or U.S. Pat. No. 4,465,679, which are incorporated herein by reference. Skilled practitioners will realize that such procedures may be modified to obtain the compounds of this invention.

For example, compounds represented by formulae (Ia) or (Ib) may be prepared as described in Scheme 1.

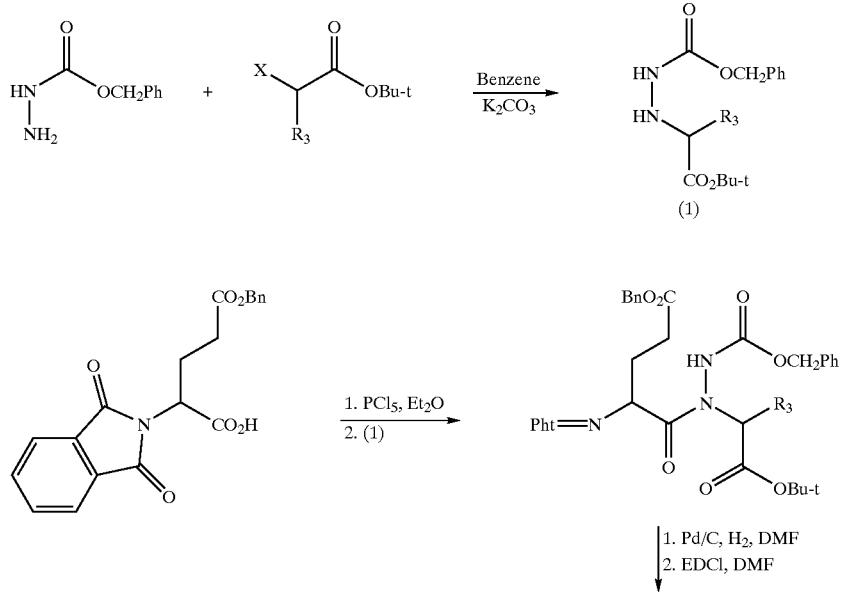

Scheme 1. Synthesis of analogs of Embodiment Ia and Ib

-continued
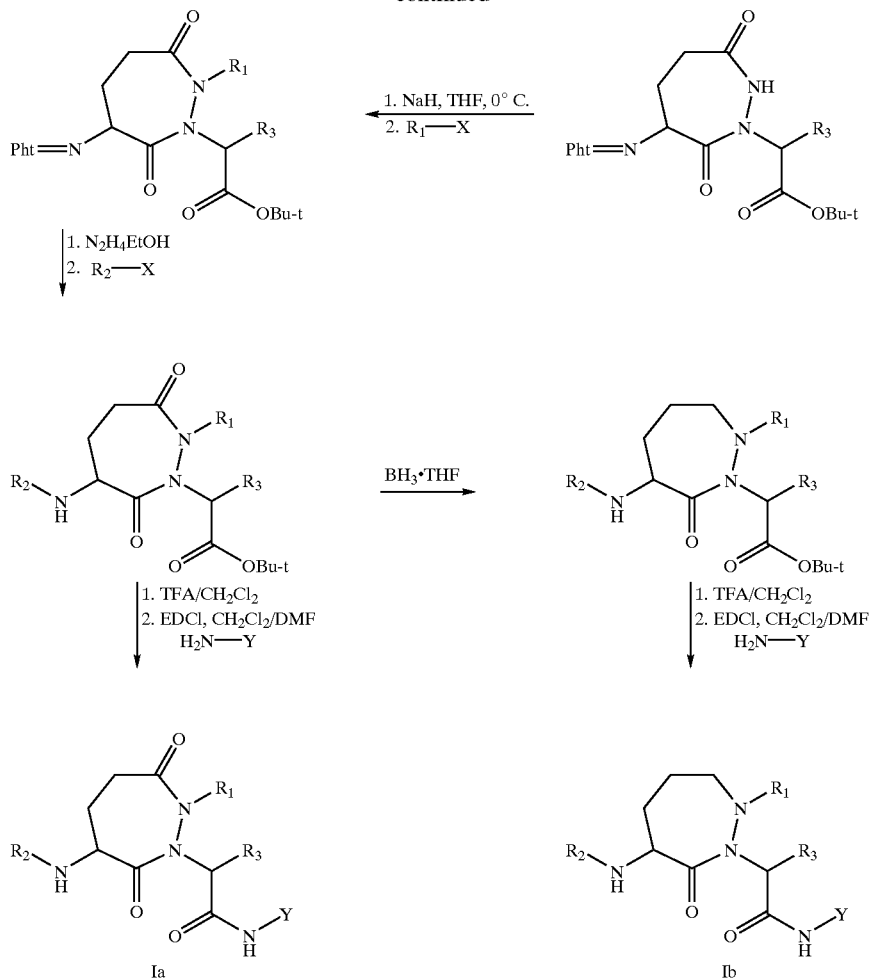
For example, compounds represented by formulae (Ic) or (Id) may be prepared as described in Scheme 2.
Scheme 2. Synthesis of analogs of Embodiment Ic and Id
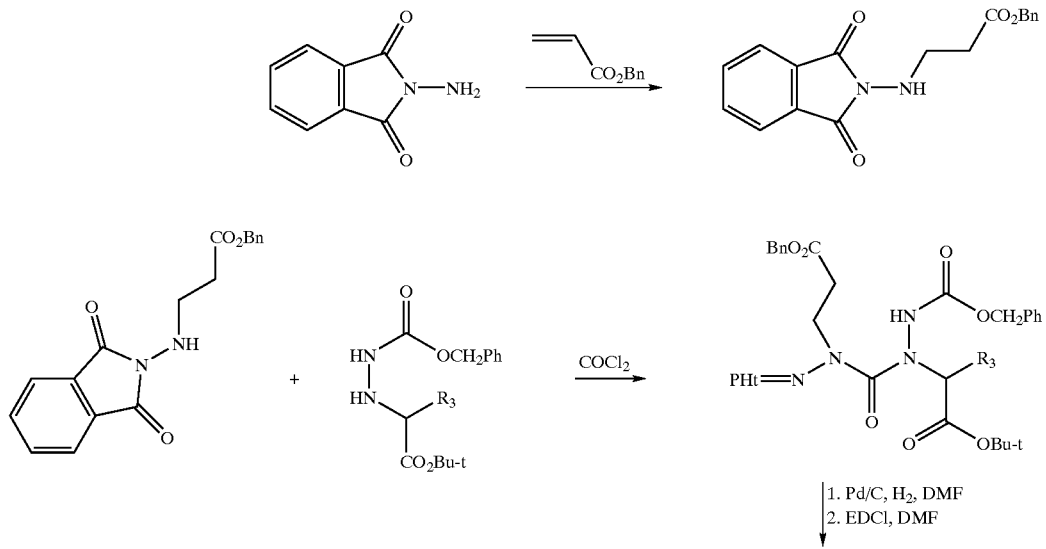

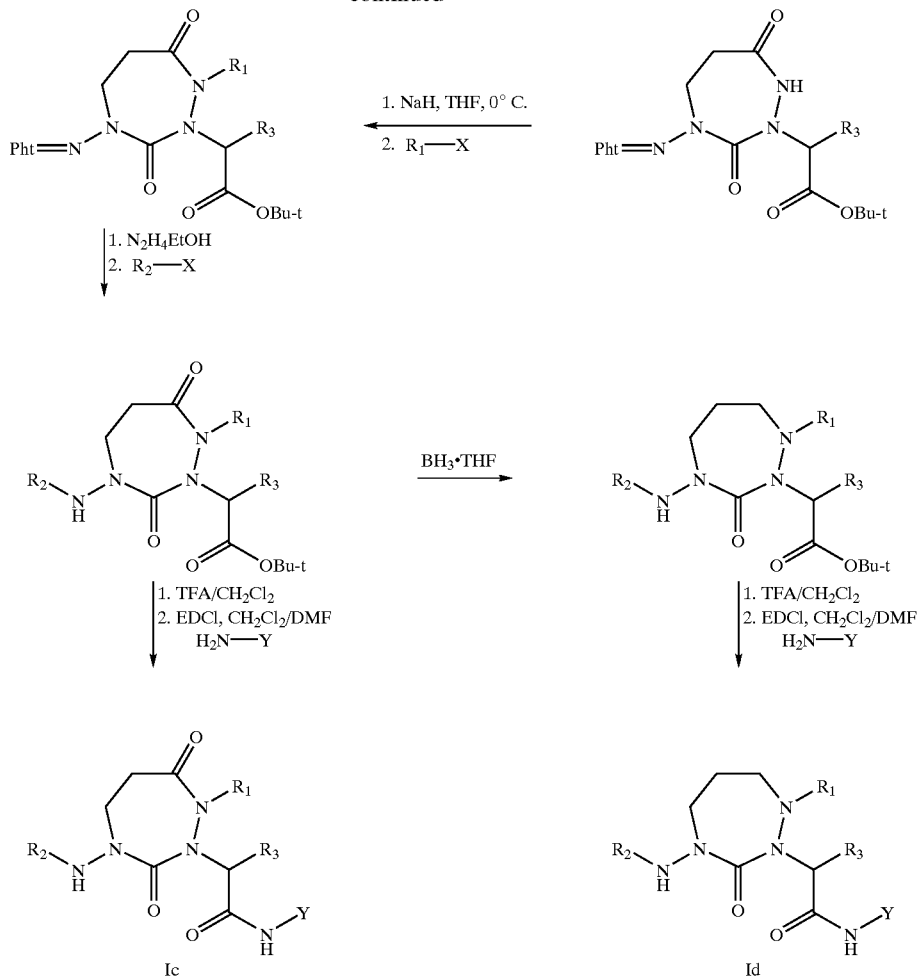
For example, compounds represented by formulae (IIa) or (IIb) may be prepared as described in Scheme 3.
Scheme 3. Synthesis of Embodiments IIa and IIb
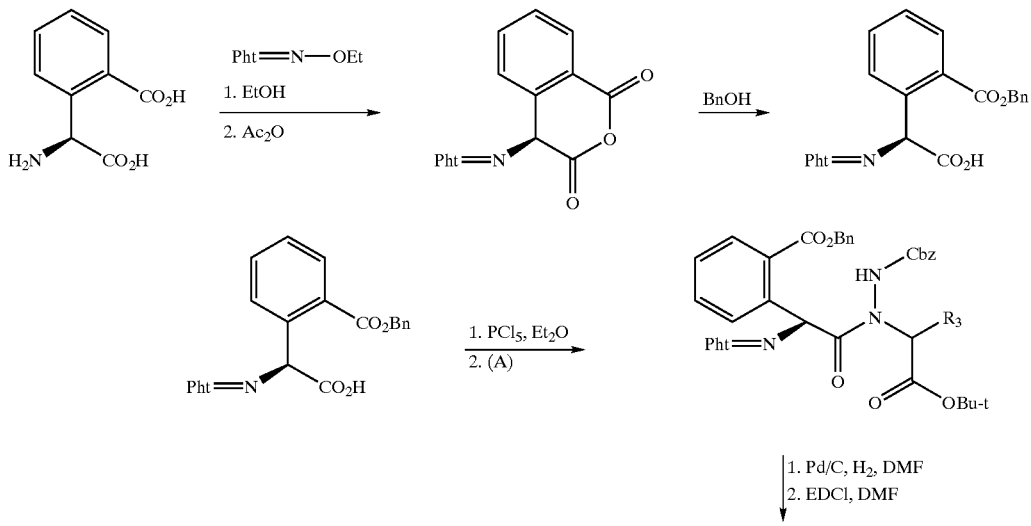

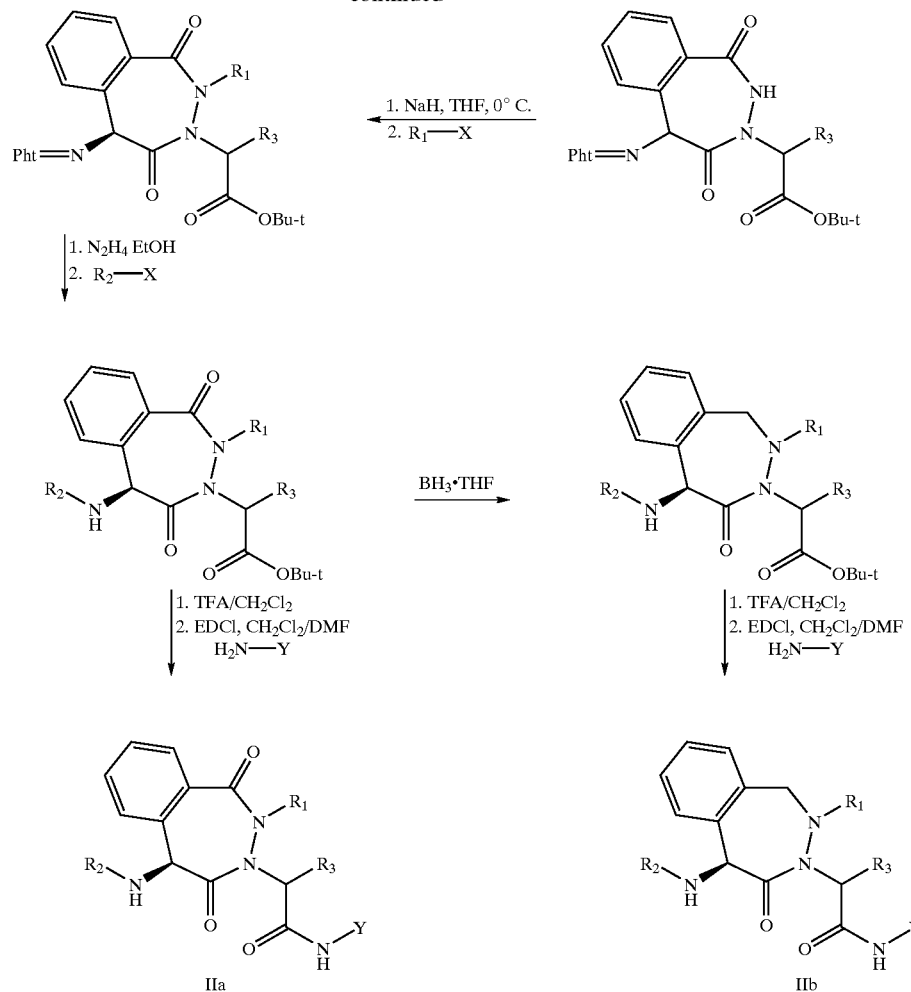
For example, compounds represented by formulae (IIc) or (IId) may be prepared as described in Scheme 4:
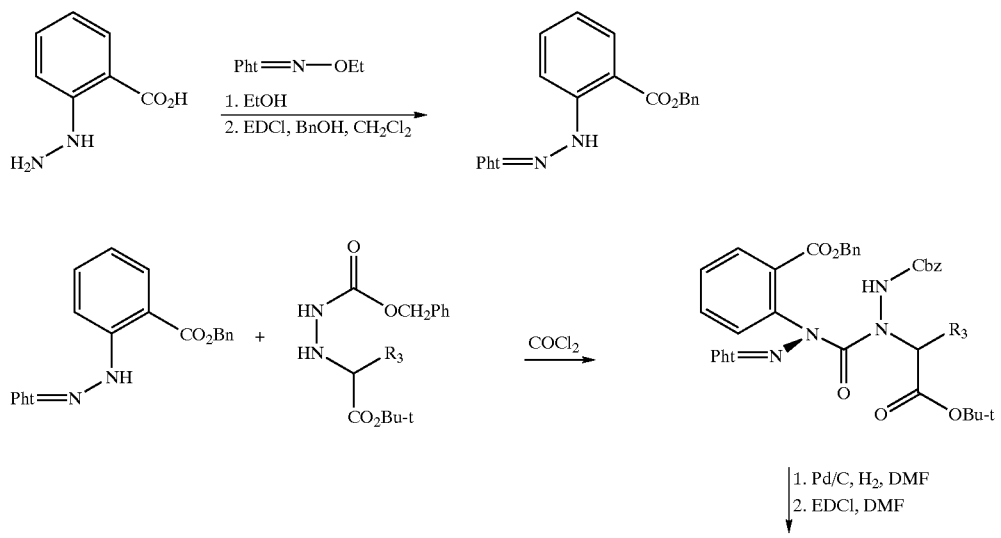

41
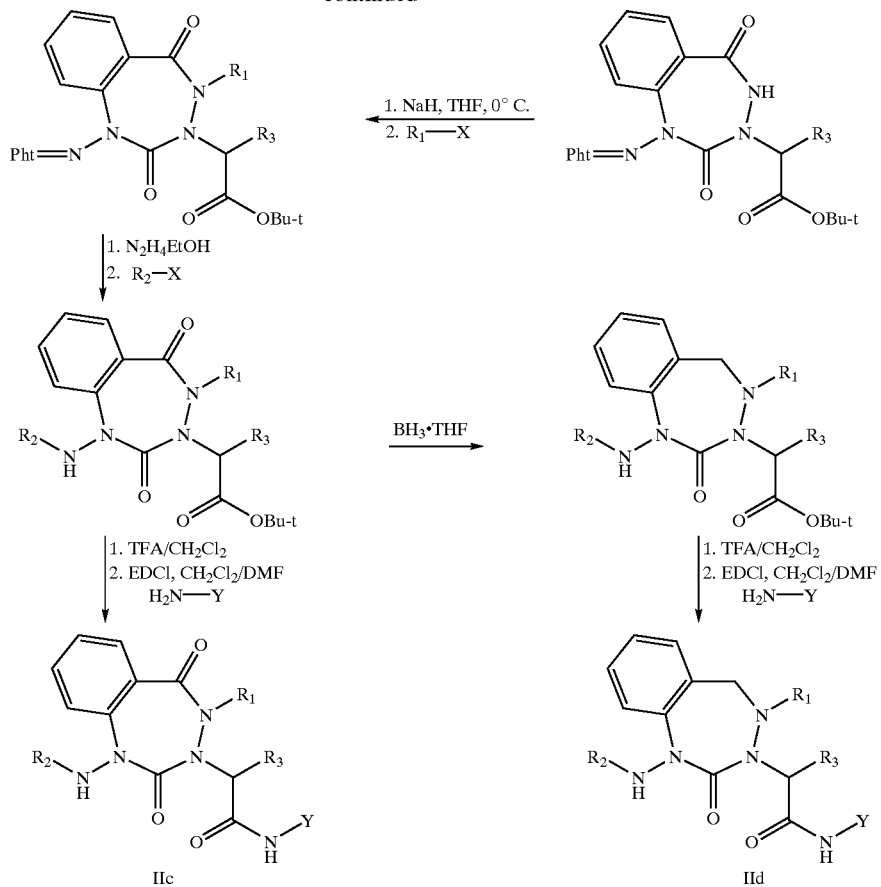
Compounds represented by formulae (I) or (II), wherein $R^{19}$ and Y, together with the nitrogen atom to which they are bound, form a ring (g), may be prepared as described in Scheme 5.
Scheme 5. Synthesis of analogs of Embodiment (g)
Route I
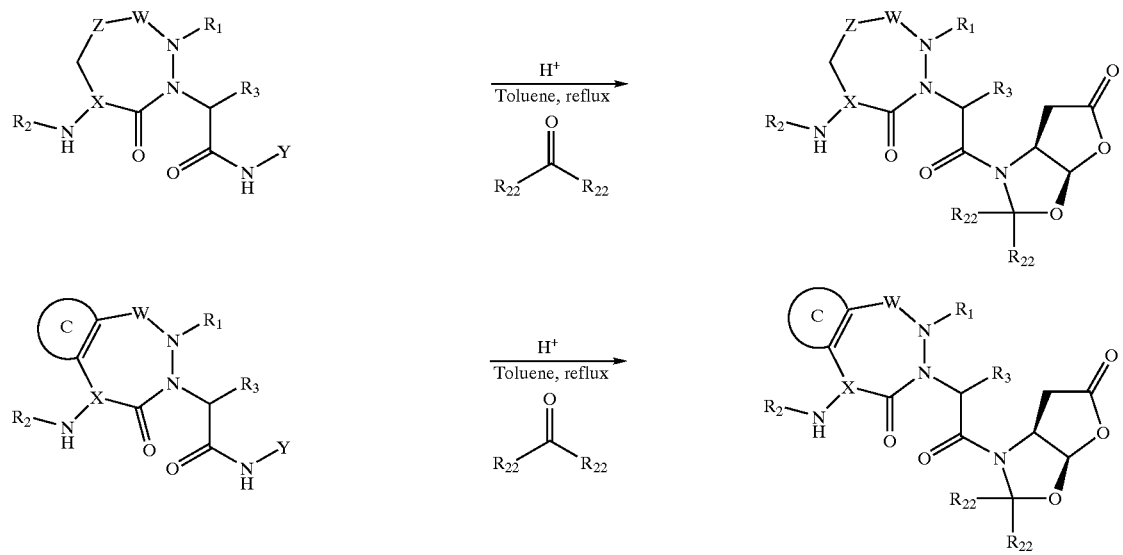

Route II

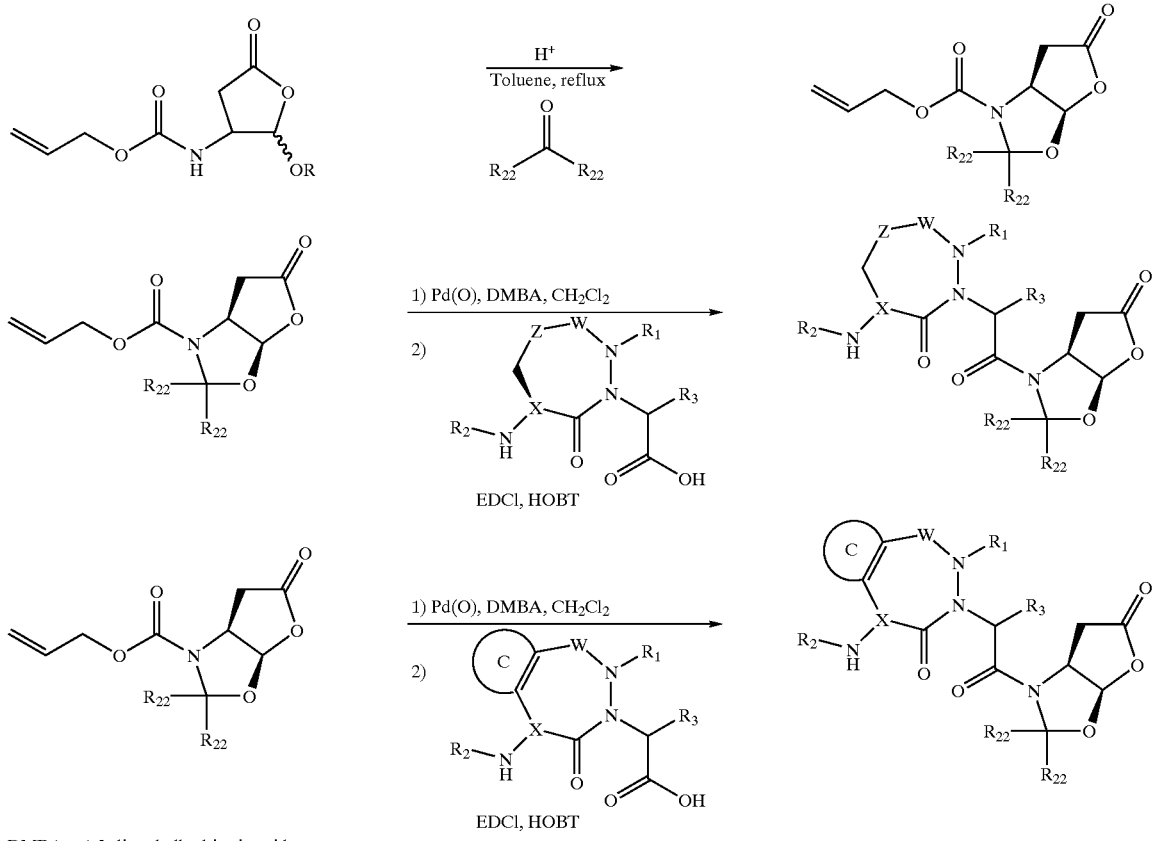

DMBA = 1,3-dimethylbarbituric acid

Scheme 5 describes the synthesis of compounds wherein m is 0. Compounds wherein m is 1 may be prepared by similar methods. The N-alloc protected amine may be protected with other groups that are well known to the skilled practitioner. The palladium coupling method is described in more detail in PCT application PCT/US96/20843, publication no. WO 97/22619, which is incorporated herein by reference.

Schemes 1–5 describes the synthesis of certain embodiments of this invention. Other embodiments may be prepared by similar methods.

EXAMPLE 2

1. Enzyme assay with UV-visible substrate

This assay is run using an Succinyl-Tyr-Val-Ala-Asp-p-Nitroanilide substrate. Synthesis of analogous substrates is described by L. A. Reiter (*Int. J. Peptide Protein Res.*, 43, pp. 87–96 (1994)). The assay mixture contains:

| | |
|---|---|
| 65 μl | buffer (10 mM tris, 1 mM DTT, 0.1% CHAPS @ pH 8.1) |
| 10 μl | ICE (50 nM final concentration to give a rate of ~1 mOD/min) |
| 5 μl | DMSO/Inhibitor mixture |
| 20 μl | 400 μM Substrate (80 μM final concentration) |
| 100 μl | total reaction volume |

The visible ICE assay is run in a 96-well microtiter plate. Buffer, ICE and DMSO (if inhibitor is present) are added to the wells in the order listed. The components are left to incubate at room temperature for 15 minutes starting at the time that all components are present in all wells. The microtiter plate reader is set to incubate at 37° C. After the 15 minute incubation, substrate is added directly to the wells and the reaction is monitored by following the release of the chromophore (pNA) at 405–603 nm at 37° C. for 20 minutes. A linear fit of the data is performed and the rate is calculated in mOD/min. DMSO is only present during experiments involving inhibitors, buffer is used to make up the volume to 100 μl in the other experiments.

2. Enzyme Assay with Fluorescent Substrate

This assay is run essentially according to Thornberry et al., *Nature*, 356 pp. 768–774 (1992), using substrate 17 referenced in that article. The substrate is: Acetyl-Tyr-Val-Ala-Asp-amino-4-methylcoumarin (AMC). The following components are mixed:

| |
|---|
| 65 μl buffer (10 mM Tris, 1 mM DTT, 0.1% CHAPS @ pH 8.1) |
| 10 μl ICE (2–10 nM final concentration) |
| 5 μl DMSO/Inhibitor solution |
| 20 μl 150 μM Substrate (30 μM final) |
| 100 μl total reaction volume |

The assay is run in a 96-well microtiter plate. Buffer and ICE are added to the wells. The components are left to incubate at 37° C. for 15 minutes in a temperature-controlled wellplate. After the 15 minute incubation, the reaction is started by adding substrate directly to the wells and the reaction is monitored at 37° C. for 30 minutes by following the release of the AMC fluorophore using an excitation wavelength for 380 nm and an emission wavelength of 460 nm. A linear fit of the data for each well is performed and a rate is determined in fluorescence units per second.

For determination of enzyme inhibition constants ($K_i$) or the mode of inhibition (competitive, uncompetitive or noncompetitive), the rate data determined in the enzyme assays at varying inhibitor concentrations are computer-fit to standard enzyme kinetic equations (see I. H. Segel, *Enzyme Kinetics*, Wiley-Interscience, 1975).

The determination of second order rate constants for irreversible inhibitors was performed by fitting the fluorescence vs time data to the progress equations of Morrison. Morrison, J. F., *Mol. Cell. Biophys.*, 2, pp. 347–368 (1985). Thornberry et al. published a description of these methods for measurement of rate constants of irreversible inhibitors of ICE. Thornberry, N. A., et al. *Biochemistry*, 33, pp. 3923–3940 (1994). For compounds where no prior complex formation can be observed kinetically, the second order rate constants ($k_{inact}$) are derived directly from the slope of the linear plots of $k_{obs}$ vs. inhibitor concentration [I]. For compounds where prior complex formation to the enzyme can be detected, the hyperbolic plots of $k_{obs}$ vs. ([I] are fit to the equation for saturation kinetics to first generate $K_i$ and k'. The second order rate constant kinact is then given by k'/$K_i$.

3. PBMC Cell Assay

IL-1β Assay with a Mixed Population of Human Peripheral Blood Mononuclear Cells (PBMC) or Enriched Adherent Mononuclear Cells Processing of pre-IL-1β by ICE can be measured in cell culture using a variety of cell sources. Human PBMC obtained from healthy donors provides a mixed population of lymphocyte subtypes and mononuclear cells that produce a spectrum of interleukins and cytokines in response to many classes of physiological stimulators. Adherent mononuclear cells from PBMC provides an enriched source of normal monocytes for selective studies of cytokine production by activated cells.

Experimental Procedure:

An initial dilution series of test compound in DMSO or ethanol is prepared, with a subsequent dilution into RPMI-10% FBS media (containing 2 mM L-glutamine, 10 mM HEPES, 50 U and 50 μg/ml pen/strep) respectively to yield drugs at 4×the final test concentration containing 0.4% DMSO or 0.4% ethanol. The final concentration of DMSO is 0.1% for all drug dilutions. A concentration titration which brackets the apparent $K_i$ for a test compound determined in an ICE inhibition assay is generally used for the primary compound screen.

Generally 5–6 compound dilutions are tested and the cellular component of the assay is performed in duplicate, with duplicate ELISA determinations on each cell culture supernatant.

PBMC Isolation and IL-1 Assay:

Buffy coat cells isolated from one pint human blood (yielding 40–45 ml final volume plasma plus cells) are diluted with media to 80 ml and LeukoPREP separation tubes (Becton Dickinson) are each overlaid with 10 ml of cell suspension. After 15 min centrifugation at 1500–1800× g, the plasma/media layer is aspirated and then the mononuclear cell layer is collected with a Pasteur pipette and transferred to a 15 ml conical centrifuge tube (Corning). Media is added to bring the volume to 15 ml, gently mix the cells by inversion and centrifuge at 300×g for 15 min. The PBMC pellet is resuspended in a small volume of media, the cells are counted and adjusted to $6 \times 10^6$ cells/ml.

For the cellular assay, 1.0 ml of the cell suspension is added to each well of a 24-well flat bottom tissue culture plate (Corning). 0.5 ml test compound dilution and 0.5 ml LPS solution (Sigma #L-3012; 20 ng/ml solution prepared in complete RPMI media; final LPS concentration 5 ng/ml). The 0.5 ml additions of test compound and LPS are usually sufficient to mix the contents of the wells. Three control mixtures are run per experiment, with either LPS alone, solvent vehicle control, and/or additional media to adjust the final culture volume to 2.0 ml. The cell cultures are incubated for 16–18 hr at 37° C. in the presence of 5% $CO_2$.

At the end of the incubation period, cells are harvested and transferred to 15 ml conical centrifuge tubes. After centrifugation for 10 min at 200×g, supernatants are harvested and transferred to 1.5 ml Eppendorf tubes. It may be noted that the cell pellet may be utilized for a biochemical evaluation of pre-IL-1β and/or mature IL-1β content in cytosol extracts by Western blotting or ELISA with pre-IL-1β specific antisera.

Isolation of Adherent Mononuclear Cells:

PBMC are isolated and prepared as described above. Media (1.0 ml) is first added to wells followed by 0.5 ml of the PBMC suspension. After a one hour incubation, plates are gently shaken and nonadherent cells aspirated from each well. Wells are then gently washed three times with 1.0 ml of media and final resuspended in 1.0 ml media. The enrichment for adherent cells generally yields $2.5-3.0 \times 10^5$ cells per well. The addition of test compounds, LPS, cell incubation conditions and processing of supernatants proceeds as described above.

ELISA:

Quantikine kits (R&D Systems) may be used for the measurement of mature IL-1β. Assays are performed according to the manufacturer's directions. Mature IL-1β levels of about 1–3 ng/ml in both PBMC and adherent mononuclear cell positive controls are observed. ELISA assays are performed on 1:5, 1:10 and 1:20 dilutions of supernatants from LPS-positive controls to select the optimal dilution for supernatants in the test panel.

The inhibitory potency of the compounds can be represented by an $IC_{50}$ value, which is the concentration of inhibitor at which 50% of mature IL-1β is detected in the supernatant as compared to the positive controls.

The skilled practitioner realizes that values obtained in cell assays may depend on multiple factors. The values may not necessarily represent fine quantitative results.

EXAMPLE 3

Whole Blood Assay for IL-1β Production

Whole blood assay $IC_{50}$ values for compounds of this invention were obtained using the method described below:

Purpose:

The whole blood assay is a simple method for measuring the production of IL-1β (or other cytokines) and the activity of potential inhibitors. The complexity of this assay system, with its full complement of lymphoid and inflammatory cell types, spectrum of plasma proteins and red blood cells is an ideal in vitro representation of human in vivo physiologic conditions.

Materials:
Pyrogen-free syringes (~30 cc)
Pyrogen-free sterile vacuum tubes containing lyophilized Na$_2$EDTA (4.5 mg/10 ml tube)
Human whole blood sample (~30–50 cc) 1.5 ml Eppendorf tubes
Test compound stock solutions (~25 mM in DMSO or other solvent)
Endotoxin-free sodium chloride solution (0.9%) and HBSS Lipopolysaccharide (Sigma; Cat. #L-3012) stock solution at 1 mg/ml in HBSS
IL-1β ELISA Kit (R & D Systems; Cat #DLB50)
TNFα ELISA Kit (R & D Systems; Cat #DTA50)
Water bath or incubator Whole Blood Assay Experimental Procedure:
Set incubator or water bath at 30°C. Aliquot 0.25 ml of blood into 1.5 ml Eppendorf tubes. Note: be Sure to invert the whole blood sample tubes after every two aliquots. Differences in replicates may result if is the cells sediment and are not uniformly suspended. Use of a positive displacement pipette will also minimize differences between replicate aliquots.

Prepare drug dilutions in sterile pyrogen-free saline by serial dilution. A dilution series which brackets the apparent $K_i$ for a test compound determined in an ICE inhibition assay is generally used for the primary compound screen. For extremely hydrophobic compounds, prepare compound dilutions in fresh plasma obtained from the same blood donor or in PBS-containing 5% DMSO to enhance solubility.

Add 25 μl test compound dilution or vehicle control and gently mix the sample. Then add 5.0 μl LPS solution (250 ng/ml stocked prepared fresh: 5.0 ng/ml final concentration LPS), and mix again. Incubate the tubes at 30° C. in a water bath for 16–18 hr with occasional mixing. Alternatively, the tubes can be placed in a rotator set at 4 rpm for the same incubation period. This assay should be set up in duplicate or triplicate with the following controls: negative control—no LPS; positive control—no test inhibitor; vehicle control—the highest concentration of DMSO or compound solvent used in the experiment. Additional saline is added to all control tubes to normalize volumes for both control and experimental whole blood test samples.

After the incubation period, whole blood samples are centrifuged for 10 minutes at ~2000 rpm in the microfuge, plasma is transferred to a fresh microfuge tube and centrifuged at 1000×g to pellet residual platelets if necessary. Plasma samples may be stored frozen at −70° C. prior to assay for cytokine levels by ELISA.

ELISA:
R & D Systems (6.14 McKinley Place N.E. Minneapolis, Minn. 55413) Quantikine kits may be used for measurement of IL-1β and TNF-α. The assays are performed according to the manufacturer's directions. IL-1β levels of ~1–5 ng/ml in positive controls among a range of individuals may be observed. A 1:200 dilution of plasma for all samples is usually sufficient for experiments for ELISA results to fall on the linear range of the ELISA standard curves. It may be necessary to optimize standard dilutions if you observe differences in the whole blood assay. Nerad, J. L. et al., *J. Leukocyte Biol.*, 52, pp. 687–692 (1992).

EXAMPLE 4

The antiviral efficacy of compounds may be evaluated in various in vitro and in vivo assays. For example, compounds may be tested in in vitro viral replication assays. In vitro assays may employ whole cells or isolated cellular components. In vivo assays include animal models for viral diseases. Examples of such animal models include, but are not limited to, rodent models for HBV or HCV infection, the Woodchuck model for HBV infection, and chimpanzee model for HCV infection.

Compounds of this invention may also be evaluated in animal models for dietary alcohol-induced disease.

EXAMPLE 5

Compounds 10a–10d and 11a–11d were prepared as described below:

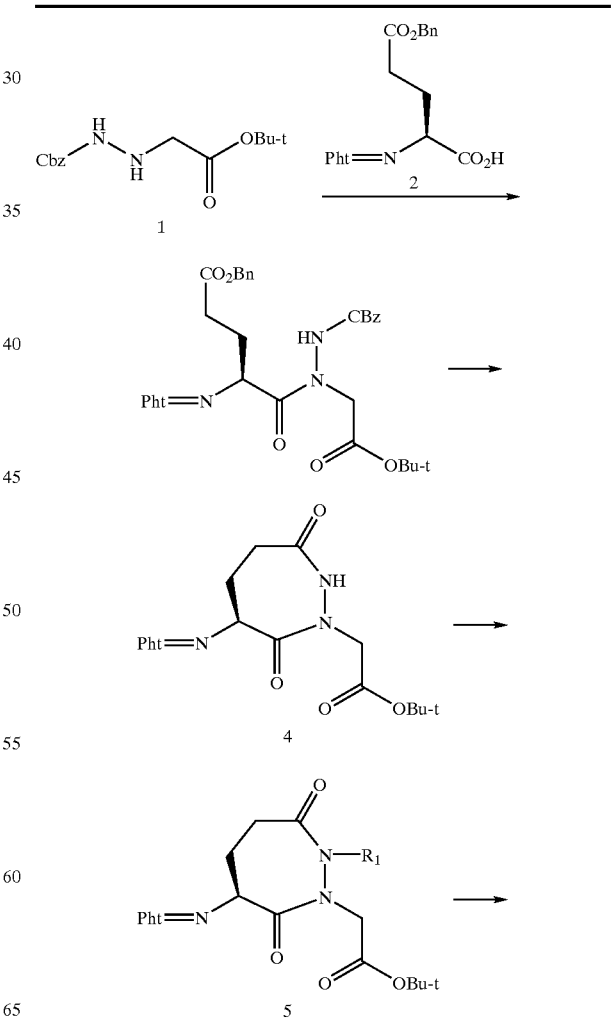

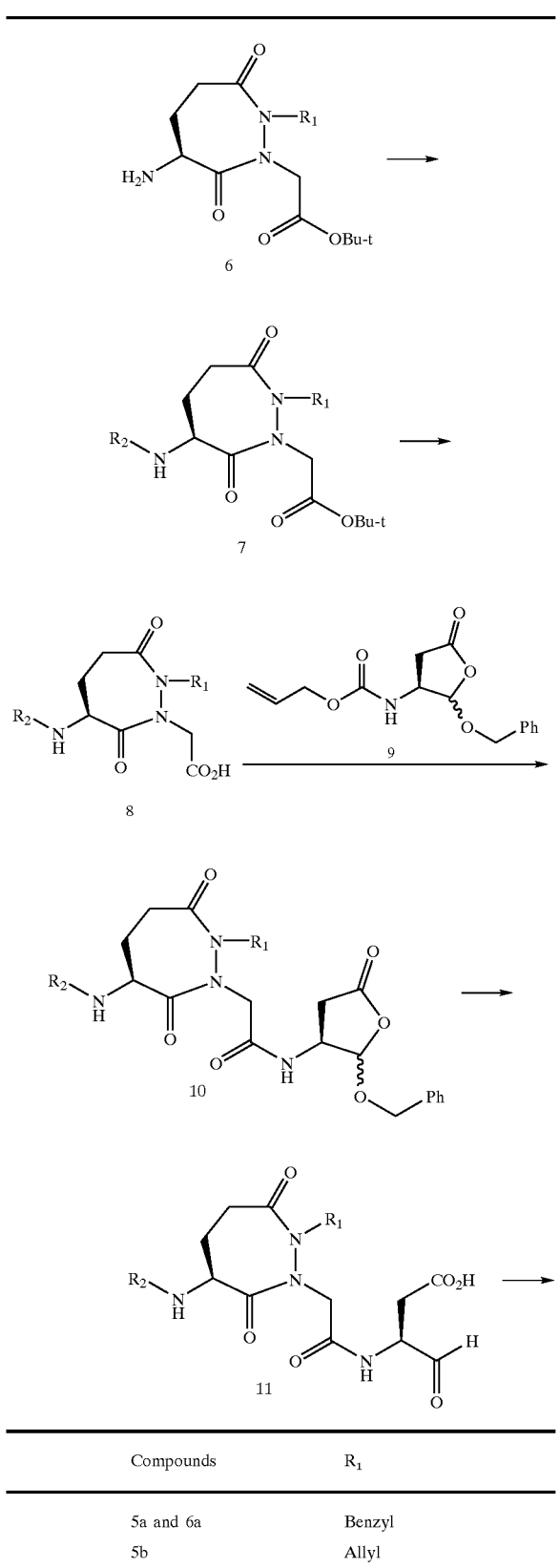

| Compounds | R₁ | R₂ |
|---|---|---|
| 7b, 8b, 10b, 11b | 1-Propyl | (1-acetylisoquinoline) |
| 7c, 8c, 10c | 1-Propyl | (3,5-dichloro-4-allyloxyacetophenone) |
| 10d, 11c | 1-Propyl | (3,5-dichloro-4-hydroxyacetophenone) |

| Compounds | R₁ |
|---|---|
| 5a and 6a | Benzyl |
| 5b | Allyl |
| 5c and 6c | 1-Propyl |

Preparation of (N-Benzyloxycarbonyl-hydrazino)-acetic acid tert-butyl eater (1). To a mixture of benzyl carbamate (25.0 g, 150 mmol), potassium carbonate (20.78 g, 150 mmol) in 230 mL of dimethylformamide (DMF) was added tert-butyl bromoacetate (26.4 g, 145 mmol). The suspension was stirred at room temperature for 16 hours. The reaction mixture was diluted with 1000 mL of ethyl acetate, washed with ice water then water three times. The organic layer was dried over anhydrous $Na_2SO_4$, filtered and evaporated in vacua to afford a clear oil, which was purified by flash chromatography using hexane/EtOAc (9/1 to 7/3) to give 23.55 g (62% yield) of the title compound. $^1$H-NMR (500 MHZ, $CDCl_3$) δ 1.45 (s, 9H), 3.55 (s, 2H), 4.20 (br, 1H), 5.15 (s, 2H), 6.70 (br, 1H), 7.40 (s, 5H). Analytical HPLC*: 10.11 min.

Preparation of 2-(1,3-Dioxo-1,3-dihydro-isoindol-2-yl)-pentanedioic acid 5-benzyl ester (2). A mixture of γ-benzyl-l-glutamate (11.85 g, 50 mmol) and phthalic anhydride (7.40 g, 50 mmol) in toluene (150 mL) was refluxed with a Dean-Stark tube for 16 hours. Solvent was removed under reduced pressure. The residue was purified by flash chromatography using hexane/ethyl acetate/acetic acid (90/10/1 to 50/50/1) to afford 14.83 g (80% yield) of the title compound. $^1$H-NMR (500 MHz, $CDCl_3$) δ 2.40–2.70 (m, 4H), 4.95–5.10 (m, 3H), 7.27–7.40 (m, 5H), 7.70–7.95 (m, 4H). Analytical HPLC: 13.28 min. LC-MS (ES⁺): m/e=368 (M+H⁺).

Preparation of 5-(N'-Benzyloxycarbonyl-N-tert-butoxycarbonylmethyl-hydrazino)-4-(1,3-dioxo-1,3-dihydro-isoindol-2-yl)-5-oxo-pentanoic acid benzyl ester (3). To a solution of 2-(1,3-dioxo-1,3-dihydro-isoindol-2-yl)-pentanedioic acid 5-benzyl ester (2) (1.84 g, 5 mmol) in 25 mL of dichloromethane with 0.1 mL of dimethylformamide (DMF) was dropwise added oxalyl chloride (666 mg, 5.25 mmol) at 0° C. The solution was stirred at 0° C. for 30 min then at room temperature for one hour. $K_2CO_3$ (1.03 g) was added at 0° C. followed by a solution of (N-benzyloxycarbonyl-hydrazino)-acetic acid tert-butyl ester (1) (1.40 g, 5 mmol) in 5 ml of dichloromethane. The mixture was stirred at room temperature for 16 hours. The solvent was removed under reduced pressure and the residue was suspended in 400 mL of ethyl acetate, washed with water (200 mL×2) then brine (200 mL×2). The organic layer was dried over anhydrous $Na_2SO_4$, filtered, concentrated in vacuo to afford 2.8 g of clear oil. Flash chromatography using hexane/ethyl acetate (9/1 to 7/3) gave 1.93 g (61% yield) of the title compound. $^1$H-NMR (500 MHz, $CDCl_3$) δ 1.35 (s, 9H), 2.30–2.55 (m, 4H), 4.70–5.20 (br, 4H), 5.08 (s, 2H), 5.30 (m, 1H), 7.26–7.35 (m, 10H), 7.65–7.90 (m, 4H). Analytical HPLC: 14.6 min. LC-MS ($ES^+$): m/e=630 ($M+H^+$).

Preparation of [6-(1,3-Dioxo-1,3-dihydro-isoindol-2-yl)-3,7-dioxo-[1,2]diazepan-1-yl]-acetic acid tert-butyl ester (4). A suspension of 5-(N'-benzyloxycarbonyl-N-tert-butoxycarbonylmethyl-hydrazino)-4-(1,3-dioxo-1,3-dihydro-isoindol-2-yl)-5-oxo-pentanoic acid benzyl ester (3) and 10% palladium on carbon (250 mg) in tetrahydrofuran (THF) (30 mL) and DMF (3 mL) was stirred under hydrogen atmosphere for 16 hours. The mixture was filtered through Celite and the filtrate was evaporated in vacuo. The residue was dissolved in 30 mL of dichloromethane. 1-(3-Dimethylaminopropyl)-3-ethylcarbodiimide hydrochloride (EDC) (770 mg, 4 mmol) was added and the solution was stirred at room temperature for 3.5 hours. Solvent was removed in vacuo and the residue was dissolved in ethyl acetate (300 mL), then washed with water (100 mL×2). The organic layer was dried over anhydrous $Na_2SO_4$, filtered, purified by flash chromatography using hexane/ethyl acetate (85/15 to 50/50) to afford 1.06 g (75% yield) of the title compound. $^1$H-NMR (500 MHz, $CDCl_3$) δ 1.40 (s, 9H), 2.30–2.40 (m, 1H), 2.40–2.50 (m, 1H), 3.05–3.12 (m, 1H), 3.38–3.48 (m, 1 H), 3.90–4.00 (d, 1H), 4.60–4.70 (d, 1H), 5.55–5.63 (m, 1H), 7.65 (s, 1H), 7.75–7.7.9 (m, 2H), 7.88–7.92 (m, 2H). Analytical HPLC: 10.36 min. LC-MS ($ES^+$): m/e=388 ($M+H^+$).

Preparation of [2-Denzyl-6-(1,3-dioxo-1,3-dihydro-isoindol-2-yl)-3,7-dioxo-[1,2]diazepan-1-yl]-acetic acid tert-butyl ester (5a). A mixture of [6-(1,3-dioxo-1,3-dihydro-isoindol-2-yl)-3,7-dioxo-[1,2]diazepan-1-yl]-acetic acid tert-butyl ester (4) (200 mg, 0.52 mmol), benzyl bromide (110 mg, 0.64 mmol), $K_2CO_3$ (125 mg, 0.9 mmol) and benzyltriethylammonium chloride (15 mg) in THF (5 mL) was stirred at room temperature for 40 hours. The mixture was diluted with ethyl acetate (100 mL) and washed with water three times. The organic layer was dried over anhydrous $Na_2SO_4$ and filtered. The filtrate was purified by flash chromatography using dichloromethane/ethyl acetate (99.5/0.5 to 97.5/2.5) to afford 166 mg (67% yield) of the title compound. $^1$H-NMR (500 MHz, $CDCl_3$) δ 1.40 (s, 9H), 2.30–2.40 (m, 1H), 2.50–2.57 (m, 1H), 3.30–3.40 (m, 1H), 3.60–3.68 (m, 1H), 3.72–3.80 (d, 1H), 4.48–4.52 (d, 1H), 4.80–4.92 (q, 2H), 5.15–5.20 (m, 1H), 7.35 (s, 5H), 7.70 (d, 2H), 7.82 (d, 2H). Analytical HPLC: 13.43 min. LC-MS ($ES^+$): m/e=478 ($M+H^+$).

[2-Allyl-6-(1,3-dioxo-1,3-dihydro-isoindol-2-yl)-3,7-dioxo-[1,2]diazepan-1-yl]-acetic acid tert-butyl ester (5b) was synthesized from 4 and allyl bromide by the method and chromatography used to prepare 5a to afford 388 mg (91% yield) of the title compound. $^1$H-NMR (500 MHZ, $CDCl_3$) δ 1.40 (s, 9H), 2.35–2.45 (m, 1H), 2.48–2.52 (m, 1H), 3.42–3.50 (m, 1H), 3.63–3.70 (m, 1H), 3.82–3.90 (m, 2H), 4.65–4.67 (d, 1H), 4.70–4.77 (q, 1H), 5.35–5.42 (m, 2H), 6.00–6.10 (m, 1H), 7.71–7.74 (d, 2H), 7.82–7.85 (d, 2H). Analytical HPLC: 13.28. LC-MS ($ES^+$): m/e=428 ($M+H^+$).

Preparation of [6-(1,3-Dioxo-1,3-dihydro-isoindol-2-yl)-3,7-dioxo-2-propyl-[1,2]diazepan-1-yl]-acetic acid tert-butyl ester (5c). A mixture of [2-allyl-6-(1,3-dioxo-1,3-dihydro-isoindol-2-yl)-3,7-dioxo-[1,2]diazepan-1-yl]-acetic acid tert-butyl ester (5b) (380 mg, 0.89 mmol) and 20% palladium (II) hydroxide on carbon (Pearlman's catalyst) (80 mg) in ethanol (10 mL) was stirred under hydrogen atmosphere for 3 hours. The reaction mixture was filtered through Celite and the filtrate was evaporated in vacuo to give 380 mg (99.5% yield) of the title compound. $^1$H-NMR (500 MHz, $CDCl_3$) δ 1.05–1.09 (t, 3H), 1.47 (s, 9H), 1.71–1.82 (m, 2H), 2.33–2.46 (m, 1H), 5 2.46–2.53 (m, 1H), 3.00–3.09 (m, 1H), 3.43–3.60 (m, 2H), 3.95–4.00 (d, 1H), 4.10–4.18 (m, 1H), 4.54–4.58 (d, 1H), 5.40–5.45 (m, 1H), 7.70–7.76 (m, 2H), 7.80–7.85 (m, 2H). Analytical HPLC: 13.53 min. LC-MS ($ES^+$): m/e=430 ($M+H^+$).

Preparation of (6-Amino-2-benzyl-3,7-dioxo-[1,2]diazepan-1-yl)-acetic acid tert-butyl ester (6a). A solution of (2-benzyl-6-(1,3-dioxo-1,3-dihydro-isoindol-2-yl)-3,7-dioxo-[1,2]diazepan-1-yl]-acetic acid tert-butyl ester (5a) (150 mg, 0.31 mmol) and hydrazine monohydrate (17.3 mg, 35 mmol) in ethanol (1.5 mL) was stirred at room temperature for 6 hours. Solvent was removed in vacuo. The residue was taken up into acetic acid (1.5 mL) and stirred at room temperature for 30 min. The mixture was evaporated in vacuo and the resulting residue was dissolved in ethyl acetate (20 mL), washed with 5% $Na_2CO_3$ then water. The aqueous solution was extracted with ethyl acetate (20 mL×2). The combined organic layers were dried over $Na_2SO_4$ and filtered. The filtrate was evaporated to dryness in vacuo to afford 107 mg (98% yield) of the title compound. $^1$H-NMR (500 MHz, $CDCl_3$) δ 1.45 (s, 9H), 1.70–1.78 (m, 1H), 2.30–2.48 (m, 2H), 3.10–3.15 (m 1H), 3.30–3.38 (m, 1H), 3.95–4.00 (d, 1H), 4.36–4.40 (d, 1H), 4.45–4.49 (d, 1H), 5.07–5.12 (d, 1H), 7.28–7.38 (m, 5H). Analytical HPLC: 8.03 min. LC-MS ($ES^+$): m/e=348 ($M+H^+$).

(6-Amino-3,7-dioxo-2-propyl-[1,2]diazepan-1-yl)-acetic acid tert-butyl ester (6c) was prepared from 5c by the method used to prepare 6 a to afford 182 mg (69% yield) of the title compound. $^1$H-NMR (500 MHz, $CDCl_3$) δ 0.94–1.01 (t, 3H), 1.50 (s, 9H), 1.55–1.67 (m, 2H), 1.70–1.80 (m, 1H), 2.30–2.37 (m, 1H), 2.50–2.60 (m, 1H), 3.10–3.18 (m, 1H), 3.21–3.28 (m, 1H), 3.81–3.87 (m, 1H), 3.91–3.98 (m, 1H), 4.10–4.15 (d, 1H), 4.39–4.43 (d, 1H). Analytical HPLC: 6.10 min. LC-MS ($ES^+$): m/e=300 ($M+H^+$). Preparation of {2-Benzyl-6-[(isoquinoline-1-carbonyl)-aminol-3,7-dioxo-[1,2]diazepan-1-yl}-acetic acid tert-butyl ester (7a). To a solution of ioquinoline-1-carbonic acid (173 mg, 1 mmol) in dichloromethane (5 mL) was added HOBT (135 mg, 1 mmol) followed by EDC (192 mg, 1 mmol) at 0° C. The mixture was stirred for 15 min and a solution of (6-amino-2-benzyl-3,7-dioxo-[1,2]diazepan-1-yl)-acetic acid tert-butyl ester (6a) (105 mg, 0.30 mmol) in dichloromethane (5 mL) was added. The reaction was stirred at 0° C. for 30 min then at room temperature for 16 hours. The mixture was diluted with dichloromethane (50 mL) and washed with water (50 mL×3). The organic layer was dried over anhydrous $Na_2SO_4$, filtered and evaporated in vacuo to give a pale yellow solid, that was purified by flash chromatography using dichloromethane/ethyl acetate (95/5 to 85/15) to afford 128 mg (84% yield) of the title compound. $^1$H-NMR (500 MHz, $CDCl_3$) δ 1.49 (s, 9H), 2.02–2.10 (m, 1H), 2.50–2.57 (m, 1H), 2.88–2.97 (m, 1H), 3.60–3.70 (m, 1H), 3.84–3.89 (d, 1H), 4.52–4.57 (d, 1H), 4.84–4.98 (m, 3H), 7.26–7.42 (m, 5H), 7.64–7.84 (m, 4H), 8.45 (d, 1H), 8.76 (d, 1H), 9.44 (d, 1H). Analytical HPLC: 14.20 min. LC-MS ($ES^+$): m/e=503 ($M+H^+$).

[6-(Isoquinoline-1-carbonylamino)-3,7-dioxo-2-propyl-11,2]diazepan-1-yl]-acetic acid tert-butyl ester (7b) was prepared from (6-amino-3,7-dioxo-2-propyl-[1,2]diazepan-1-yl)-acetic acid tert-butyl ester (6c) and ioquinoline-1-carbonic acid by the method and chromatography used to prepare 7a to afford 234 mg (86% yield) of the title compound. $^1$H-NMR (500 MHz, CDCl$_3$) δ 1.01–1.07 (t, 3H), 1.49 (s, 9H), 1.73–1.82 (m, 1H), 2.03–2.12 (m, 1H), 2.42–2.50 (m, 1H), 2.84–2.93 (m, 1H), 3.15–3.22 (m, 1H), 3.50–3.58 (m, 1H), 4.03–4,15 (m, 2H), 4.60–4.63 (d, 1H), 5.23–5.30 (m, 1H), 7.64–7.83 (m, 2H), 7.80–7.88 (m, 2H), 8.50 (d, 1H), 8.87 (d, 1H), 9.55 (d, 1H). Analytical HPLC: 10.45 min. LC-MS (ES$^+$): m/e=455 (M+H$^+$).

[6-(4-Allyloxy-3,5-dichloro-benzoylamino)-3,7-dioxo-2-propyl-[1,2]diazepan-1-yl]-acetic acid tert-butyl ester (7c) was prepared from (6-amino-3,7-dioxo-2-propyl-[1,2]diazepan-1-yl)-acetic acid tert-butyl ester (6c) and 3,5-dichloro-4-allyloxy-benzoyl acid by the method and chromatography used to prepare 7a to afford 200 mg (72% yield) of the title compound. $^1$H-NMR (500 MHz, CDCl$_3$) δ 0.96–1.00 (t, 3H), 1.50 (s, 9H), 1.64–1.73 (m, 2H), 1.90–1.97 (m, 1H), 2.40–2.45 (m, 1H), 2.83–2.92 (m, 1H), 3.10–3.17 (m, 1H), 3.40–3.49 (m, 1H), 4.02–4.10 (m, 2H), 4.48–4.51 (d, 1H), 4.60–4.63 (m, 2H), 5.11–5.18 (m, 1H), 5.30–5.34 (d, 1H), 5.40–5.44 (d, 1H), 6.10–6.18 (m, 1H), 7.86–7.89 (d, 1H), 7.73 (s, 2H). Analytical HPLC: 10.47 min. LC-MS (ES$^+$): m/e 528, 530 (M+H$^+$).

Preparation of Isoquinoline-1-carboxylic acid {1-benzyl-2-[(2-benzyloxy-5-oxo-tetrahydro-furan-3-ylcarbamoyl)-methyl]-3,7-dioxo-[1,2]diazepan-4-yl}-amide (10a). {2-Benzyl-6-[(isoquinoline-1-carbonyl)-amino]-3,7-dioxo-[1,2]diazepan-1-yl}-acetic acid tert-butyl ester (7a) (115 mg, 0.23 mmol) was stirred in 20% of trifluoroacetic acid (TFA) in dichloromethane (2 mL) overnight. The solution was evaporated to afford {2-benzyl-6-[(isoquinoline-1-carbonyl)-amino-3,7-dioxo-[1,2]diazepan-1-yl}-acetic acid (8a). $^1$H-NMR (500 MHz, CDCl$_3$) δ 2.05–2.11 (m, 1H), 2,45–2.50 (m, 1H), 2.72–2.83 (m, 1H), 3.45–3.54 (m, 1H), 4.01–4.06 (m, 1H), 4.59–4.63 (d, 1H), 4.70–4.82 (m, 1H), 4.93–4.98 (m, 1H), 7.28–7.42 (m, 5H), 7.80–8.10 (m, 4H), 8.40–8.52 (m, 2H), 8.85 (d, 1H). The acid (8a) was dissolved in dichloromethane (2 mL) followed by addition of HOBT (77 mg, 0.57 mmol) and EDC (110 mg, 0.57 mmol) and stirred for 30 min. A solution of (2-benzyloxy-5-oxo-tetrahydro-furan-3-yl)-carbamic acid allyl ester (9, anti diastereomer) (166 mg, 0.57 mmol) in dichloromethane/DMF (3/1 mL), charged with 1,3-dimethylbarbituric acid (DMBA) (90 mg, 0.57 mmol) and Pd(PPh$_3$)$_4$ (66 mg, 0.057 mmol) for 30 min, was added and the resulting mixture was stirred at room temperature for 16 hours. The reaction mixture was diluted with ethyl acetate (100 mL) and washed with water (50 mL×3), dried over Na$_2$SO$_4$, filtered and evaporated to give a pale yellow solid, that was purified by flash chromatography using dichloromethane/methanol (99.5/0.5 to 98.5/1.5) to afford 97.5 mg (67% yield) of the title compound. $^1$H-NMR (500 MHz, CDCl$_3$) δ 2.03–2.13 (m, 1H), 2.40–2.43 (d, 1H), 2.55–2.60 (m, 1H), 2.83–2.92 (m, 1H), 3.04–3.10 (q, 1H), 3.28–3.38 (m, 1H), 4.08–4.11 (d, 1H), 4.20–4.24 (d, 1H), 4.38–4.41 (m, 1H), 4.67–4.70 (d, 1H), 4.78–4.87 (m, 2H), 4.91–5.02 (m, 2H), 5.36 (s, 1H), 6.05 (d, 1H), 7.20–7.38 (m, 10H), 7.68–7.78 (m, 2H), 7.80–7.88 (m, 2H), 8.48 (d, 1H), 8.70 (d, 1H), 9.49 (d, 1H). Analytical HPLC: 12.53 min. LC-MS (ES$^+$): m/e=636 (M+H$^+$).

Isoquinoline-1-carboxylic acid {2-[(2-benzyloxy-5-oxo-tetrahydro-furan-3-ylcarbamoyl)-methyl]-3,7-dioxo-1-propyl-[1,2]diazepan-4-yl}-amide (10b) was synthesized from 7b and the diastereomers of 9 by the method and chromatography used to prepare 10a to afford both syn diastereomer (203 mg, 67% yield, higher Rf) and anti diastereomer (93 mg, 31% yield, lower Rf) of the title compound. $^1$H-NMR (500 MHz, CDCl$_3$) for the anti diastereomer: δ 0.96–1.05 (t, 3H), 1.72–1.82 (m, 2H), 2.10–2.20 (m, 1H), 2.48–2.56 (m, 2H), 2.78–2.86 (m, 1H), 2.92–3.18 (m, 3H), 3.25–3.39 (m, 1H), 3.95–4.02 (m, 1H), 4.06–4.17 (m, 1H), 4.41–4.50 (m, 1H), 4.62–4.66 (d, 1H), 4.82–4.89 (d, 1H), 5.10–5.20 (m, 1H), 5.5 (s, 1H), 6.68 (d, 1H) 7.28–7.40 (m, 5H), 7.70–7.77 (m, 2H), 7.82–7.89 (m, 2H), 8.51 (d, 1H), 8.77 (d, 1H), 9.52 (d, 1H); for the syn diastereomer: δ 0.90–0.98 (t, 3H), 1.60–1.80 (m, 2H), 2.00–2.10 (m, 1H), 2.43–2.50 (m, 2H), 2.80–2.98 (m, 2H), 3.10–3.20 (m, 2H), 4.03–4.17 (m, 2H), 4.29–4.33 (d, 1H), 4.60–4.63 (d, 1H), 4.70–4.79 (m, 1H), 4.85–4.89 (m, 1H), 5.21–5.30 (m, 1H), 5.52 (d, 1H), 6.70 (d, 1H), 7.28–7.33 (m, 5H), 7.64–7.78 (m, 2H), 7.83–7.90 (m, 2H), 8.50 (d, 1H), 8.85 (d, 1H), 9.50 (d, 1H). Analytical HPLC: is 10.60 min for the anti diastereomer and 10.30 min for the syn diastereomer. LC-MS (ES$^+$) for the mixture of the product: m/e 588 (M+H$^+$).

4-Allyloxy-N-{2-[(2-benzyloxy-5-oxo-tetrahydro-furan-3-ylcarbamoyl)-methyl]-3,7-dioxo-1-propyl-[1,2]diazepan-4-yl}-3,5-dichloro-benzamide (10c) was synthesized from 7c and the diastereomers of 9 by the method and chromatography used to prepare 10a to afford both anti diastereomer (78 mg, 31% yield, lower Rf) and syn diastereomer (129 mg, 52% yield, higher Rf) of the title compound. $^1$H-NMR (500Hz, CDCl$_3$) for the anti diastereomer: δ 1.00–1.05 (t, 3H), 1.60–1.80 (m, 2H), 2.03–2.18 (m, 1H), 2.23–2.30 (d, 1H), 2.40–2.48 (m, 1H), 2.62–2.78 (m, 1H), 2.90–3.12 (m, 2H), 3.50–3.60 (m, 1H), 4.05–4.25 (m, 3H), 4.48–4.52 (m, 1H), 4.60–4.68 (m, 3H), 4.80–44.85 (d, 1H), 5.08–5.20 (m, 1H), 5.30–5.39 (m, 2H), 5.40–5.45 (d, 1H), 6.08–6.20 (m, 1H), 6.82–6.85 (d, 1H), 7.30–7.45 (m, 6H), 7.85 (s, 2H); for the syn diastereomer: δ 0.94–1.04 (t, 3H), 1.60–1.72 (m, 2H), 1.85–1.93 (m, 1H), 2.31–2.40 (m, 1H), 2.41–2.51 (m, 1H), 2.72–2.82 (m, 1H), 2.83–2.95 (m, 1H), 3.00–3.09 (m, 1H), 3.17–3.30 (m, 1H), 3.99–4.10 (m, 1H), 4.10–4.18 (d, 1H), 4.21–4.30 (d, 1H), 4.58–4.65 (m, 3H), 4.70–4.78 (m, 1H), 4.85–4.90 (d, 1H), 5.05–5.15 (m, 1H), 5.28–5.35 (d, 1H), 5.40–5.45 (d, 1H), 5.53 (d, 1H), 6.08–6.17 (m, 1H), 6.55–6.60 (d, 1H), 6.75–6.80 (d, 1H), 7.27–7.40 (m, 3H), 7.40–7.55 (m, 1H), 7.60–7.70 (m, 1H), 7.73 (s, 2H). Analytical HPLC for diastereomers of the title compound: 10.26 min. LC-MS (ES$^+$) for the mixture of the product: m/e=661, 663 (M+H$^+$).

Preparation of N-{2-[(2-Benzyloxy-5-oxo-tetrahydro-furan-3-ylcarbamoyl)-methyl]-3,7-dioxo-1-propyl-[1,2]diazepan-4-yl}-3,5-dichloro-4-hydroxy-benzamide (10d). To a solution of 4-allyloxy-N-{2-[(2-benzyloxy-5-oxo-tetrahydro-furan-3-ylcarbamoyl)-methyl]-3,7-dioxo-1-propyl-[1,2]diazepan-4-yl}-3,5-dichloro-benzamide (10c, diastereomers) (103 mg, 0.16 mmol) in dichloromethane (15 mL) was added DMBA followed by Pd(PPh$_3$)$_4$ (30 mg, 0.026 mmol), stirred at room temperature for 7 hours. The reaction mixture was washed with water, dried over anhydrous Na$_2$SO$_4$, filtered and purified by flash chromatography using dichloromethane/methanol (99.5/0.5 to 97/3) to afford both anti diastereomer (18 mg, 18% yield, lower Rf) and syn diastereomer (48 mg, 50% yield, higher Rf) of the title compound. $^1$H-NMR (500 MHz, CDCl$_3$) for the anti diastereomer: δ 0.9–1.02 (m, 3H), 1.65–185 (m, 2H), 2.01–2.18 (m, 0.5H), 2.20–2.30 (d, 0.5H), 2.37–2.47 (m, 1H), 2.58–2.70 (m, 1H), 2.90–3.00 (m, 1H), 3.00–3.10 (m, 1H), 3.25–3.50 (m, 1H), 4.0–4.15 (m, 2H), 4.15–4.25 (d, 1H), 4.40–4.55 (m, 1H), 4.55–4.67 (m, 1H), 4.72–4.82 (d, 1H), 5.05–5.17 (m, 1H), 5.27–5.38 (m, 2H), 6.90–7.00 (d, 1H), 7.25–7.40 (m, 6H), 7.60–7.70 (m, 1H), 7.80 (s, 2H; for the syn diastereomer: δ 0.9–1.00 (m, 3H), 1.50–1.70 (m, 2H), 1.8–1.92 (m, 1H), 2.38–2.42 (m, 1H), 2.48–2.58 (m, 1H), 2.74–2.87 (m, 1H), 2.88–2.98 (m, 1H), 3.00–3.13 (m, 1H), 3.17–3.30 (m, 1H), 4.00–4.12 (m, 1H), 4.14–4.30 (d, 1H), 4.22–4.32 (m, 1H), 4.62–4.46 (d, 1H), 4.75–4.80 (m, 1H), 4.90–4.95 (d, 1H), 5.10–5.20 (m, 1H), 5.53–5.57 (d, 1H), 6.24 (s, 1H), 6.49 (d, 1H), 6.70 (d, 1H), 7.25–7.40 (m, 5H), 7.71 (s, 2H). Analytical HPLC: 8.55 min for syn diastereomer and 8.57 min for the anti diastereomer. LC-MS (ES$^+$) for the mixture of the product: m/e=621, 623 (M+H$^+$).

Preparation of 3-(2-{2-Benzyl-6-[(isoquinoline-1-carbonyl)-amino]-3,7-dioxo-[1,2]diazepan-1-yl}-acetylamino)-4-oxo-butyric acid (11a). Isoquinoline-1-carboxylic acid {1-benzyl-2-[(2-benzyloxy-5-oxo-tetrahydro-furan-3-ylcarbamoyl)-methyl]-3,7-dioxo-[1,2] diazepan-4-yl}-amide (10a, diastereomers) (14 mg, 0.022 mmol) was stirred in the solution of 10% HCl (1.5 mL) and acetonitrile (1 mL) for 4 hours. The reaction mixture was diluted with water (30 mL), washed with ether (30 mL) twice. The aqueous solution was purged with nitrogen for 30 min then cooled in dry ice and lyophilized overnight to afford 10 mg (83% yield) of the title compound. $^1$H-NMR (500 MHz, CD$_3$OD) δ 2.00–2.10 (m, 1H), 2.32–2.50 (m, 2H), 3.62–3.72 (m, 1H), 4.15–4.35 (m, 2H), 4.45–4.80 (m, 4H), 5.25–5.32 (m, 1H), 7.30–7.68 (m, 5H), 7.95–8.05 (m, 1H), 8.12–8.17 (m, 1H), 8.22–8.27 (m, 1H), 8.35–8.41 (d, 1H), 8.56 (s, 1H), 8.65–8.74 (d, 1H). Analytical HPLC: 9.40 min. LC-MS (ES$^+$): m/e=546 (M+H$^+$).

3-(2-(6-[(Isoquinoline-1-carbonyl)-amino]-3,7-dioxo-2-propyl-[1,2]diazepan-1-yl)-acetylamino)-4-oxo-butyric acid (11b) was prepared from isoquinoline-1-carboxylic acid {2-[(2-benzyloxy-5-oxo-tetrahydro-furan-3-ylcarbamoyl)-methyl]-3,7-dioxo-1-propyl-[1,2]diazepan-4-yl}-amide (10b, diastereomers) (95 mg, 0.16 mmol) by the method used to prepare 11a to afford 28 mg (35% yield) of the title compound. $^1$H-NMR (500 MHz, CDCl$_3$/CD$_3$OD=0.5 mL/3 drops) δ 0.90–1.00 (t, 3H), 1.65–1.80 (m, 2H), 2.10–2.28 (m, 1H), 2.32–2.40 (m, 1H), 2.47–2.80 (m, 3H), 3.05–3.18 (m, 1H), 3.30–3.51 (m, 2H), 4.00–4.55 (m, 3H), 5.10–5.20 (m, 1H), 7.75–8.05 (m, 4H), 8.49 (s, 1H), 8.90–9.00 (m, 1H). Analytical HPLC: 6.26 min. LC-MS (ES$^+$): m/e=498 (M+H$^+$).

3-{2-[6-(3,5-Dichloro-4-hydroxy-benzoylamino)-3,7-dioxo-2-propyl-[1,2]diazepan-1-yl]-acetylamino}-4-oxo-butyric acid (11c) was prepared from N-{2-[(2-benzyloxy-5-oxo-tetrahydro-furan-3-ylcarbamoyl)-methyl]-3,7-dioxo-1-propyl-[1,2]diazepan-4-yl}-3,5-dichloro-4-hydroxy-benzamide (10d, diastereomers) (30 mg, 0.05 mmol) by the method used to prepare 11a to afford 19 mg (74% yield) of the title compound. $^1$H-NMR (500 MHz, CDCl$_3$/CD$_3$OD= 0.5 mL/3 drops) δ 0.90–0.95 (t, 3H), 1.60–1.70 (m, 2H), 2.00–2.10 (m, 1H), 2.25–2.36 (m, 1H), 2.48–2.82 (m, 3H), 2.98–3.10 (m, 1H), 3.20–3.35 (m, 1H), 3.90–4.50 (m, 4H), 4.95–5.08 (m, 1H), 7.62–7.72 (m, 2H). Analytical HPLC: 5.40 min. LC-MS (ES$^+$): m/e=531, 533 (M+H$^+$).

3-{2-[6-(3,5-Dichloro-4-hydroxy-benzoylamino)-3,7-dioxo-2-methyl-[1,2]diazepan-1-yl]-acetylamino}-4-oxo-butyric acid (11d) was prepared according to the method used to prepare (11c) only substituting iodomethane for allyl bromide.

EXAMPLE 6

Compounds 19 and 20 were prepared as described below:

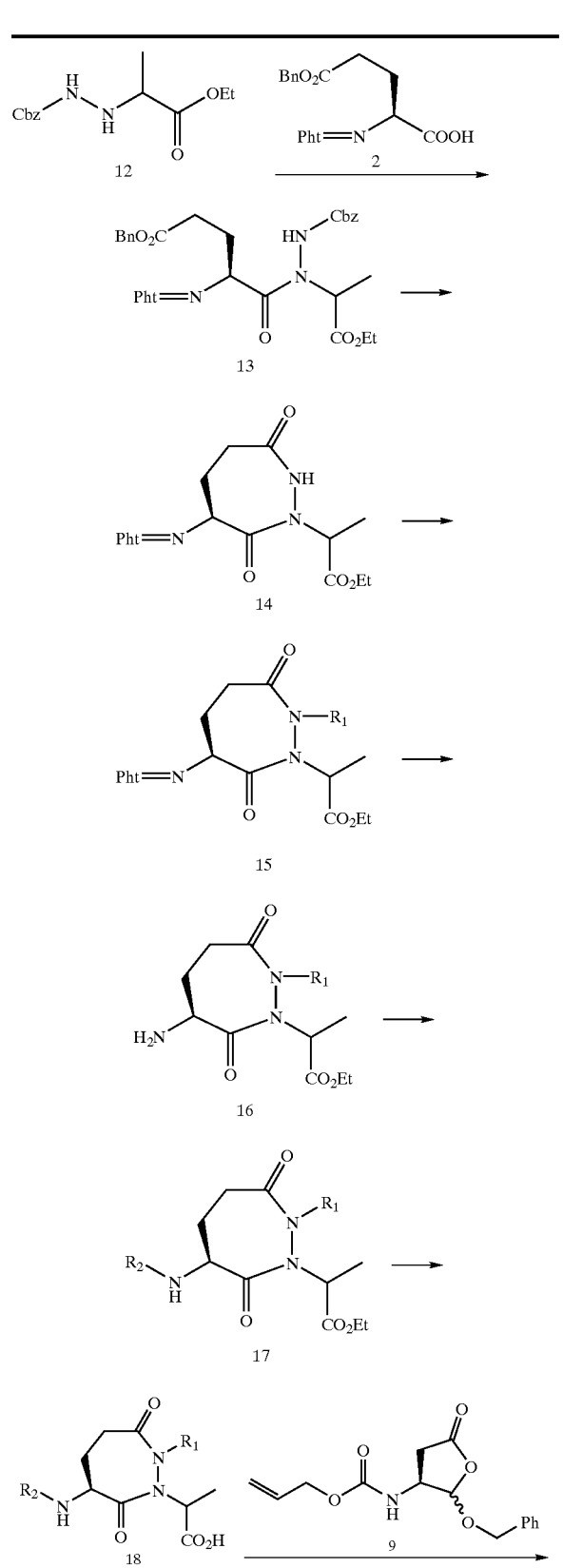

-continued

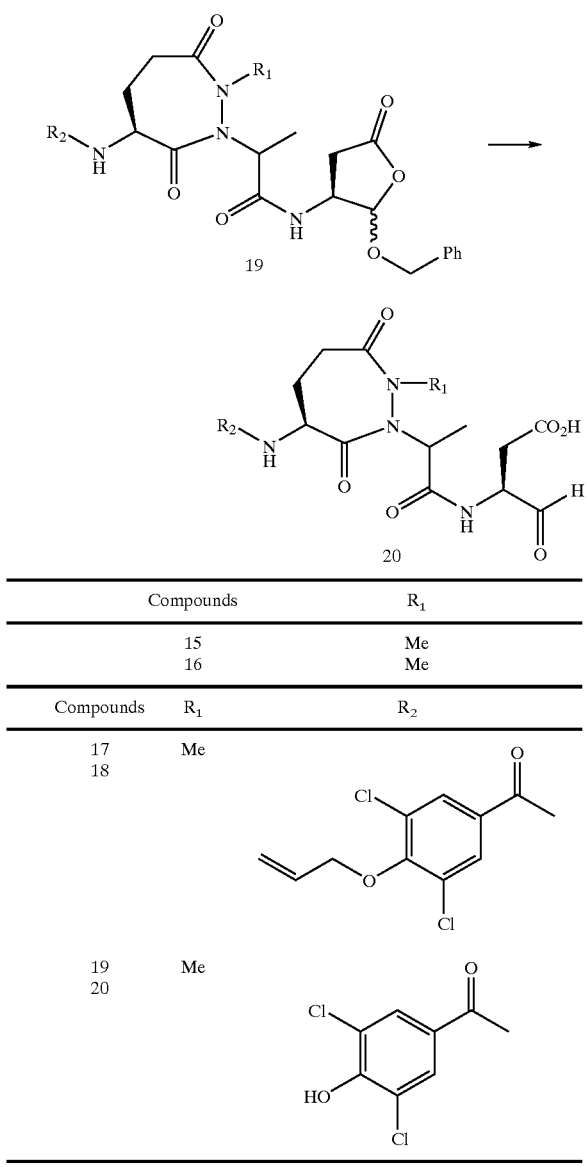

| Compounds | R₁ | |
|---|---|---|
| 15 | Me | |
| 16 | Me | |
| Compounds | R₁ | R₂ |
| 17 | Me | (3,5-dichloro-4-allyloxy-benzoyl) |
| 18 | | |
| 19 | Me | (3,5-dichloro-4-hydroxy-benzoyl) |
| 20 | | |

Preparation of 2-(N'-Benzyloxycarbonyl-hydrazino)-propionic acid ethyl ester (12). To a solution of benzyl carbamate (665 mg, 4 mmol), triethylamine (1.11 mL) in ethane (4 ml) was added dropwise ethyl O-trifluoromethanesulfonyl-D-lactate at 0° C. The solution was stirred at 0° C. for 15 min then at room temperature for 16 hours. The mixture was diluted with dichloromethane (100 mL), washed with water (50 mL×2), 1% HCl (50 mL×2). The organic layer was dried over anhydrous Na₂SO₄, filtered, and evaporated to dryness in vacuo to give 570 mg (54% yield) of the title compound. ¹H-NMR (500 MHz, CDCl₃) δ 1.25–1.40 (m, 6H), 3.68–3.78 (m, 1H), 4.12–4.20 (m, 3H), 5.07–5.15 (m, 1H), 6.45–6.57 (m, 1H), 7.30–7.45 (m, 5H). Analytical HPLC: 5.56 min. LC-MS (ES⁺): m/e=267 (M+H⁺).

5-[N'-Benzyloxycarbonyl-N-(1-ethoxycarbonyl-ethyl)-hydrazino]-4-(1,3-dioxo-1,3-dihydro-isoindol-2-yl)- 5-oxo-pentanoic acid benzyl ester (13) was prepared from 2-(N'-benzyloxycarbonyl-hydrazino)-propionic acid ethyl ester (12) and 2 by the method and chromatography used to prepare 3 to afford 850 mg (64% yield) of the title compound. ¹H-NMR (500 MHz, CDCl₃) δ 1.10–1.50 (m, 6H), 2.40–2.70 (m, 5H), 4.05–4.30 (m, 2H), 4.65–4.70 (d, 0.5H), 4.80–4.86 (d, 0.5H), 5.00–5.40 (m, 5H), 7.15–7.50 (m, 10H), 7.65–7.90 (m, 4H). Analytical HPLC: 9.00 min. LC-MS (ES⁺): m/e=616 (M+H⁺).

2-[6-(1,3-Dioxo-1,3-dihydro-isoindol-2-yl)-3,7-dioxo-[1,2]diazepan-1-yl]-propionic acid tert-butyl ester (14) was prepared from 5-[N'-benzyloxycarbonyl-N-(1-ethoxycarbonyl-ethyl)-hydrazino]-4-(1,3-dioxo-1,3-dihydro-isoindol-2-yl)-5-oxo-pentanoic acid benzyl ester (13) by the method and chromatography used to prepare 4 to afford 318 mg (64% yield) of the title compound. ¹H-NMR (500 MHz, CDCl₃) δ 1.25–1.35 (m, 3H), 1.50–1.60 (m, 3H), 2.37–2.55 (m, 2H), 2.75–2.95 (m, 1H), 3.35–3.65 (m, 2H), 4.15–4.30 (m, 2H), 5.15–5.40 (m, 1H), 5.47–5.60 (m, 1H), 7.65–7.90 (m, 4H). Analytical HPLC: 5.60 min. LC-MS (ES⁺): m/e=(M+H⁺).

Preparation of 2-[6-(1,3-Dioxo-1,3-dihydro-isoindol-2-yl)-2-methyl-3,7-dioxo-[1,2]diazepan-1-yl]-propionic acid ethyl ester (15). A mixture of 2-[6-(1,3-dioxo-1,3-dihydro-isoindol-2-yl)-3,7-dioxo-[1,2]diazepan-1-yl]-propionic acid tert-butyl ester (14) (314 mg, 0.84 mmol), benzyltriethylammonium chloride (30 mg, 0.13 mmol), K₂CO₃ (406 mg, 2.94 mmol) and iodomethane (360 mg, 2.53 mmol) in THF (8 mL) was stirred at room temperature for five days. The mixture was diluted with dichloromethane (70 mL), washed with water three times, dried over anhydrous Na₂SO₄, filtered and evaporated in vacuo to dryness to afford 296 mg (91% yield) of the title compound as a mixture of diastereomers. ¹H-NMR (500 MHZ, CDCl₃) δ 1.25–1.35 (m, 2.5H), 1.47–1.52 (m, 0.5H), 1.60–1.75 (m, 3H), 2.37–2.52 (m, 2H), 3.05–3.14 (m, 0.5H), 3.30–3.45 (m, 3.5H), 3.45–3.58 (m, 1H), 4.14–4.28 (m, 2H), 4.52–4.58 (m, 0.5H), 4.80–4.87 (m, 0.5H), 5.13–5.28 (m, 1H), 7.70–7.90 (m, 4H). Analytical HPLC: 6.00 and 6.11 min. LC-MS (ES⁺): m/e=388 (M+H⁺).

2-(6-Amino-2-methyl-3,7-dioxo-[1,2]diazepan-1-yl)-propionic acid ethyl ester (16) was prepared from 2-[6-(1,3-dioxo-1,3-dihydro-isoindol-2-yl)-2-methyl-3,7-dioxo-[1,2]diazepan-1-yl]-propionic acid ethyl ester (15) by the method used to prepare 6a to afford 143 mg (73% yield) of the title compound as a mixture of diastereomers. ¹H-NMR (500 MHz, CDCl₃) δ 1.22–1.30 (m, 2.5H), 1.47–1.50 (d, 0.5H), 1.52–1.70 (m, 3H), 1.70–1.82 (m, 1H), 2.30–2.40 (m, 1H), 2.48–2.69 (m, 1H), 2.75–2.82 (m, 0.5H), 3.03–3.11 (m, 0.5H), 3.22 (d, 3H), 3.61–3.75 (m, 1H), 4.18–4.30 (m, 2H), 4.49–4.54 (m, 0.5H), 4.85–4.90 (m, 0.5H). Analytical HPLC: 3.90 and 4.06 min. LC-MS (ES⁺): m/e=258 (M+H⁺).

2-[6-(4-Allyloxy-3,5-dichloro-benzoylamino)-2-methyl-3,7-dioxo-[1,2]diazepan-1-yl]-propionic acid ethyl ester (17) was prepared from 2-(6-amino-2-methyl-3,7-dioxo-[1,2]diazepan-1-yl)-propionic acid ethyl ester (16) and 3,5-dichloro-4-allyloxy-benzoyl acid by the method and chromatography used to prepare 7a to afford 216 mg (80% yield) of the title compound as a mixture of diastereomers. ¹H-NMR (500 MHz, CDCl₃) δ 1.22–1.40 (m, 3H), 1.50–1.80 (m, 3H), 1.80–1.95 (m, 1H), 2.40–2.50 (m, 1H), 2.82–3.02 (m, 2H), 3.10–3.40 (m, 4H), 4.20–4.35 (m, 2H), 4.50–5.01 (m, 3H), 5.25–5.45 (m, 2H), 6.05–6.20 (m, 1H), 6.90–7.00 (m, 2H), 7.70–7.80 (d, 2H). Analytical HPLC: 6.97 and 7.06 min. LC-MS (ES⁺): m/e=486, 488 (M+H⁺).

Preparation of 2-[6-(4-Allyloxy-3,5-dichloro-benzoylamino)-2-methyl-3,7-dioxo-[1,2]diazepan-1-yl]-propionic acid (18). 2-[6-(4-Allyloxy-3,5-dichloro-benzoylamino)-2-methyl-3,7-dioxo-[1,2]diazepan-1-yl]-propionic acid ethyl ester (17) (216 mg, 0.44 mmol) was stirred in 1N NaOH (2 mL) and MeOH (2 mL) at room temperature for 45 min. The mixture was diluted with water (30 mL), extracted with dichloromethane three times. The combined organic layers were dried over anhydrous $Na_2SO_4$, filtered and evaporated in vacuo to dryness to afford 201 mg (99% yield) of the title compound. $^1$H-NMR (500 MHz, $CDCl_3$) δ 1.58–1.68 (m, 3H), 1.88–2.00 (m, 1H), 2.40–2.48 (m, 1H), 2.80–3.18 (m, 2H), 3.25–3.48 (d, 3H), 4.47–4.65 (m, 2.5H), 4.74–4.81 (m, 0.5H), 4.90–5.05 (m, 1H), 5.27–5.31 (d, 1H), 5.38–5.43 (d, 1H), 6.08–61.8 (m, 1H), 7.07–7.22 (m, 2H), 7.71 (d, 2H). Analytical HPLC: 5.85 min. LC-MS ($ES^+$): m/e=458, 460 ($M+H^+$).

Preparation of N-{2-[1-(2-Benzyloxy-5-oxo-tetrahydro-furan-3-ylcarbamoyl)-ethyl]-1-methyl-3,7-dioxo-[1,2]diazepan-4-yl}-3,5-dichloro-4-hydroxy-benzamide (19). To a solution of 2-[6-(4-allyloxy-3,5-dichloro-benzoylamino)-2-methyl-3,7-dioxo-[1,2]diazepan-1-yl]-propionic acid (18) (183 mg, 0.40 mmol) in dichloromethane was added HOBT (65 mg, 0.48 mmol) followed by EDC (123 mg, 0.64 mmol). The mixture was stirred at 0° C. for 30 min, then a solution of (2-benzyloxy-5-oxo-tetrahydro-furan-3-yl)-carbamic acid allyl ester (9, anti diastereomer) (140 mg, 0.48 mmol) in dichloromethane, charged with 1,3-dimethylbarbituric acid (DMBA) (75 mg, 0.48 mmol) and $Pd(PPh_3)_4$ (60 mg, 0.05 mmol) for 30 min, was added and the resulting mixture was stirred at room temperature for 5 hours. The second portion of DMBA (63 mg, 0.40 mmol) was added and the reaction mixture was continuously stirred at room temperature for 16 hours. The reaction was quenched with water and extracted with dichloromethane. The organic layer was dried over anhydrous $Na_2SO_4$, filtered and evaporated to give a pale yellow solid, that was purified by flash chromatography using dichloromethane/methanol (99/1 to 95/5) to afford 70 mg (29% yield) of the title compound as a mixture of diastereomers. $^1$H-NMR (500 MHz, $CDCl_3$) δ 1.39–1.45 (m, 3H), 2.60–2.80 (m, 2H), 2.80–3.10 (m, 1H), 3.12–3.32 (m, 4H), 4.20–4.62 (m, 2H), 4.70–4.88 (m, 2H), 5.25–5.45 (m, 1H), 6.65–6.95 (m, 3H), 7.20–7.50 (m, 5H), 7.61 (s, 1H), 7.72 (d, 1H). Analytical HPLC: 10.86 and 10.98 min. LC-MS ($ES^+$): m/e=607, 609 ($M+H^+$).

3-{2-[6-(3,5-Dichloro-4-hydroxy-benzoylamino)-2-methyl-3,7-dioxo-[1,2]diazepan-1-yl]-propionylamino}-4-oxo-butyric acid (20) was prepared from N-{2-[1-(2-benzyloxy-5-oxo-tetrahydro-furan-3-ylcarbamoyl)-ethyl]-1-methyl-3,7-dioxo-[1,2]diazepan-4-yl}-3,5-dichloro-4-hydroxy-benzamide (19) (28 mg, 0.046 mmol) by the method used to prepare 11a, affording 17 mg (71% yield) of the title compound. $^1$H-NMR (500 MHz, $CDCl_3/CD_3OD$= 0.5 mL/3 drops) δ 1.20–1.50 (m, 3H), 1.90–2.10 (m, 1H), 2.25–2.85 (m, 4H), 3.10–3.40 (m, 3H), 4.05–4.50 (m, 1H), 4.55–4.65 (m, 1H), 4.75–5.05 (m, 2H), 7.72–7.76 (m, 2H). Analytical HPLC: 7.51 min. LC-MS ($ES^+$): m/e=517, 519 ($M+H^+$).

EXAMPLE 7

Compound 27 was prepared as described below:

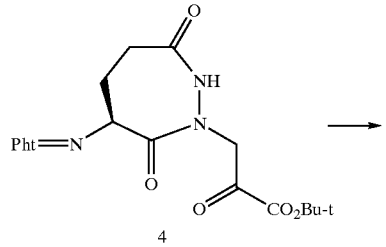

4

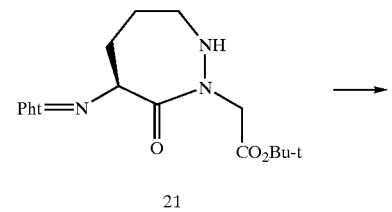

21

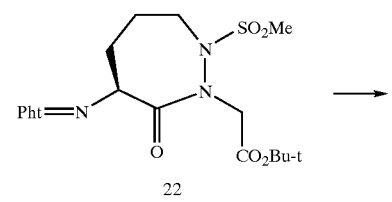

22

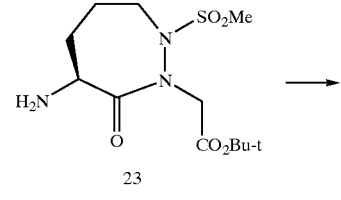

23

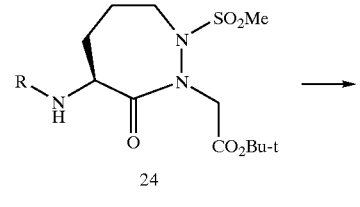

24

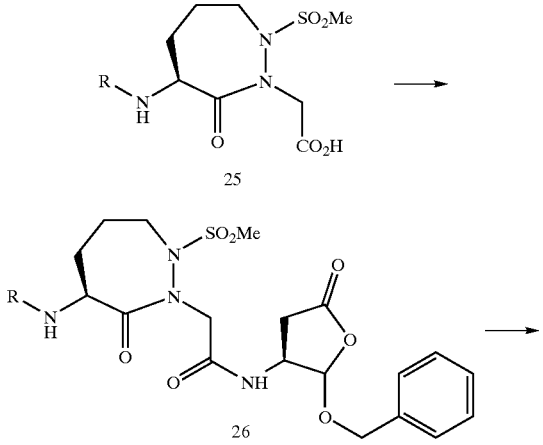

25

26

-continued

[Structure 27: R-NH-[7-membered diazepanone ring with N-SO2Me and N-CH2-C(O)-NH-CH(CO2H)-CHO substituent]]

| Compounds | R |
|---|---|
| 24 | |
| 25 | |
| 26a | [3,5-dichloro-4-allyloxy-benzoyl group] |
| 26b | |
| 27 | [3,5-dichloro-4-hydroxy-benzoyl group] |

Preparation of [6-(1,3-Dioxo-1,3-dihydro-isoindol-2-yl)-7-oxo-[1,2]diazepan-1-yl]-acetic acid tert-butyl ester (21). To a solution of [6-(1,3-dioxo-1,3-dihydro-isoindol-2-yl)-3,7-dioxo-[1,2]diazepan-1-yl]-acetic acid tert-butyl ester (4) (775 mg, 2.0 mmol) in THF (4 mL) was added borane-THF complex in THF (1M, 4 mL). The reaction was stirred at 0° C. for 30 min then at room temperature for 3 hours. The mixture was diluted with ice-water (60 mL), extracted with ethyl acetate (60 mL×3). The combined organic layers were dried over anhydrous $Na_2SO_4$, filtered and evaporated in vacuo to give a solid, that was purified by flash chromatography using hexane/ethyl acetate (95/5 to 70/30) to afford 585 mg (78% yield) of the title compound. $^1$H-NMR (500 MHz, $CDCl_3$) δ 1.43 (s, 9H), 1.78–1.90 (m, 1H), 2.00–2.15 (m, 2H), 2.65–2.78 (m, 1H), 2.95–3.07 (m, 1H), 3.22–3.30 (m, 1H), 3.85–3.92 (d, 1H), 4.30–4.42 (m, 2H), 5.39–5.42 (m, 1H), 7.62–7.71 (m, 2H), 7.79–7.86 (m, 2H). Analytical HPLC: 7.86 min. LC-MS (ES$^+$): m/e=374 (M+H$^+$).

Preparation of [6-(1,3-Dioxo-1,3-dihydro-isoindol-2-yl)-2-methanesulfonyl-7-oxo-[1,2]diazepan-1-yl]-acetic acid tert-butyl ester (22). To a solution of [6-(1,3-dioxo-1,3-dihydro-isoindol-2-yl)-7-oxo-[1,2]diazepan-1-yl]-acetic acid tert-butyl ester (21) (155 mg, 0.42 mmol), triethylamine (0.5 mL) and 4-N,N-dimethylaminopyridine (DMAP) (101 mg, 0.50 mmol) in dichloromethane was added dropwise methanesulfonyl chloride (95 mg, 0.83 mmol). The mixture was stirred at 0° C. for 5 min then at room temperature for 16 hours. The mixture was quenched with water, extracted with dichloromethane. The organic solution was washed with water then brine, dried over anhydrous $Na_2SO_4$, filtered and purified by flash chromatography using dichloromethane/ethyl acetate (99/1 to 95/5) to afford 154 mg (82% yield) of the title compound. $^1$H-NMR (500 MHz, $CDCl_3$) δ 1.47 (s, 9H), 2.05–2.21 (m, 2H), 2.83–2.87 (m, 1H), 3.27 (s, 3H), 3.53–3.58 (m, 1H), 4.07–4.11 (d, 1H), 4.29–4.33 (m, 1H), 4.50–4.53 (d, 1H), 5.42–5.44 (m, 1H), 7.70–7.85 (m, 4H). Analytical HPLC: 12.27 min. LC-MS (ES$^+$): m/e=452 (M+H$^+$).

(6-Amino-2-methanesulfonyl-7-oxo-[1,2]diazepan-1-yl)-acetic acid tert-butyl ester (23) was prepared from [6-(1,3-dioxo-1,3-dihydro-isoindol-2-yl)-2-methanesulfonyl-7-oxo-[1,2]diazepan-1-yl]-acetic acid tert-butyl ester (22) by the method used to prepare 6a to afford 95 mg (89% yield) of the title compound. $^1$H-NMR (500 MHz, $CDCl_3$) δ 1.48 (s, 9H), 1.66–1.71 (m, 1H), 1.83–1.87 (m, 1H), 1.94–198 (m, 1H), 2.09–2.13 (m, 1H), 3.07 (s, 3H), 3.45–3.51 (m, 1H), 3.87–3.91 (d, 1H), 4.00–4.11 (m, 2H), 4.59–4.63 (d, 1H). Analytical HPLC: 5.87 min. LC-MS (ES$^+$): m/e=322 (M+H$^+$).

[6-(4-Allyloxy-3,5-dichloro-benzoylamino)-2-methanesulfonyl-7-oxo-[1,2]diazepan-1-yl]-acetic acid tert-butyl ester (24) was prepared from (6-amino-2-methanesulfonyl-7-oxo-[1,2]diazepan-1-yl)-acetic acid tert-butyl ester (23) and 3,5-dichloro-4-allyloxybenzoylic acid by the method and chromatography used to prepare 7c to afford 193 mg (87% yield) of the title compound. $^1$H-NMR (500 MHz, $CDCl_3$) δ 1.50 (s, 9H), 1.78–1.93 (m, 2H), 2.22–2.25 (m, 2H), 3.16 (s, 3H), 3.44–3.52 (m, 1H), 4.03–4.06 (d, 1H), 4.22–4.25 (d, 1H), 4.60–4.64 (m, 3H), 5.11–5.13 (m, 1H), 5.28–5.29 (d, 1H), 5.40–5.44 (m, 1H), 6.10–6.16 (m, 1H), 7.21–7.30 (m, 1H), 7.75 (s, 2H). Analytical HPLC: 7.39 min. LC-MS (ES$^+$): m/e=550, 552 (M+H$^+$).

[6-(4-Allyloxy-3,5-dichloro-benzoylamino)-2-methanesulfonyl-7-oxo-[1,2]diazepan-1-yl]-acetic acid (25) was prepared from [6-(4-allyloxy-3,5-dichloro-benzoylamino)-2-methanesulfonyl-7-oxo-[1,2]diazepan-1-yl]-acetic acid tert-butyl ester (24) by the method used to prepare 8a to afford 173 mg (100% yield) of the title compound. $^1$H-NMR (500 MHz, $CDCl_3$) δ 1.74–1.77 (m, 1H), 1.91–1.93 (m, 1H), 2.22–2.25 (m, 2H), 3.19 (s, 3H), 3.39–3.44 (m, 1H), 4.24–4.28 (m, 2H), 4.61–4.63 (m, 2H), 4.71–4.75 (d, 1H), 5.12–5.15 (m, 1H), 5.28–5.31 (m, 1H), 5.40–5.44 (m, 1H), 6.10–6.16 (m, 1H), 7.31–7.33 (d, 1H), 7.79 (s, 2H). Analytical HPLC: 5.70 min. LC-MS (ES$^+$): m/e=494, 496 (M+H$^+$).

4-Allyloxy-N-{2-[(2-benzyloxy-5-oxo-tetrahydro-furan-3-ylcarbamoyl)-methyl]-1-methanesulfonyl-3-oxo-[1,2]diazepan-4-yl}-3,5-dichloro-benzamide (26a) was prepared from [6-(4-allyloxy-3,5-dichloro-benzoylamino)-2-methanesulfonyl-7-oxo-[1,2]diazepan-1-yl]-acetic acid (25) and (2-benzyloxy-5-oxo-tetrahydro-furan-3-yl)-carbamic acid allyl ester (9, a mixture of diastereomers) by the method and chromatography used to prepare 10a to afford 178 mg (74% yield) of the title compound as a mixture of diastereomers. $^1$H-NMR (500 MHz, $CDCl_3$) δ 1.58–1.70 (m, 2H), 1.89–1.97 (m, 1H), 2.20–2.32 (m, 2H), 2.40–2.60 (m, 1H), 2.86–3.05 (m, 1H), 3.28–3.40 (m, 4H), 4.05–4.15 (m, 2H), 4.30–4.37 (m, 1H), 4.42–4.48 (m, 0.5H), 4.60–4.66 (m, 3H), 4.66–4.71 (m, 0.5H), 4.78–4.88 (m, 1H), 5.05–5.15 (m, 1H), 5.28–5.31 (d, 1H), 5.40–5.44 (m, 1H), 6.07–6.18 (m, 1H), 6.75–7.15 (m, 1H), 7.25–7.38 (m, 3H), 7.43–7.49 (m, 1H), 7.52–7.58 (m, 0.5H), 7.65–7.70 (m, 2H), 7.78 (s, 0.5H). Analytical HPLC (cyano column): 7.12 min. LC-MS (ES$^+$): m/e=683, 685 (M+H$^+$).

Preparation of N-(2-[(2-Benzyloxy-5-oxo-tetrahydro-furan-3-ylcarbamoyl)-methyl]-1-methanesulfonyl-3-oxo-[1,2]diazepan-4-yl)-3,5-dichloro-4-hydroxy-benzamide (26b). 4-Allyloxy-N-{2-[(2-benzyloxy-5-oxo-tetrahydro-furan-3-ylcarbamoyl)-methyl]-1-methanesulfonyl-3-oxo-[1,2]diazepan-4-yl}-3,5-dichloro-benzamide (26a) (178 mg, 0.26 mmol) in dichloromethane (6 mL) was treated with DMBA (45 mg, 0.29 mmol) and Pd(PPh₃)₄ (20 mg, 0.017 mmol) at room temperature for 16 hours. The mixture was diluted with dichloromethane (40 mL), washed with water three times. The organic layer was dried over anhydrous Na₂SO₄, filtered and evaporated to give a pale yellow solid, that was purified by flash chromatography using dichloromethane/methanol (99.2/0.8 to 97.5/2.5) to afford 78 mg (47% yield) of syn diastereomer (higher Rf) of the title compound and 59 mg (35% yield) of anti diastereomer (lower Rf). ¹H-NMR (500 MHz, CDCl₃) for the syn diastereomer: δ 1.60–1.70 (m, 1H), 1.88–1.91 (m, 1H), 2.22–2.32 (m, 2H), 2.48–2.58 (m, 1H), 2.84–2.90 (m, 1H), 3.00 (s, 3H), 3.27–3.40 (m, 1H), 4.05–4.18 (m, 2H), 4.22–4.35 (m, 1H), 4.55–4.80 (m, 2H), 4.86–4.89 (d, 1H), 5.10–5.15 (m, 1H), 5.59–5.61 (d, 1H), 6.75–6.77 (d, 1H), 7.05–7.07 (d, 1H), 7.25–7.37 (m, SH), 7.70 (s, 2H); and for the anti diastereomer: δ 1.60–1.80 (m, 1H), 1.85–1.95 (m, 1H), 2.20–2.39 (m, 2H), 2.39–2.50 (m, 1H), 3.00–3.10 (m, 1H), 3.12 (s, 3H), 3.28–3.42 (m, 1H), 4.05–4.15 (m, 2H), 4.28–4.47 (m, 2H), 4.56–4.62 (m, 1H), 4.77–4.83 (d, 1H), 5.10–5.20 (m, 1H), 5.43 (s, 1H), 6.93–6.94 (d, 1H), 7.09–7.11 (d, 1H), 7.25–7.39(m, SH), 7.80 (s, 2H). Analytical HPLC: 11.13 and 11.36 min. LC-MS (ES⁺) for the mixture of diastereomers: m/e=643, 645 (M+H⁺).

Preparation of 3-{2-[6-(3,5-Dichloro-4-hydroxy-benzoylamino)-2-methanesulfonyl-7-oxo-[1,2]diazepan-1-yl]-acetylamino}-4-oxo-butyric acid (27). N-{2-[(2-Benzyloxy-5-oxo-tetrahydro-furan-3-ylcarbamoyl)-methyl]-1-methanesulfonyl-3-oxo-[1,2]diazepan-4-yl}-3,5-dichloro-4-hydroxy-benzamide (26b) was stirred in CH₃CN (0.5 mL) and 2N HCl (1 mL) for 7 hours. The solution was concentrated in vacuo to half of the volume and extracted with ether (2 mL×4). The combined ether layers was diluted with ethyl acetate/hexane (1/9, 3 mL), washed with 1M Na₂CO₃ (2 mL). The aqueous solution was washed with ethyl acetate/hexane (1/9, 2 mL×2), acidified with 6N HCl to pH~3, extracted with ethyl acetate (1.5 mL×3). The combined extracts were dried over anhydrous Na₂SO₄, filtered and concentrated to dryness in vacuo to afford 20 mg (47% yield) of the title compound. ¹H-NMR (500 MHz, CDCl₃ +CD₃OD) δ 0.75–0.90 (m, 1H), 1.18–1.30 (m, 3H), 1.67–1.88 (m, 1H), 1.93–2.30 (m, 2H), 2.40–2.61 (m, 1H), 3.10–3.16 (m, 3H), 3.95–4.30 (m, 2H), 4.30–4.50 (m, 1H), 5.00–5.08 (d, 1H), 7.81 (s, 2H). Analytical HPLC: 8.10 min. LC-MS (ES⁺): m/e=553, 555 (M+H⁺).

Analytical HPLC conditions:
  Column: Microsorb™ C-18, 8μ, 4.6×150 mm (unless noted).
  Solvent A: 0.1% TFA/1% MeCN/98.9% water
  Solvent B: 0.1% TFA/99.9% MeCN
  Gradient: A to B over 20 min at a flow rate of 1 mL/min

EXAMPLE 8

TABLE 1

| | In Vitro Data | | | | |
|---|---|---|---|---|---|
| Cmp | ICE Caspase-1 Ki (nM) | CPP32 Caspase-3 Ki (nM) | Flice Caspase-8 Ki (nM) | PBMC IC50 (nM) | Whole Blood IC50 (nM) |
| 11a | 101 | | | 1400 | 7300 |
| 11b | 120 | | | 1500 | 5800 |
| 11c | 16 | 22200 | 1500 | 420 | 1450 |

TABLE 1-continued

| | In Vitro Data | | | | |
|---|---|---|---|---|---|
| Cmp | ICE Caspase-1 Ki (nM) | CPP32 Caspase-3 Ki (nM) | Flice Caspase-8 Ki (nM) | PBMC IC50 (nM) | Whole Blood IC50 (nM) |
| 20 | 0.9 | | | 540 | 830 |
| 27 | 17 | | | 1000 | 1900 |

Insofar as the compounds of this invention are able to inhibit caspases, particularly ICE, in vitro and furthermore, may be delivered orally to mammals, they are of evident clinical utility for the treatment of IL-1-, apoptosis-, IGIF-, and IFN-γ-mediated diseases.

While we have described a number of embodiments of this invention, it is apparent that our basic constructions may be altered to provide other embodiments which utilize the products and processes of this invention.

What is claimed is:
1. A compound represented by formula (I):

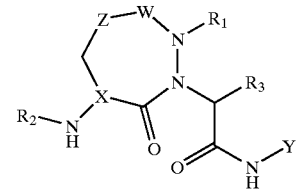

wherein:
Y is:

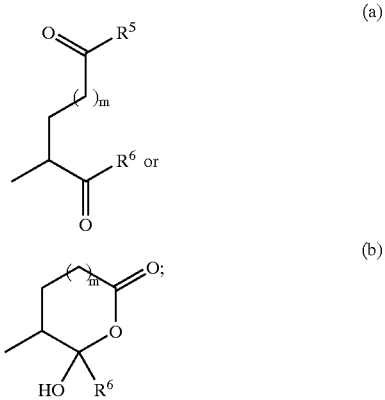

m is 0 or 1;
W is —CH₂—, —C(O)—;
X is —C(H)—, —C(R⁸)—;
Z is —CH₂—;
each R¹ is independently —H, —C(O)R⁸, —S(O)₂R⁸, —S(O)R⁸, —R²¹, -alkyl-R²¹, -alkenyl-R²¹, -alkynyl-R²¹, -alkyl;
R² is —C(O)R⁸, —C(O)C(O)R⁸, —S(O)₂R⁸, —S(O)R⁸, —C(O)OR⁸, —C(O)N(H)R⁸, —S(O)₂N(H)-R⁸, —S(O)N(H)-R⁸, —C(O)C(O)N(H)R⁸, —C(O)CH=CHR⁸, —C(O)CH₂OR⁸, —C(O)CH₂N(H)R⁸, —C(O)N(R⁸)₂, —S(O)₂N(R⁸)₂, —S(O)N(R⁸)₂, —C(O)C(O)N(R⁸)₂, —C(O)CH₂N(R⁸)₂, —CH₂—R⁸, —CH₂-alkenyl-R⁸, or —CH₂-alkynyl-R⁸;
R³ is —H, —R²¹, -alkyl-R²¹, -alkenyl-R²¹, -alkynyl-R²¹, alkyl, or an amino acid side chain;

each R⁴ is independently —OH, —F, —Cl, —Br, —I, —NO₂, —CN, —NH₂, —CO₂H, —C(O)NH₂, —N(H)C(O)H, —N(H)C(O)NH₂, -alkyl, -cycloalkyl, -perfluoroalkyl, —O-alkyl, —(H)alkyl, —N(alkyl)₂, —C(O)N(H)alkyl, —C(O)N(alkyl)₂, —N(H)C(O)alkyl, —N(H)C(O)N(H)alkyl, —N(H)C(O)N(alkyl)₂, —S-alkyl, —S(O)₂alkyl, —S(O)alkyl, —C(O)alkyl, —CH₂NH₂, —CH₂N(H)alkyl, —CH₂N(alkyl)₂, or —N(H)C(O)Oalkyl;

R⁵ is —OH, —OR⁸, —N(H)OH, or —N(H)SO₂R⁸;

R⁶ is —H, —CH₂OR⁹, —CH₂SR¹⁰, —CH₂N(H)R⁹, —CH₂N(R⁹)R¹¹, —CHN₂, —CH₂F, —CH₂Cl, —CH₂Br, —CH₂I, —C(O)N(R¹¹)₂, —R¹³, or —R¹⁴;

each R⁸ is independently -alkyl, -cycloalkyl, -aryl, -heteroaryl, -heterocyclyl, -alkylcycloalkyl -alkylaryl, -alkylheteroaryl, or -alkylheterocyclyl;

R⁹ is —H, —C(O)aryl, —C(O)heteroaryl, —C(O)alkylaryl, —C(O)alkylheteroaryl, -alkylaryl, -alkylheteroaryl, -aryl, -heteroaryl, or —P(O)(R¹⁵)₂;

R¹⁰ is -alkylaryl or -alkylheteroaryl;

each R¹¹ is independently —H, -alkyl, -aryl, -heteroaryl, -cycloalkyl, -alkylaryl, or -alkylheteroaryl;

R¹³ is -alkylaryl or -alkylheteroaryl;

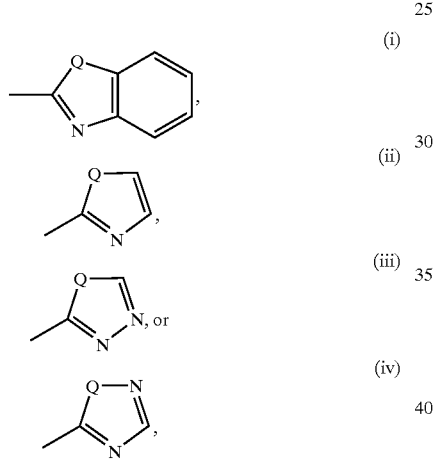

wherein Q is —O— or —S—, any hydrogen atom in (i) is optionally replaced with —R¹⁷, and any hydrogen atom in (ii), (iii), and (iv) is optionally replaced with —R¹⁷, —R¹⁸ or -alkyl-R¹⁸;

each R¹⁵ is independently —H, —OH, -alkyl, -aryl, -heteroaryl, -cycloalkyl, -alkylaryl, -alkylheteroaryl, —O-alkyl, —O-aryl, —O-heteroaryl, —O-alkylaryl, or —O-alkylheteroaryl;

each R¹⁷ is independently —OH, —F, —Cl, —Br, —I, —NO₂, —CN, —NH₂, —CO₂H, —C(O)NH₂, —N(H)C(O)H, —N(H)C(O)NH₂, —SO₂NH₂, —C(O)H, -alkyl, -cycloalkyl, -perfluoroalkyl, —O-alkyl, —N(H)alkyl, —N(alkyl)₂, —CO₂alkyl, —C(O)N(H)alkyl, —C(O)N(alkyl)₂, —N(H)C(O)alkyl, —N(H)C(O)N(H)alkyl, —N(H)C(O)N(alkyl)₂, —S(O)₂N(H)alkyl, —S(O)N(H)alkyl, —S(O)₂N(alkyl)₂, —S(O)N(alkyl)₂, —S-alkyl, —S(O)₂alkyl, —S(O)alkyl, or —C(O)alkyl;

each R¹⁸ is independently -aryl, -heteroaryl, -alkylaryl, -alkylheteroaryl, —O-aryl, —O-heteroaryl, —O-alkylaryl, —O-alkylheteroaryl, —N(H)aryl, —N(aryl)₂, —N(H)heteroaryl, —N(heteroaryl)₂, —N(H)alkylaryl, —N(alkylaryl)₂, —N(H)alkylheteroaryl, —N(alkylheteroaryl)₂, —S-aryl, —S-heteroaryl, —S-alkylaryl, —S-alkylheteroaryl, —C(O)aryl, —C(O)heteroaryl, —C(O)alkylaryl, —C(O)alkylheteroaryl, —CO₂aryl, —CO₂heteroaryl, —CO₂alkylaryl, —CO₂alkylheteroaryl, —C(O)N(H)aryl, —C(O)N(aryl)₂, —C(O)N(H)heteroaryl, —C(O)N(heteroaryl)₂, —C(O)N(H)alkylaryl, —C(O)N(alkylaryl)₂, —C(O)N(H)alkylheteroaryl, —C(O)N(alkylheteroaryl)₂, —S(O)₂-aryl, —S(O)-aryl, —S(O)₂-heteroaryl, —S(O)-heteroaryl, —S(O)₂-alkylaryl, —S(O)-alkylaryl, —S(O)₂-alkylheteroaryl, —S(O)-alkylheteroaryl, —S(O)₂N(H)-aryl, —S(O)N(H)-aryl, —S(O)₂NH-heteroaryl, —S(O)NH-heteroaryl, —S(O)₂N(H)-alkylaryl, —S(O)N(H)-alkylaryl, —S(O)₂N(H)-alkylheteroaryl, —S(O)N(H)-alkylheteroaryl, —S(O)₂N(aryl)₂, —S(O)N(aryl)₂, —S(O)₂N(heteroaryl)₂, —S(O)N(heteroaryl)₂, —S(O)₂N(alkylaryl)₂, —S(O)N(alkylaryl)₂, —S(O)₂N(alkylheteroaryl)₂, —S(O)N(alkylheteroaryl)₂, —N(H)C(O)N(H)aryl, —N(H)C(O)N(H)heteroaryl, —N(H)C(O)N(H)alkylaryl, —N(H)C(O)N(H)alkylheteroaryl, —N(H)C(O)N(aryl)₂, —N(H)C(O)N(heteroaryl)₂, —N(H)C(O)N(alkylaryl)₂, or —N(H)C(O)N(alkylheteroaryl)₂;

each R²¹ is independently -aryl, -heteroaryl, cycloalkyl, or -heterocyclyl, wherein a hydrogen atom bound to any carbon atom is optionally replaced by R⁴ and a hydrogen atom bound to any nitrogen atom is optionally replaced by R²;

each heterocyclyl is a mono-or polycyclic ring system which contains 1 to 15 carbon atoms and 1 to 4 heteroatoms selected from S, N, or O, in which the mono- or polycyclic ring system may optionally contain unsaturated bonds but is not aromatic;

each cycloalkyl is a mono- or polycyclic, non-aromatic, hydrocarbon ring system which may optionally contain unsaturated bonds in the ring system;

each heteroaryl is a mono- or polycyclic ring system which contains 1 to 15 carbon atoms and 1 to 4 heteroatoms selected from S, N, or O, and in which at least one ring of the ring system is aromatic; and each amino acid side chain is the substituent bound to the α-carbon of a natural or non-natural α-amino acid.

2. A compound represented by formula (I):

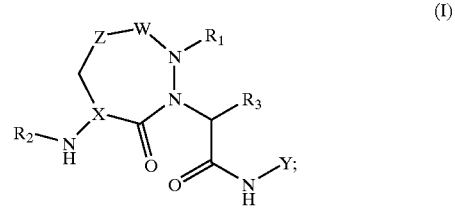

Y is:

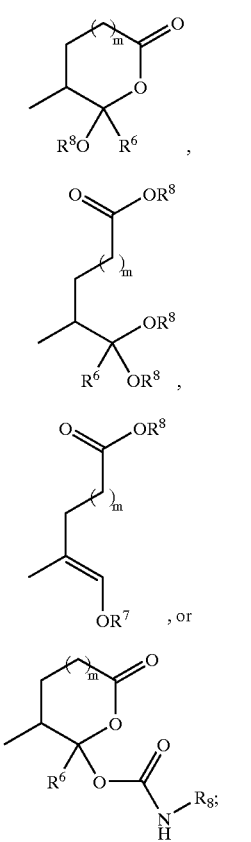

(c)

(d)

(e)

(f)

m is 0 or 1;
W is —CH₂—, —C(O)—;
X is —C(H)—, —C(R⁸)—;
Z is —CH₂—;
each $R^1$ is independently —H, —C(O)R⁸, —S(O)₂R⁸, —S(O)R⁸, —R²¹, -alkyl-R²¹, -alkenyl-R²¹, -alkynyl-R²¹, -alkyl;
$R^2$ is —C(O)R⁸, —C(O)C(O)R⁸, —S(O)₂R⁸, —S(O)R⁸, —C(O)OR⁸, —C(O)N(H)R⁸, —S(O)₂N(H)-R⁸, —S(O)N(H)-R⁸, —C(O)C(O)N(H)R⁸, —C(O)CH=CHR⁸, —C(O)CH₂OR⁸, —C(O)CH₂N(H)R⁸, —C(O)N(R⁸)₂, —S(O)₂N(R⁸)₂, —S(O)N(R⁸)₂, —C(O)C(O)N(R⁸)₂, —C(O)CH₂N(R⁸)₂, —CH₂—R⁸, —CH₂-alkenyl-R⁸, or —CH₂-alkynyl-R⁸;
$R^3$ is —H, —R²¹, -alkyl-R²¹, -alkenyl-R²¹, -alkynyl-R²¹, alkyl, or an amino acid side chain;
each $R^4$ is independently —OH, —F, —Cl, —Br, —I, —NO₂, —CN, —NH₂, —CO₂H, —C(O)NH₂, —N(H)C(O)H, —N(H)C(O)NH₂, -alkyl, -cycloalkyl, -perfluoroalkyl, —O-alkyl, —N(H)alkyl, —N(alkyl)₂, —C(O)N(H)alkyl, —C(O)N(alkyl)₂, —N(H)C(O)alkyl, —N(H)C(O)N(H)alkyl, —N(H)C(O)N(alkyl)₂, —S-alkyl, —S(O)₂alkyl, —S(O)alkyl, —C(O)alkyl, —CH₂NH₂, —CH₂N(H)alkyl, —CH₂N(alkyl)₂, or —N(H)C(O)Oalkyl;
$R^6$ is —H, —CH₂OR⁹, —CH₂SR¹⁰, —CH₂N(H)R⁹, —CH₂N(R⁹)R¹¹, —CHN₂, —CH₂F, —CH₂Cl, —CH₂Br, —CH₂I, —C(O)N(R¹¹)₂, —R¹³, or —R¹⁴;
$R^7$ is —C(O)alkyl, —C(O)cycloalkyl, —C(O)alkyenyl, —C(O)alkylaryl, —C(O)alkylheteroaryl, —C(O)heterocycle, or —C(O)alkylheterocycle;

each $R^8$ is independently -alkyl, -cycloalkyl, -aryl, -heteroaryl, -heterocyclyl, -alkylcycloalkyl -alkylaryl, -alkylheteroaryl, or -alkylheterocyclyl;
$R^9$ is —H, —C(O)aryl, —C(O)heteroaryl, —C(O)alkylaryl, —C(O)alkylheteroaryl, -alkylaryl, -alkylheteroaryl, -aryl, -heteroaryl, or —P(O)(R¹⁵)₂;
$R^{10}$ is -alkylaryl or -alkylheteroaryl;
each $R^{11}$ is independently —H, -alkyl, -aryl, -heteroaryl, -cycloalkyl, -alkylaryl, or -alkylheteroaryl;
$R^{13}$ is -alkylaryl or -alkylheteroaryl;

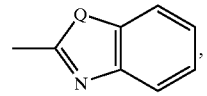

(i)

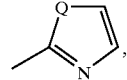

(ii)

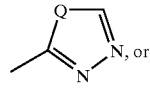

(iii)

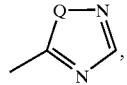

(iv)

wherein Q is —O— or —S—, any hydrogen atom in (i) is optionally replaced with —R¹⁷, and any hydrogen atom in (ii), (iii), and (iv) is optionally replaced with —R¹⁷, —R¹⁸ or -alkyl-R¹⁸;
each $R^{15}$ is independently —H, —OH, -alkyl, -aryl, -heteroaryl, -cycloalkyl, -alkylaryl, -alkylheteroaryl, —O-alkyl, —O-aryl, —O-heteroaryl, —O-alkylaryl, or —O-alkylheteroaryl;
each $R^{17}$ is independently —OH, —F, —Cl, —Br, —I, —NO₂, —CN, —NH₂, —CO₂H, —C(O)NH₂, —N(H)C(O)H, —N(H)C(O)NH₂, —SO₂NH₂, —C(O)H, -alkyl, -cycloalkyl, -perfluoroalkyl, —O-alkyl, —N(H)alkyl, —N(alkyl)₂, —CO₂alkyl, —C(O)N(H)alkyl, —C(O)N(alkyl)₂, —N(H)C(O)alkyl, —N(H)C(O)N(H)alkyl, —N(H)C(O)N(alkyl)₂, —S(O)₂N(H)alkyl, —S(O)N(H)alkyl, —S(O)₂N(alkyl)₂, —S(O)N(alkyl)₂, —S-alkyl, —S(O)₂alkyl, —S(O)alkyl, or —C(O)alkyl;
each $R^{18}$ is independently -aryl, -heteroaryl, -alkylaryl, -alkylheteroaryl, —O-aryl, —O-heteroaryl, —O-alkylaryl, —O-alkylheteroaryl, —N(H)aryl, —N(aryl)₂, —N(H)heteroaryl, —N(heteroaryl)₂, —N(H)alkylaryl, —N(alkylaryl)₂, —N(H)alkylheteroaryl, —N(alkylheteroaryl)₂, —S-aryl, —S-heteroaryl, —S-alkylaryl, —S-alkylheteroaryl, —C(O)aryl, —C(O)heteroaryl, —C(O)alkylaryl, —C(O)alkylheteroaryl, —CO₂aryl, —CO₂heteroaryl, —CO₂alkylaryl, —CO₂alkylheteroaryl, —C(O)N(H)aryl, —C(O)N(aryl)₂, —C(O)N(H)heteroaryl, —C(O)N(heteroaryl)₂, —C(O)N(H)alkylaryl), —C(O)N(alkylaryl)₂, —C(O)N(H)alkylheteroaryl, —C(O)N(alkylheteroaryl)₂, —S(O)₂-aryl, —S(O)-aryl, —S(O)₂-heteroaryl, —S(O)-heteroaryl, —S(O)₂-alkylaryl, —S(O)- alkylaryl, —S(O)₂-alkylheteroaryl, —S(O)-alkylheteroaryl, —S(O)₂N(H)-aryl, —S(O)N(H)-aryl, —S(O)₂NH-heteroaryl, —S(O)NH-heteroaryl, —S(O)₂N(H)-alkylaryl, —S(O)N(H)-alkylaryl, —S(O)₂N(H)-alkylheteroaryl, —S(O)N(H)-alkylheteroaryl, —S(O)₂N(aryl)₂, —S(O)N(aryl)₂, —S(O)₂N(heteroaryl)₂, —S(O)N(heteroaryl)₂, —S(O)₂N(alkylaryl)₂, —S(O)N(alkylaryl)₂, —S(O)₂N(alkylheteroaryl)₂, —S(O)N(alkylheteroaryl)₂, —N(H)C(O)N(H)aryl, —N(H)C(O)N(H)heteroaryl, —N(H)C(O)N(H)alkylaryl, —N(H)C(O)N(H)alkylheteroaryl, —N(H)C(O)N(aryl)₂, —N(H)C(O)N(heteroaryl)₂, —N(H)C(O)N(alkylaryl)₂, or —N(H)C(O)N(alkylheteroaryl)₂;

each $R^{21}$ is independently -aryl, -heteroaryl, cycloalkyl, or -heterocyclyl, wherein a hydrogen atom bound to any carbon atom is optionally replaced by $R^4$ and a hydrogen atom bound to any nitrogen atom is optionally replaced by $R^2$;

each heterocyclyl is a mono-or polycyclic ring system which contains 1 to 15 carbon atoms and 1 to 4 heteroatoms selected from S, N, or O, in which the mono- or polycyclic ring system may optionally contain unsaturated bonds but is not aromatic;

each cycloalkyl is a mono- or polycyclic, non-aromatic, hydrocarbon ring system which may optionally contain unsaturated bonds in the ring system;

each heteroaryl is a mono- or polycyclic ring system which contains 1 to 15 carbon atoms and 1 to 4 heteroatoms selected from S, N, or O, and in which at least one ring of the ring system is aromatic; and each amino acid side chain is the substituent bound to the α-carbon of a natural or non-natural α-amino acid.

3. The compound according to any one of claims 1–2 wherein $R^1$ is aryl, heteroaryl, alkyl, alkylaryl, or alkylheteroaryl;

wherein each heteroaryl is a mono- or polycyclic ring system which contains 1 to 15 carbon atoms and 1 to 4 heteroatoms selected from S, N, or O, and in which at least one ring of the ring system is aromatic.

4. The compound according to claim 3, wherein $R^1$ is:

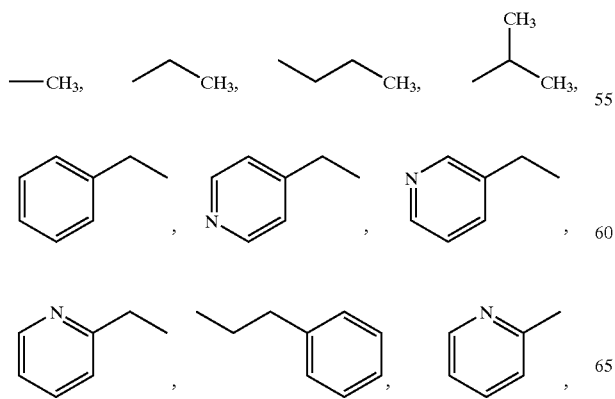

5. The compound according to any one of claims 1–2, wherein $R^2$ is:

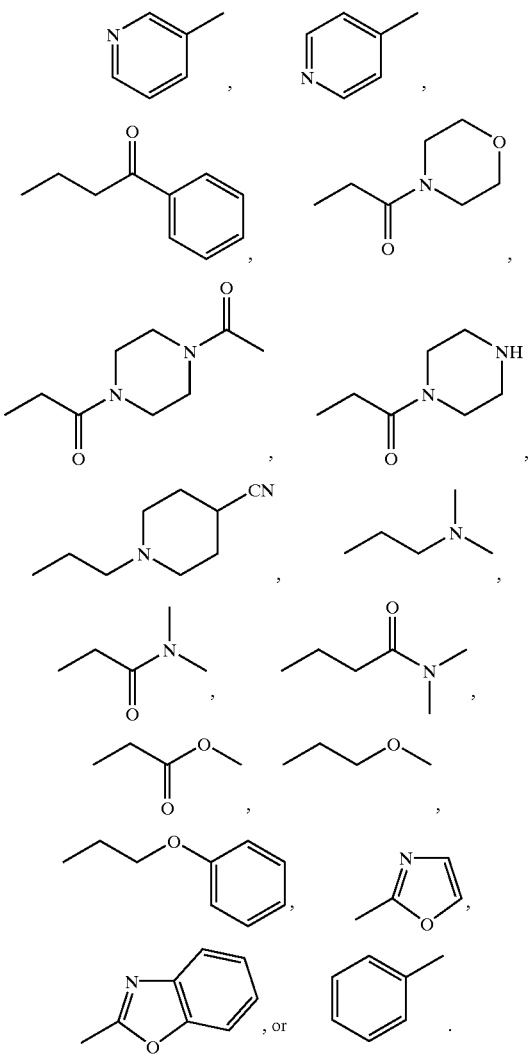

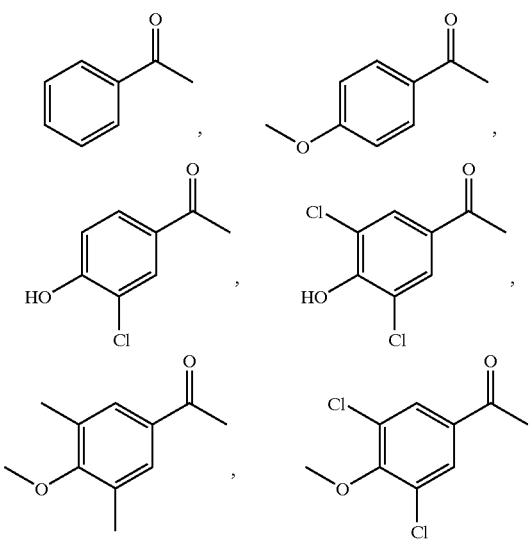

-continued

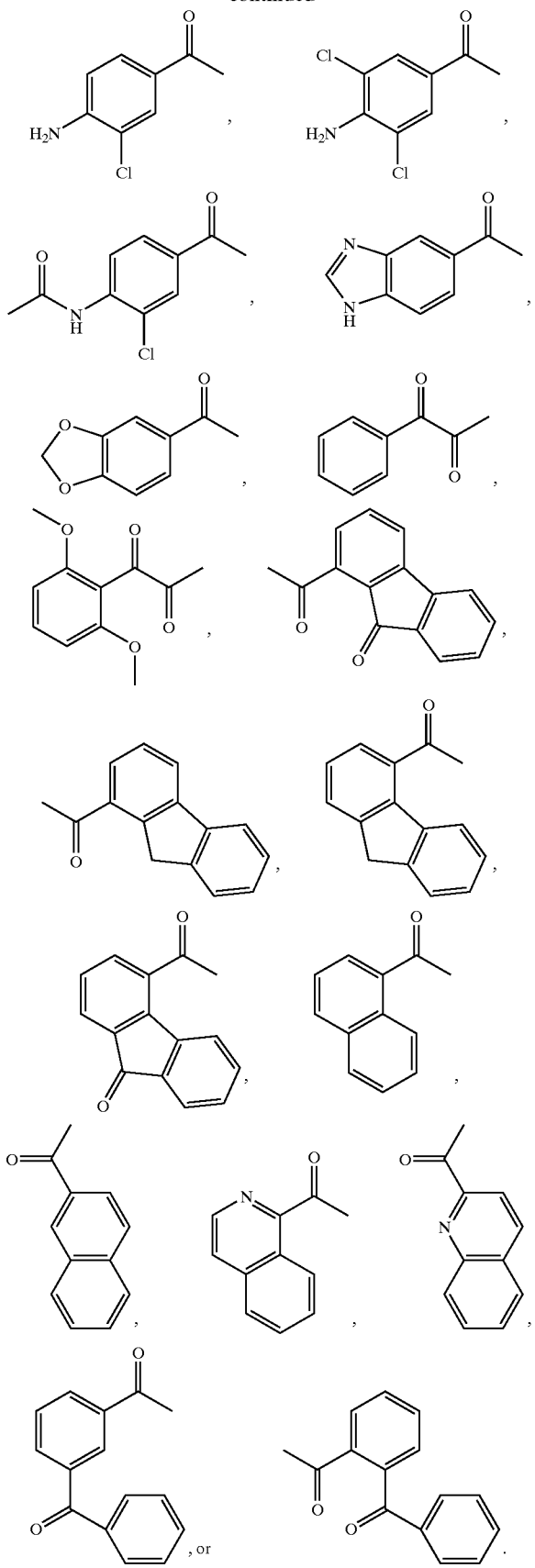

6. The compound according to any one of claims 1–2 wherein $R^3$ is an amino acid side chain, aryl, heteroaryl, alkyl, alkylaryl, or alkylheteroaryl;

wherein each heteroaryl is a mono- or polycyclic ring system which contains 1 to 15 carbon atoms and 1 to 4 heteroatoms selected from S, N, or O, and in which at least one ring of the ring system is aromatic; and each amino acid side chain is the substituent bound to the α-carbon of a natural or non-natural α-amino acid.

7. The compound according to claim 6 wherein $R^3$ is:

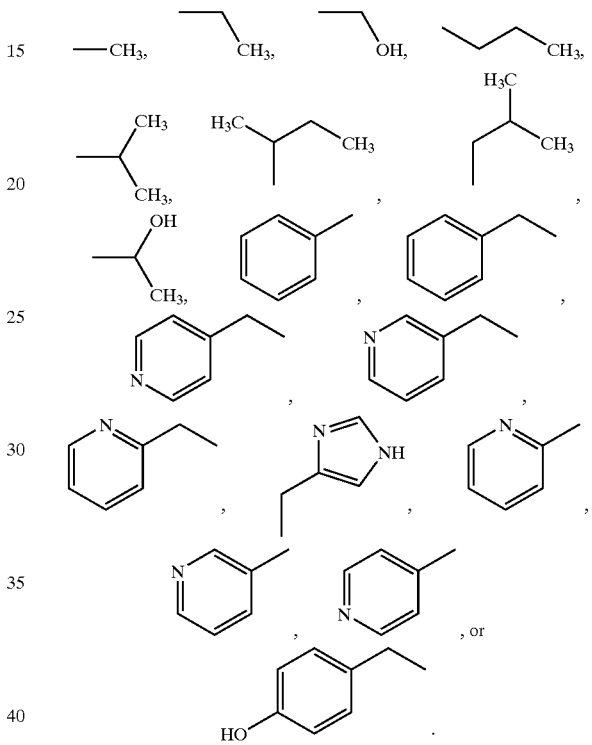

8. The compound according to any one of claims 1–2 wherein $R^6$ is —H.

9. The compound according to claim 2 wherein —$R^8$ is -alkyl, -alkylcycloalkyl, -aryl, -alkylaryl, or alkylheterocyclyl;

wherein each heterocyclyl is a mono-or polycyclic ring system which contains 1 to 15 carbon atoms and 1 to 4 heteroatoms selected from S, N, or O, in which the mono- or polycyclic ring system may optionally contain unsaturated bonds but is not aromatic; and each cycloalkyl is a mono- or polycyclic, non-aromatic, hydrocarbon ring system which may optionally contain unsaturated bonds in the ring system.

10. The compound according to claim 9, wherein Y is:

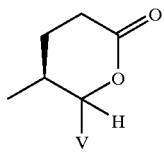

and V is:
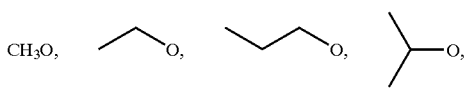
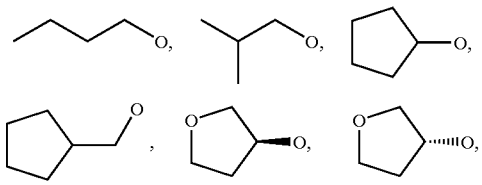
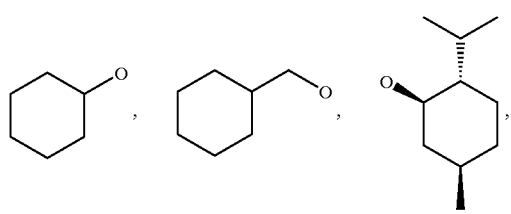
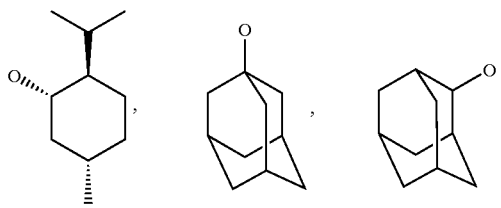
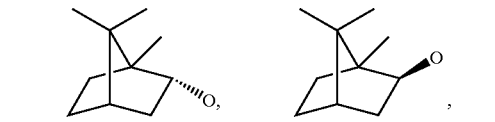
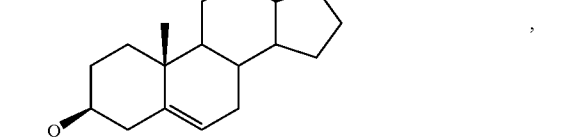
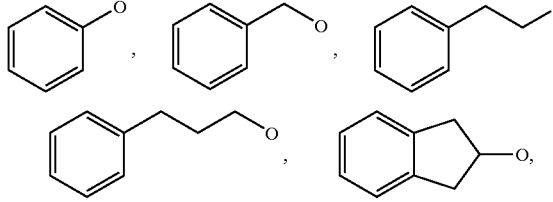
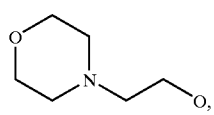
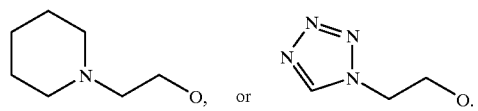
11. The compound according to claim 1 selected from the group consisting of:
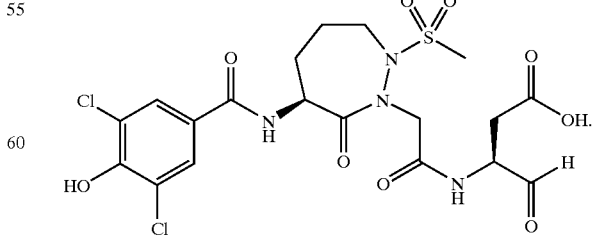
12. The compound according to claim 2 selected from the group consisting of:

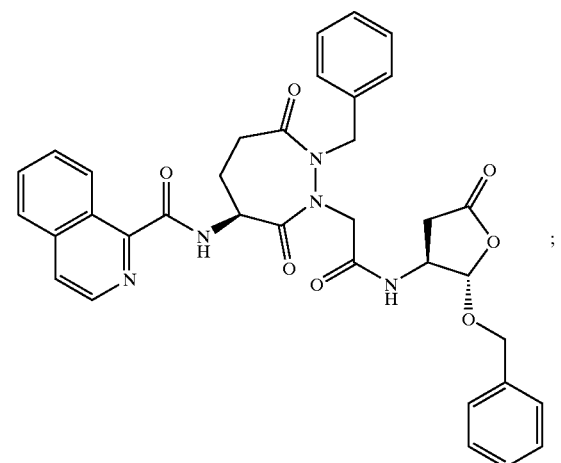

10a

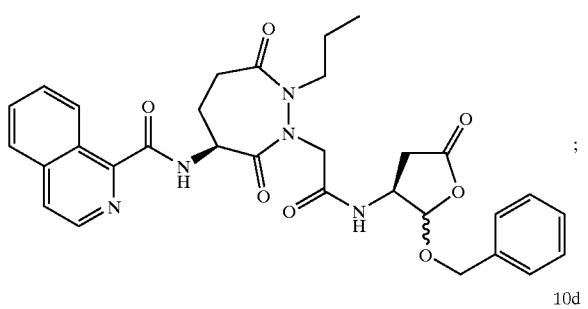

10b

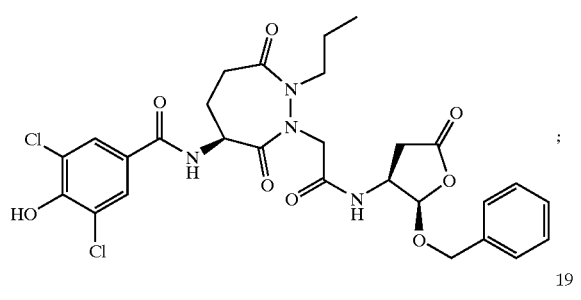

10d

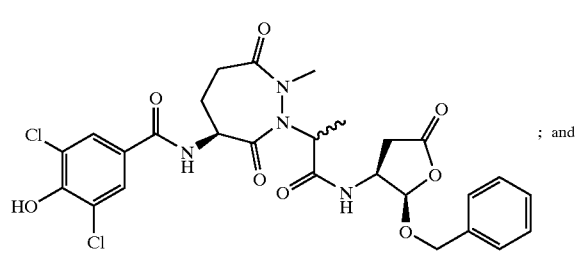

19

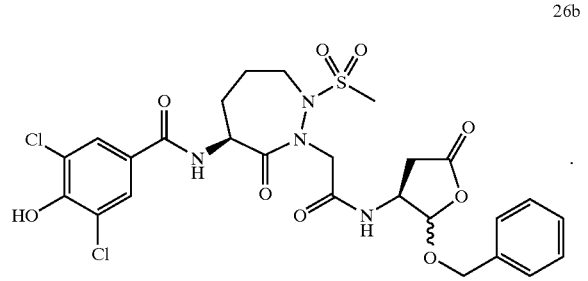

; and

26b

13. A pharmaceutical composition comprising:
a) a compound according to any one of claims 1–12; and
b) a pharmaceutically acceptable carrier, adjuvant or vehicle.

14. A method for treating a disease selected from an inflammatory disease, an infectious disease, inflammatory peritonitis, osteoarthritis, glomerulonephritis, rheumatoid arthritis, inflammatory bowel disease, psoriasis, graft vs host disease, sepsis, or septic shock in a patient comprising the step of administering to said patient a compound according to any one of claims 1–12 or a pharmaceutical composition according to claim 13.

15. The method according to claim 14, wherein the disease is rheumatoid arthritis, inflammatory bowel disease, inflammatory peritonitis, septic shock, osteoarthritis, or psoriasis.

16. A for preparing a compound represented by formula (V):

 (V)

wherein:

$R^{25}$ is:

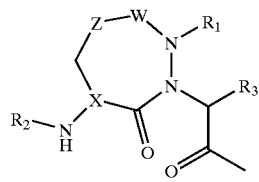

$R^{26}$ is:

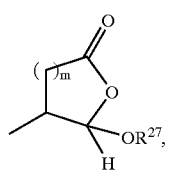 (a)

each $R^{27}$ is independently -alkyl, -cycloakyl, -aryl, -heteroaryl, -alkylaryl, -alkylheteroaryl, or -alkylheterocycle;

m is 0 or 1;

W is —CH$_2$—, —C(O)—;

X is —C(H)—, —C(R$^8$)—;

Z is —CH$_2$—;

each $R^1$ is independtenly —H, —C(O)R$^8$, —S(O)R$^8$, —R$^{21}$, -alkyl-R$^{21}$, -alkenyl-R$^{21}$, -alkynyl-R$^{21}$, -alkyl;

$R_2$ is —C(O)R$^8$, —C(O)C(O)R$^8$, —S(O)$_2$R$^8$, —S(O)R$^8$, —C(O)OR$^8$, —C(O)N(H)R$^8$, —S(O)$_2$N(H)-R$^8$, —S(O)N(H)-R$^8$, —C(O)C(O)N(H)R$^8$, —C(O)CH=CHR$^8$, —C(O)CH$_2$OR$^8$, —C(O(CH$_2$N(H)R$^8$, —C(O)N(R$^8$)$_2$, —S(O)$_2$N(R$^8$)$_2$, —S(O)N(R$^8$)$_2$, —C(O)C(O)N(R$^8$)$_2$, —C(O)CH$_2$N(R$^8$)$_2$, —CH$_2$—R$^8$, —CH$_2$-alkenyl-R$^8$, or —CH$_2$-alkynyl-R$^8$;

$R^3$ is —H, —R$^{21}$, -alkyl-R$^{21}$, -alkenyl-R$^{21}$, -alkynyl-R$^{21}$, alkyl, or an amino acid side chain;

each $R^4$ is independently —OH, —F, —Cl, —Br, —I, —NO$_2$, —CN, —NH$_2$, —CO$_2$H, —C(O)NH$_2$, —N(H)

C(O)H, —N(H)C(O)NH₂, -alkyl, -cycloalkyl, -perfluoroalkyl, —O-alkyl, —N(H)alkyl, —N(alkyl)₂, —C(O)N(H)alkyl, —C(O)N(alkyl)₂, —N(H)C(O)alkyl, —N(H)C(O)N(H)alkyl, —N(H)C(O)N(alkyl)₂, —S-aklyl, —S(O)₂alkyl, —S(O)alkyl, —C(O)alkyl, —CH₂NH₂, —CH₂N(H)alkyl, —CH₂N(alkyl)₂, or —N(H)C(O)O-alkyl;

each $R^8$ is independtly -alkyl, -cycloalkyl, -aryl, -heteroaryl, -heterocyclyl, -alkylcycloalkyl, -alkylaryl, -alkylheteroaryl, or alkylheterocyclyl;

each $R^{21}$ is independently -aryl, -heteroaryl, -cycloalkyl, or -heterocyclyl, wherein a hydrogen atom bound to any carbon atom is optionally replaced by $R^4$ and a hydrogen atom bound to any nitrogen atome is optionally replaced by $R^2$;

each hetrocyclyl is a mono-or polycyclic ring system which contains 1 to 15 carbon atoms and 1 to 4 heteroatoms selected from S, N, or O, in which the mono- or polycyclic ring system may optionally contain unsaturated bonds but is not aromatic;

each cycloalkyl is a mono- or plycyclic, non-aromatic, hydrocarbon ring system which may optionally contain unsaturated bonds in the ring system;

each heteroaryl is a mono- or plycyclic ring system which contains 1 to 15 carbon atoms and 1 to 4 heteroatoms selected from S, N, or O, and in which at least one ring of the ring system is aromatic; and each amino acid side chain is the substituent bound to the α-carbon of a natural or non-natural α-amino acid;

comprising the stgeps of:
a) reacting a compound represented by formula (VI): $R^{25}$—OH, wherein $R^{25}$ is as defined above, with a compound represented by formula (VII):

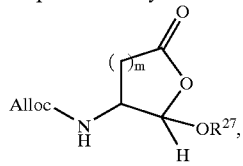

wherein $R^{27}$ is defined above, in the presence of an inert solvent, triphenylphospine, a nuclophilic scavenger, and palladium(0) at ambient temperature, and
b) adding to the mixture formed in step a), HOBT and EDC.

17. The process according to claim 16 wherein:
$R^1$ is aryl, heteroaryl, alkyl, alkylaryl, or alkylheteroaryl;
$R^2$ is:

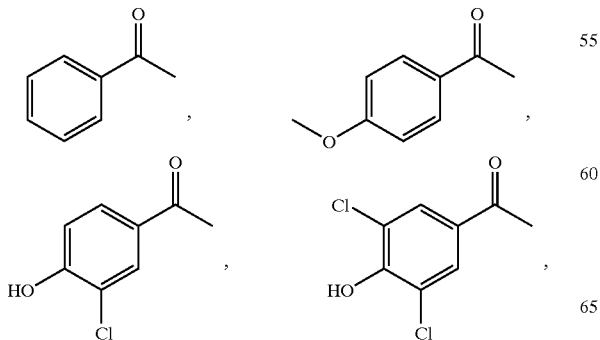

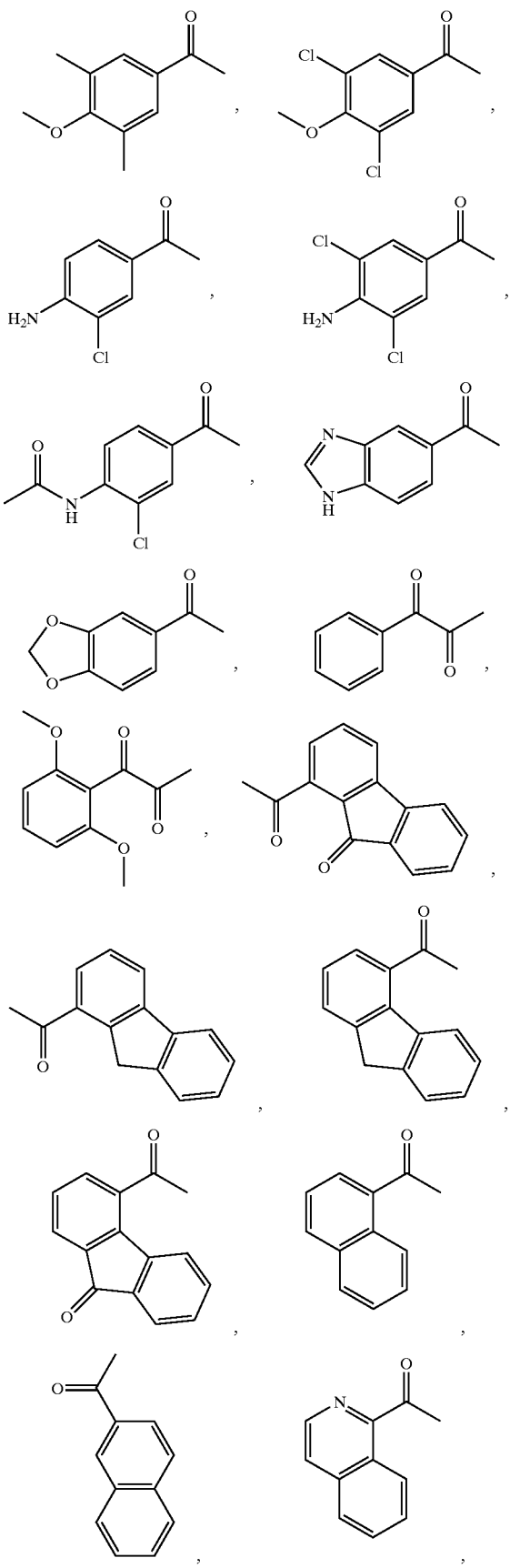

-continued

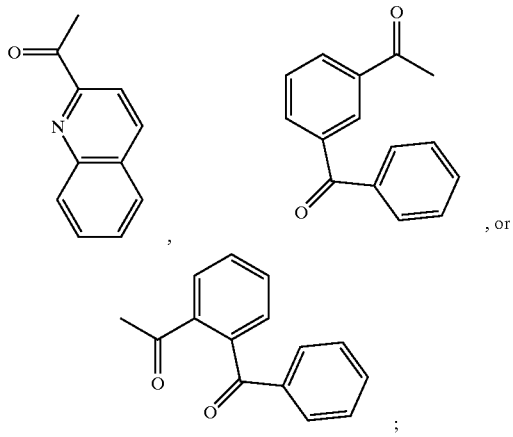

R³ is an amino acid side chain, aryl, heteroaryl, alkyl, alkylaryl, or alkylheteroaryl;

R⁸ is -alkyly, alkylcyloalky, -aryl, -alkylaryl, or -alkylheterocyclyl;

each heterocvyclyl is a mono- or plycyclic ring system which contains 1 to 15 carbon atoms and 1 to 4 heteroatoms selected from S, N, or O, in which the mono- or polycyclic ring system may optionally contain unsaturated bonds but is not aromatic;

each cycloalkyl is a mono- polycyclic, non-aromatic, hydrocarbon ring system which may optionally contain unsaturated bonds in the ring system;

each heteroaryl is a mon- or polycyclic ring system which contains 1 to 15 carbon atoms and 1 to 4 heteroatoms selected from S, N, or O, and in which at least one ring of the ring system is aromatic; and each amino acid side chain is the substituent bound to the α-carbon of a natural or non-natural α-amino acid.

18. The process according to any one of claims 16–17 wherein the inert solvent is $CH_2Cl_2$, DMF, or a mixture of $CH_2Cl_2$ and DMF.

19. The process according to any one of claims 16–17 wherein the nucleophilic scavenger is dimedone, morpholine, or dimethyl barbituric acid.

20. The process according to claim 19, wherein the nucleophilic scavenger is dimethyl barbituric acid.

21. The process according to claim 19, wherein the inert solvent is $CH_2Cl_2$, DMF, or a mixture of $CH_2Cl_2$ and DMF.

22. The process according to claim 21, wherein the nucleophilic scavenger is dimethyl barbituric acid.

* * * * *